(12) United States Patent
Bae et al.

(10) Patent No.: US 11,802,102 B2
(45) Date of Patent: Oct. 31, 2023

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG DISPLAY CO., LTD., Seoul (KR)

(72) Inventors: Suk-Young Bae, Paju-si (KR); Kyung-Jin Yoon, Paju-si (KR); Dae-Wi Yoon, Paju-si (KR); In-Ae Shin, Paju-si (KR); Mi-Sang Yoo, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 427 days.

(21) Appl. No.: 17/100,047

(22) Filed: Nov. 20, 2020

(65) Prior Publication Data
US 2021/0155566 A1    May 27, 2021

(30) Foreign Application Priority Data

Nov. 21, 2019   (KR) .................. 10-2019-0150263
Sep. 8, 2020    (KR) .................. 10-2020-0114592

(51) Int. Cl.
*C07C 13/62*    (2006.01)
*C07C 211/54*   (2006.01)
(Continued)

(52) U.S. Cl.
CPC ............ *C07C 13/62* (2013.01); *C07C 211/54* (2013.01); *C07D 407/10* (2013.01);
(Continued)

(58) Field of Classification Search
CPC ... C07C 13/62; C07C 211/54; C07C 2603/18; C07C 13/72; C07C 2603/94;
(Continued)

(56) References Cited

U.S. PATENT DOCUMENTS

2004/0076853 A1*  4/2004  Jarikov .................. C09K 11/06
                                                    428/917
2005/0106415 A1*  5/2005  Jarikov .................. C07C 13/62
                                                    428/917
(Continued)

FOREIGN PATENT DOCUMENTS

JP          2003104916 A  *  4/2003  ............. C07C 13/62
WO     WO-2010064694 A1  *  6/2010  ............. C07C 13/18
WO          2014185655 A1    11/2014

OTHER PUBLICATIONS

Jarikov, V.V., Young, R.H., Vargas, J.R., Brown, C.T., Klubek, K.P. and Liao, L.S., 2006. Operating longevity of organic light-emitting diodes with perylene derivatives as aggregating light-emitting-layer additives: Expansion of the emission zone. Journal of applied physics, 100(9), p. 094907. (Year: 2006).*

(Continued)

*Primary Examiner* — Dawn L Garrett
(74) *Attorney, Agent, or Firm* — Morgan, Lewis & Bockius LLP

(57) ABSTRACT

The present disclosure provides an organic compound of following formula and an organic light emitting diode and an OLED device including the organic compound.

(Continued)

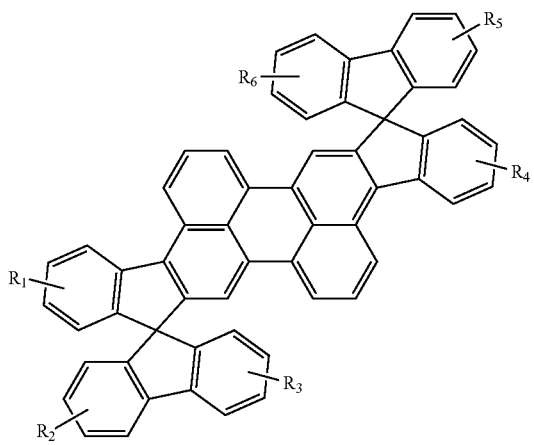

20 Claims, 6 Drawing Sheets

(51) Int. Cl.
*C07D 407/10* (2006.01)
*H10K 85/60* (2023.01)

(52) U.S. Cl.
CPC ......... *H10K 85/624* (2023.02); *H10K 85/633* (2023.02); *H10K 85/6572* (2023.02); *H10K 85/6574* (2023.02); *H10K 85/6576* (2023.02)

(58) Field of Classification Search
CPC ... C07C 211/61; C07D 407/10; C07D 209/86; C07D 307/91; C07D 333/76; H10K 85/624; H10K 85/633; H10K 85/6572; H10K 85/6574; H10K 85/6576; H10K 2101/20; H10K 50/11; H10K 85/622; C09K 11/06; C09K 2211/1011; C09K 2211/1014; C09K 2211/1029; C09K 2211/1088; C09K 2211/1092
See application file for complete search history.

(56) References Cited

U.S. PATENT DOCUMENTS

2013/0049581 A1  2/2013  Nishide et al.
2015/0380661 A1  12/2015  Kim et al.

OTHER PUBLICATIONS

Feng, X., Pisula, W. and Müllen, K., 2009. Large polycyclic aromatic hydrocarbons: synthesis and discotic organization. Pure and Applied Chemistry, 81(12), pp. 2203-2224. (Year: 2009).*
Search Report dated Feb. 18, 2023, issued in corresponding China Patent Application No. 202011245367.1.

* cited by examiner

100

D

ORGANIC COMPOUND, AND ORGANIC LIGHT EMITTING DIODE AND ORGANIC LIGHT EMITTING DISPLAY DEVICE INCLUDING THE SAME

CROSS-REFERENCE TO RELATED APPLICATIONS

The present application claims the benefit of Korean Patent Application No. 10-2019-0150263 filed in the Republic of Korea on Nov. 21, 2019, and Korean Patent Application No. 10-2020-0114592 filed in the Republic of Korea on Sep. 8, 2020, all of which are hereby incorporated by reference in their entirety.

BACKGROUND

Technical Field

The present disclosure relates to an organic compound, and more particularly, to an organic compound having high emitting efficiency, and an organic light emitting diode and an organic light emitting display (OLED) device including the organic compound.

Discussion of the Related Art

Recently, requirement for flat panel display devices having small occupied area is increased. Among the flat panel display devices, a technology of an OLED device, which includes an organic light emitting diode, is rapidly developed.

The organic light emitting diode emits light by injecting electrons from a cathode as an electron injection electrode and holes from an anode as a hole injection electrode into an organic emitting layer, combining the electrons with the holes, generating an exciton, and transforming the exciton from an excited state to a ground state. A flexible transparent substrate, for example, a plastic substrate, can be used as a base substrate where elements are formed. In addition, the organic light emitting diode can be operated at a voltage (e.g., 10V or below) lower than a voltage required to operate other display devices and has low power consumption. Moreover, the light from the organic light emitting diode has excellent color purity.

The organic light emitting diode emits light by injecting electrons from a cathode as an electron injection electrode and holes from an anode as a hole injection electrode into an emitting material layer, combining the electrons with the holes, generating an exciton, and transforming the exciton from an excited state to a ground state.

A material for the emitting material layer may be classified into a fluorescent material, a phosphorescent material and a delayed fluorescent material.

In the fluorescent material, only singlet exciton is involved in the emission such that the related art fluorescent material has low emitting efficiency.

In the phosphorescent material, both the singlet exciton and the triplet exciton are involved in the emission such that the phosphorescent material has higher emitting efficiency than the fluorescent material. However, since the phosphorescent material includes a rare earth metal, e.g., iridium (Ir), the phosphorescent material is very expensive. In addition, the related art phosphorescent material is not adequate to the blue emission.

SUMMARY

The embodiments of the present disclosure are directed to an organic compound, an organic light emitting diode and an OLED device that substantially obviate one or more of the problems associated with the limitations and disadvantages of the related conventional art.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described herein, an aspect of the present disclosure is an organic compound of:

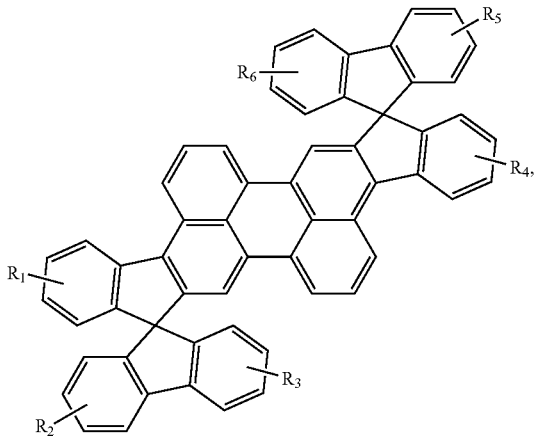

wherein each of $R_1$ to $R_6$ is independently selected from hydrogen, deuterium, tritium, halogen, a cyano group, a C1 to C20 alkyl group, a C6 to C30 aryl group, a C5 to C30 heteroaryl group and a C1 to C20 amine group.

Another aspect of the present disclosure is an organic light emitting diode including a first electrode; a second electrode facing the first electrode; and a first emitting material layer between the first and second electrodes and including an organic compound of:

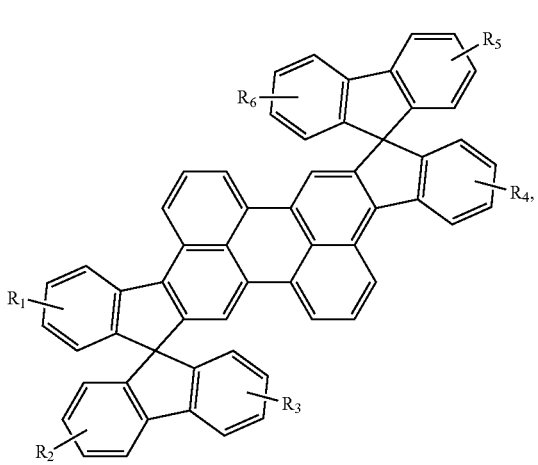

wherein each of $R_1$ to $R_6$ is independently selected from hydrogen, deuterium, tritium, halogen, a cyano group, a C1 to C20 alkyl group, a C6 to C30 aryl group, a C5 to C30 heteroaryl group and a C1 to C20 amine group.

Another aspect of the present disclosure is an organic light emitting display device including a substrate; an organic light emitting diode disposed on or over the substrate, the organic light emitting diode including: a first electrode; a second electrode facing the first electrode; and an emitting material layer between the first and second electrodes; and an encapsulation film covering the organic light emitting diode, wherein the emitting material layer includes an organic compound of:

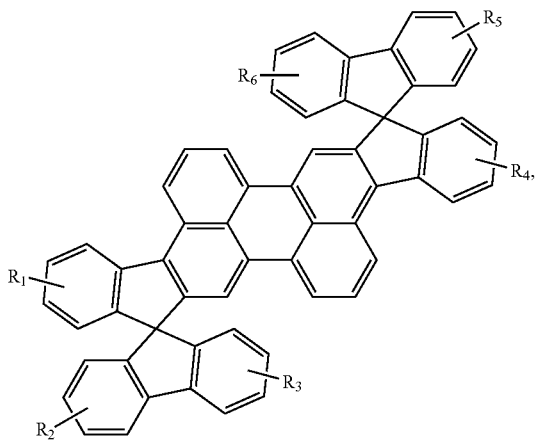

wherein each of $R_1$ to $R_6$ is independently selected from hydrogen, deuterium, tritium, halogen, a cyano group, a C1 to C20 alkyl group, a C6 to C30 aryl group, a C5 to C30 heteroaryl group and a C1 to C20 amine group.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this application, illustrate embodiments of the present disclosure and together with the description serve to explain principles of the present disclosure.

DETAILED DESCRIPTION

Reference will now be made in detail to example embodiments, which are illustrated in the accompanying drawings.

Figure 1:
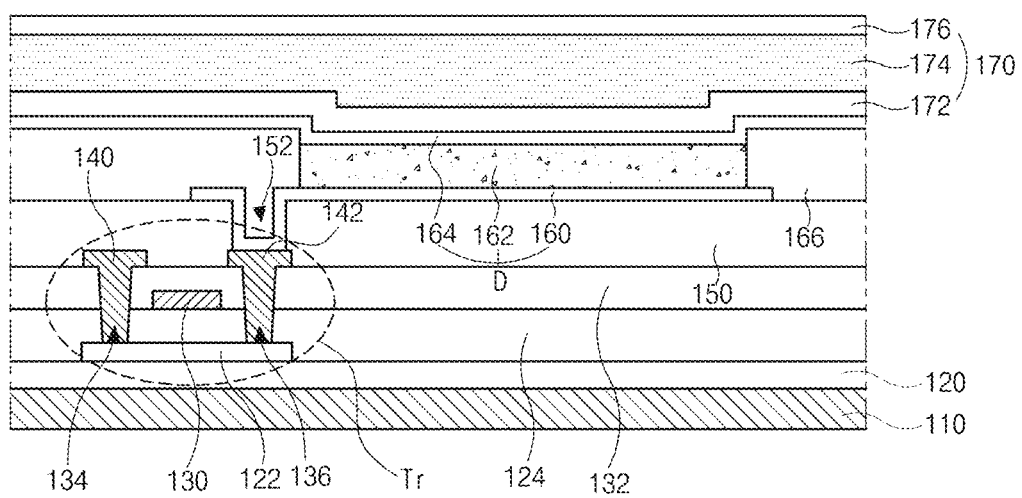
FIG. 1 is a schematic cross-sectional view of an OLED device according to a first embodiment of the present disclosure.

FIG. 1 is a schematic cross-sectional view of an OLED device according to a first embodiment of the present disclosure.

As shown in FIG. 1, the OLED device 100 includes a substrate 110, a TFT Tr and an organic light emitting diode D connected to the TFT Tr.

The substrate 110 may be a glass substrate or a plastic substrate. For example, the substrate 110 may be a polyimide substrate.

A buffer layer 120 is formed on the substrate 110, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 1, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both sides of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element.

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A passivation layer (or planarization layer) 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel region. The first electrode 160 may be an anode and may be formed of a conductive material having a relatively high work function. For example, the first electrode 160 may be formed of a transparent conductive material such as indium-tin-oxide (ITO) or indium-zinc-oxide (IZO).

When the OLED device 100 is operated in a bottom-emission type, the first electrode 160 may have a single-layered structure of the transparent conductive material layer. When the OLED device 100 is operated in a top-emission type, a reflection electrode or a reflection layer may be formed under the first electrode 160. For example, the reflection electrode or the reflection layer may be formed of silver (Ag) or aluminum-palladium-copper (APC) alloy. In this instance, the first electrode 160 may have a triple-layered structure of ITO/Ag/ITO or ITO/APC/ITO.

A bank layer 166 is formed on the passivation layer 150 to cover an edge of the first electrode 160. Namely, the bank layer 166 is positioned at a boundary of the pixel region and exposes a center of the first electrode 160 in the pixel region.

An organic emitting layer 162 is formed on the first electrode 160. The organic emitting layer 162 includes an organic compound of the present disclosure. The organic compound of the present disclosure serves as a dopant, and the organic emitting layer 162 may further include a host. For example, the organic compound of the present disclosure as the dopant may be doped by about 0.1 to 10 wt % with respect to the host. The organic emitting layer 162 may further include a delayed fluorescent compound as another dopant. In this instance, the delayed fluorescent compound may be doped by about 10 to 50 wt % with respect to the host, and a summation of the organic compound of the present disclosure and the delayed fluorescent compound may be about 10.1 to 60 wt % with respect to the host. The organic emitting layer 162 provide a blue emission.

The organic emitting layer 162 may have a single-layered structure of an emitting material layer (EML) including the organic compound of the present disclosure. To increase an emitting efficiency of the OLED device, the organic emitting layer 162 may have a multi-layered structure.

A second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg) or Al—Mg alloy. In the top-emission type OLED device 100, the second electrode 164 may have a thin profile (small thickness) to provide a light transmittance property (or a semi-transmittance property).

The first electrode 160, the organic emitting layer 162 and the second electrode 164 constitute the organic light emitting diode D.

An encapsulation film 170 is formed on the second electrode 164 to prevent penetration of moisture into the organic light emitting diode D. The encapsulation film 170 includes a first inorganic insulating layer 172, an organic insulating layer 174 and a second inorganic insulating layer 176 sequentially stacked, but it is not limited thereto.

The OLED device 100 may further include a polarization plate (not shown) for reducing an ambient light reflection. For example, the polarization plate may be a circular polarization plate. In the bottom-emission type OLED device 100, the polarization plate may be disposed under the substrate 110. In the top-emission type OLED device 100, the polarization plate may be disposed on or over the encapsulation film 170.

In addition, in the top-emission type OLED device 100, a cover window (not shown) may be attached to the encapsulation film 170 or the polarization plate. In this instance, the substrate 110 and the cover window have a flexible property such that a flexible OLED device may be provided.

Figure 2:
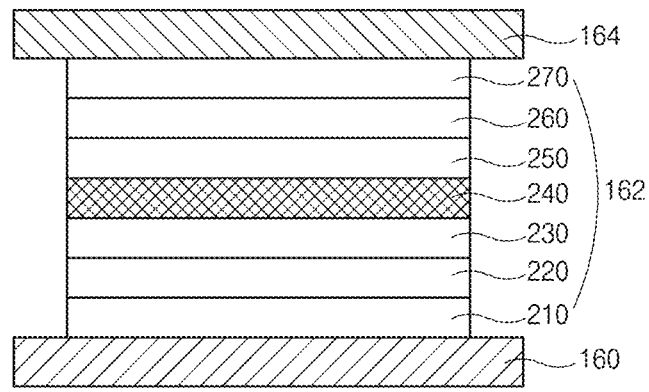
FIG. 2 is a schematic cross-sectional view of an organic light emitting diode according to a second embodiment of the present disclosure.

FIG. 2 is a schematic cross-sectional view of an organic light emitting diode according to a second embodiment of the present disclosure.

As shown in FIG. 2, the organic light emitting diode D includes the first and second electrodes 160 and 164, which face each other, and the organic emitting layer 162 therebetween. The organic emitting layer 162 includes an emitting material layer (EML) 240 between the first and second electrodes 160 and 164.

The organic emitting layer 162 may further include a hole transporting layer (HTL) 220 between the first electrode 160 and the EML 240 and an electron transporting layer (ETL) 260 between the second electrode 164 and the EML 240.

In addition, the organic emitting layer 162 may further include a hole injection layer (HIL) 210 between the first electrode 160 and the HTL 220 and an electron injection layer (EIL) 270 between the second electrode 164 and the ETL 260.

Moreover, the organic emitting layer 162 may further include an electron blocking layer (EBL) 230 between the HTL 220 and the EML 240 and a hole blocking layer (HBL) 250 between the EML 240 and the ETL 260.

The OLED device 100 (of FIG. 1) may include a red pixel region, a green pixel region and a blue pixel region, and the organic light emitting diode D may be positioned in the green pixel region.

The organic emitting layer 162, preferably the EML 240 includes an organic compound of Formula 1 as a host and further includes a dopant.

[Formula 1]

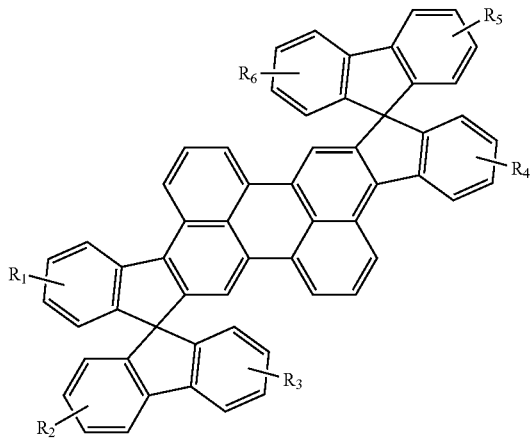

In Formula 1, each of $R_1$ to $R_6$ is independently selected from hydrogen, deuterium, tritium, halogen, a cyano group, a C1 to C20 alkyl group, a C6 to C30 aryl group, a C5 to C30 heteroaryl group and a C1 to C20 amine group.

For example, each of $R_1$ to $R_6$ may be independently selected from hydrogen, methyl, iso-propyl, tert-butyl, phenyl, diphenyl amine, carbazolyl, dibenzofuranyl and dibenzothiophenyl.

In the present disclosure, the term of 'hetero' in 'heteroaromatic ring', 'hetero-cycloalkyl group', 'heteroaryl group', 'heteroaralkyl group', 'heteroaryloxy group', 'heteroaryl amine group', 'heteroarylene group', 'heteroaralkylene group', 'hetero aryloxylene group', etc., means that one or more of carbon atoms, e.g., 1 to 5 carbon atoms, constituting these aromatic or alicyclic rings is substituted by one or more hetero-atom selected from the group consisting of N, O, S and their combinations.

The organic compound of the present disclosure includes a perylene core having a rigid structure and a spiro moiety connected (bonded or combined) to the perylene core such that high emitting efficiency is provided. For example, the organic compound may be used as a fluorescent dopant in the EML 240 of the organic light emitting diode.

When the molecular weight of an organic compound in the EML 240 is excessively increased, the sublimation temperature of the organic compound is increased. Typically, a vapor deposition method is used for forming the EML 240 of the organic light emitting diode D. When an organic compound having a high sublimation temperature is used, the sublimation does not occur at a temperature, in which there is no damage to the organic light emitting diode D. such that the deposition of the EML 240 may not be possible. On the other hand, when a high temperature is applied to sublimate the organic compound, damage may be applied to the organic light emitting diode D.

Therefore, preferably, in Formula 1 of the organic compound of the present disclosure, two or less (one or two) of $R_1$ to $R_3$ and two or less (one or two) of $R_4$ to $R_6$ may be independently selected from halogen, a cyano group, a C1 to C20 alkyl group, a C6 to C30 aryl group, a C5 to C30 heteroaryl group and a C1 to C20 amine group, and the rest of $R_1$ to $R_6$ may be selected from hydrogen, deuterium, and tritium.

Preferably, the organic compound of the present disclosure may be represented by one of Formulas 2-1 to 2-3.

[Formula 2-1]

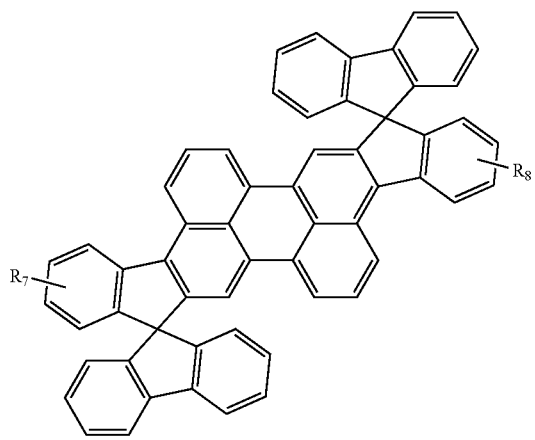

[Formula 2-2]

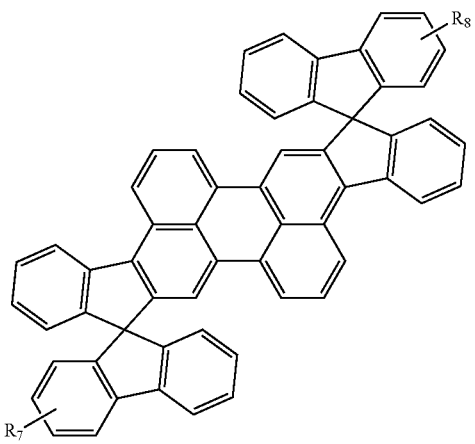

[Formula 2-3]

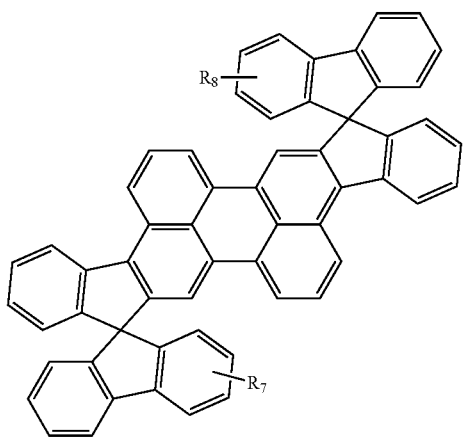

In Formulas 2-1 to 2-3, each of $R_7$ and $R_8$ is independently selected from hydrogen, deuterium, tritium, halogen, cyano group, a C1 to C20 alkyl group, a C6 to C30 aryl group, a C5 to C30 heteroaryl group and a C1 to C20 amine group.

For example, at least one of $R_7$ and $R_8$ may be selected from hydrogen, deuterium and tritium.

For example, the organic compound of the present disclosure may be one of compounds in Formula 3.

[Formula 3]
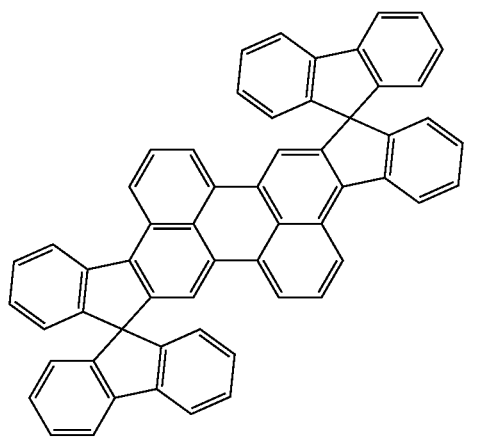
1-1
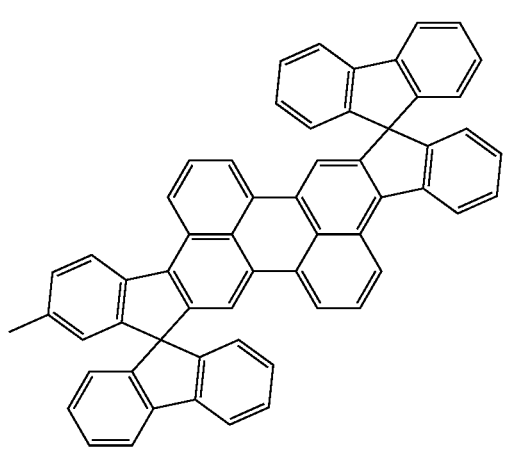
1-2
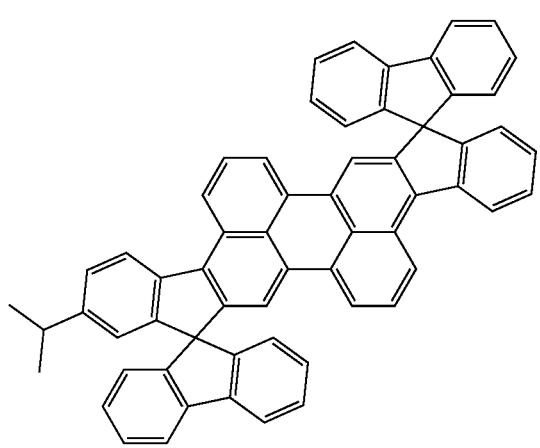
1-3

1-4
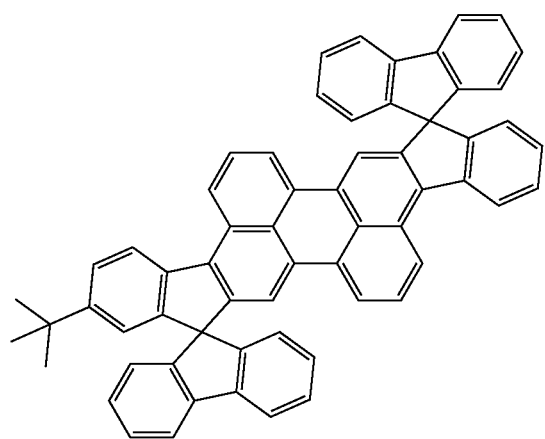
1-5
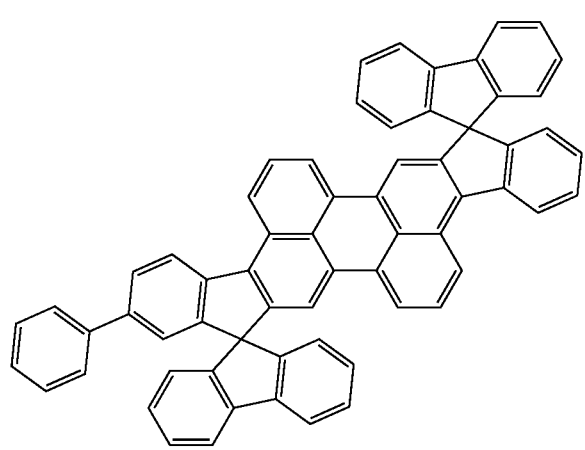
1-6
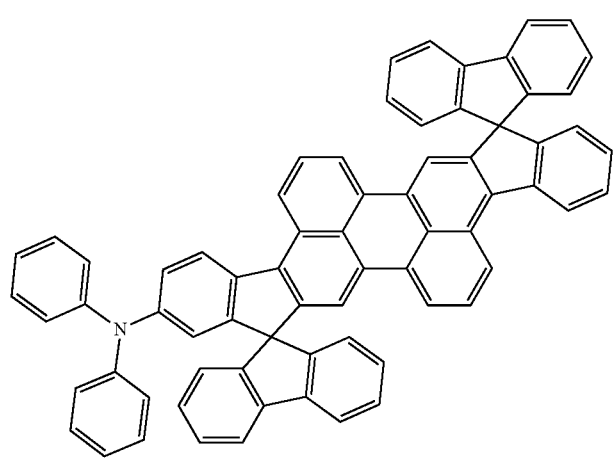

1-7
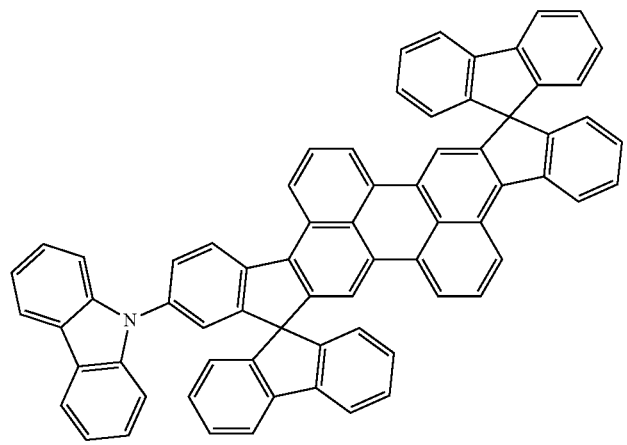
1-8
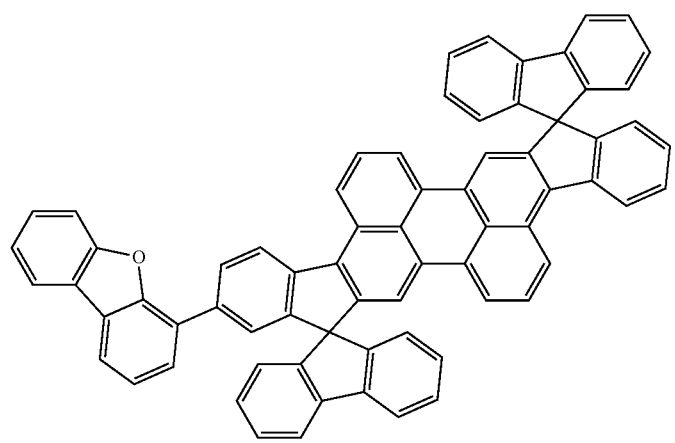
1-9
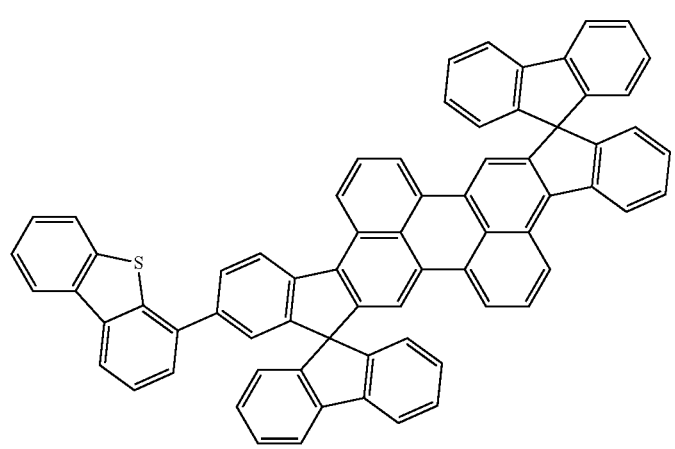

1-10
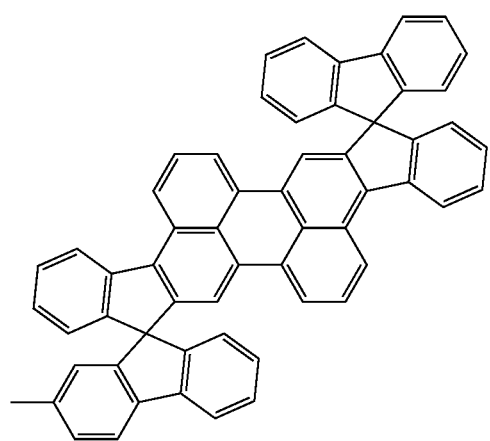
1-11
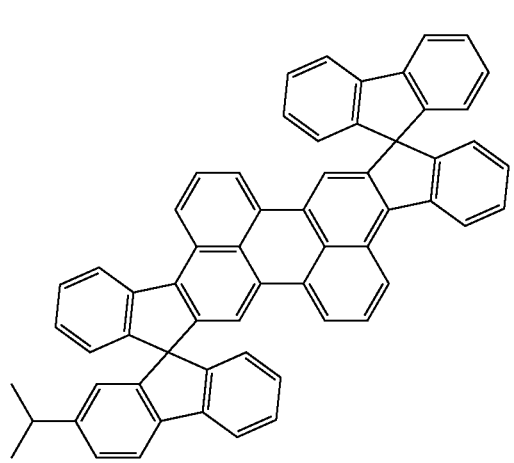
1-12
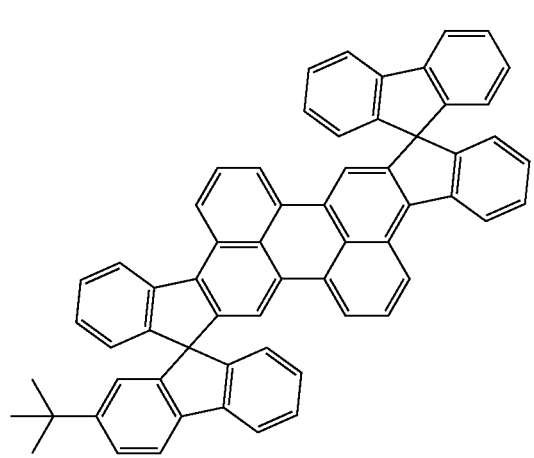

-continued
1-13
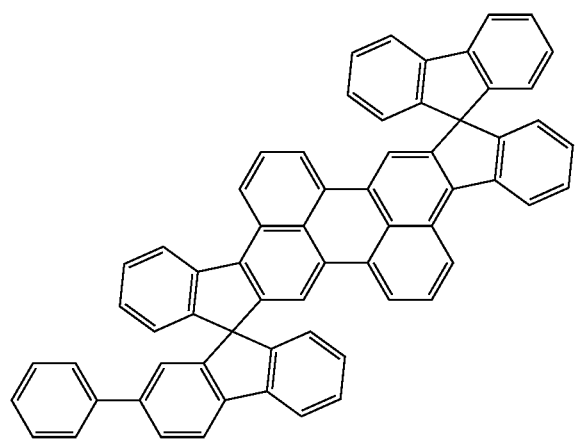
1-14
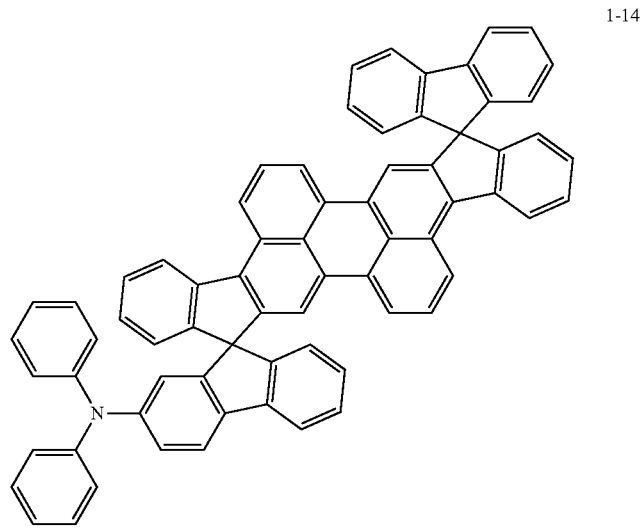
1-15
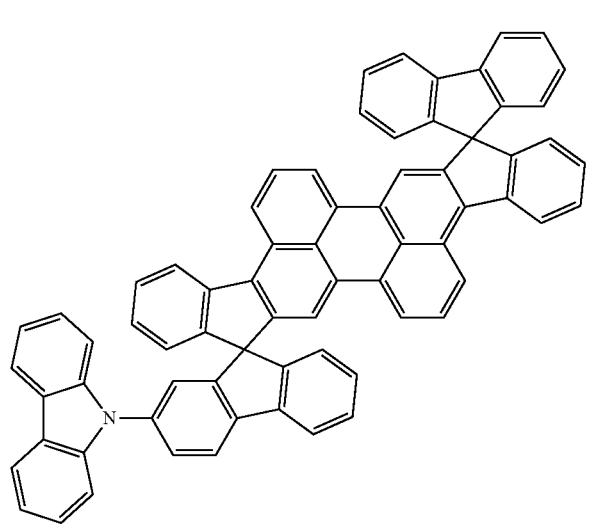

-continued
1-16
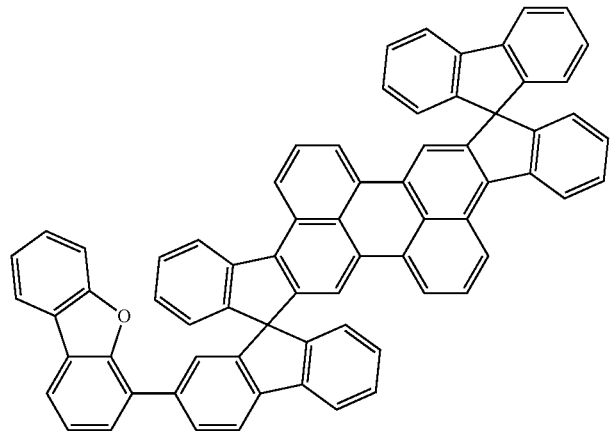
1-17
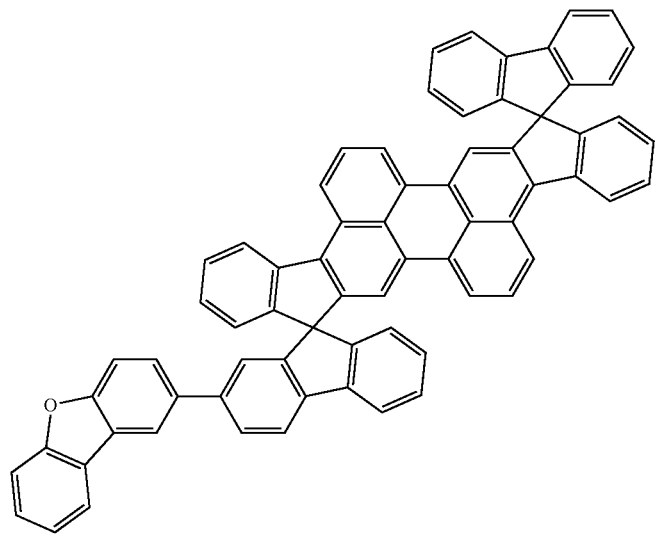
1-18
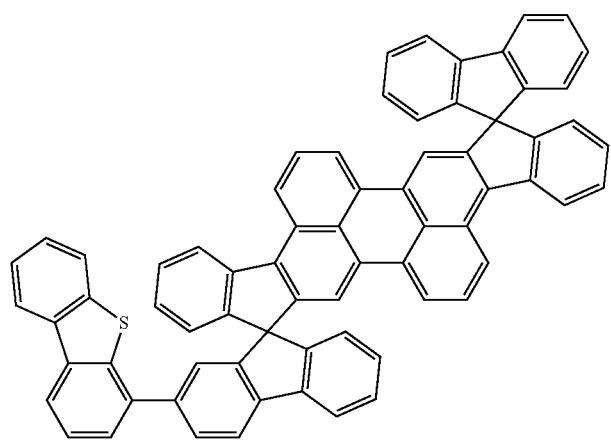

1-19
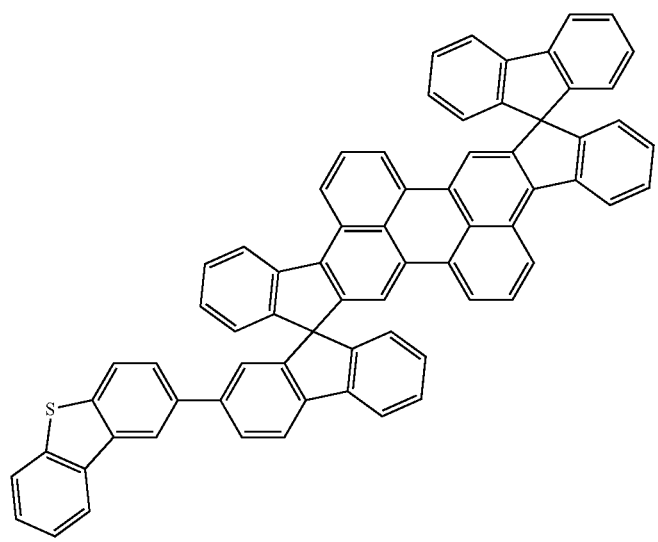
1-20
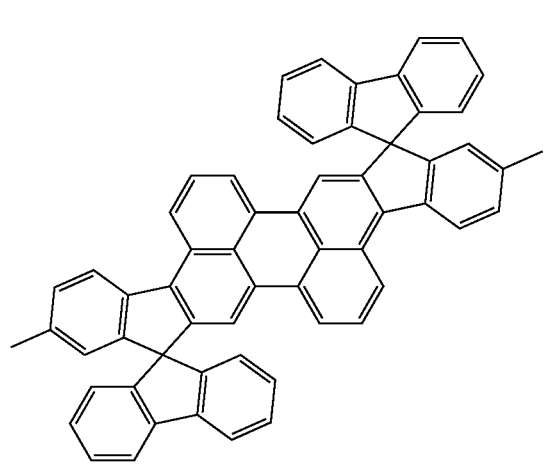
1-21
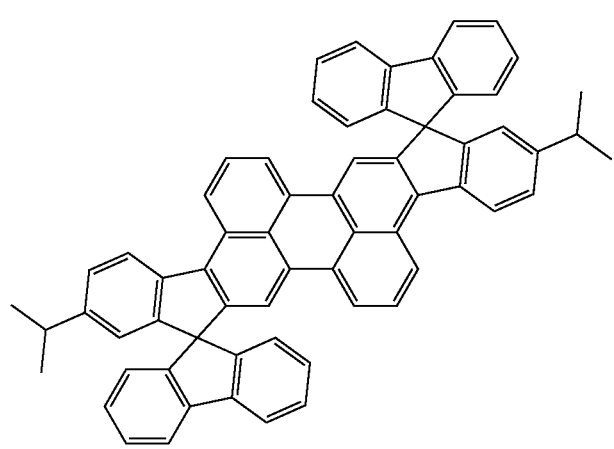

1-22
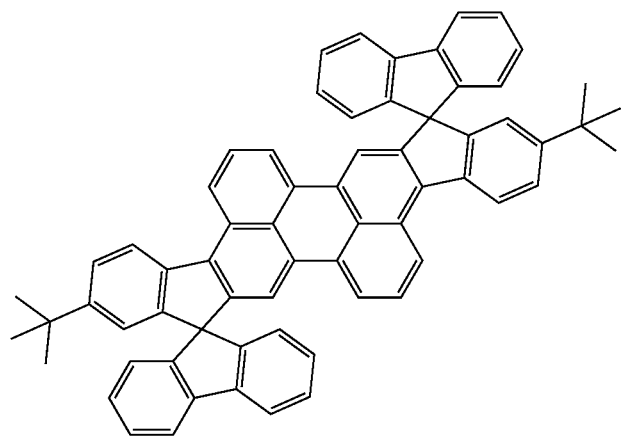
1-23
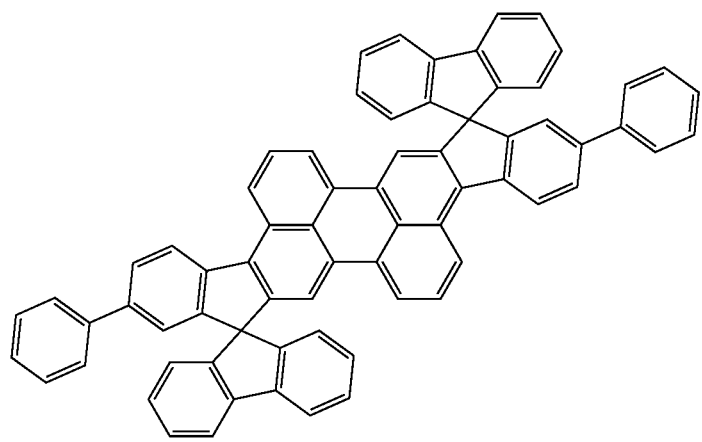
1-24
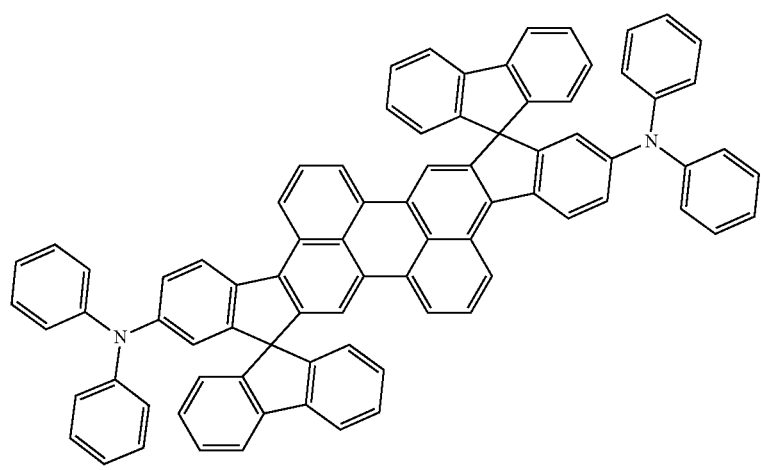

-continued
1-25
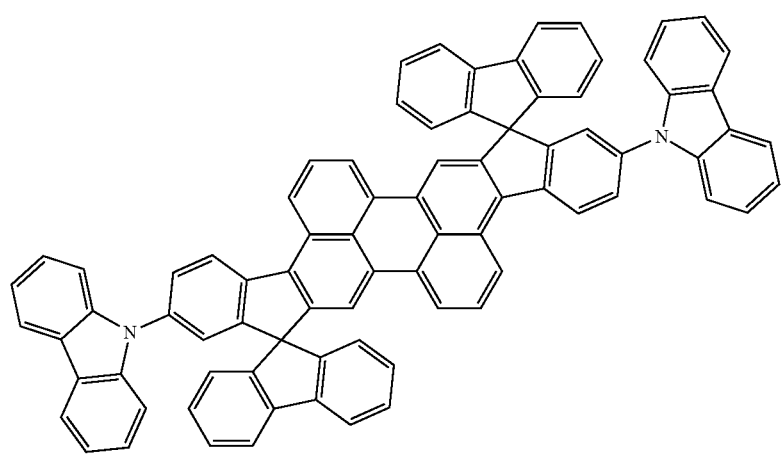
1-26
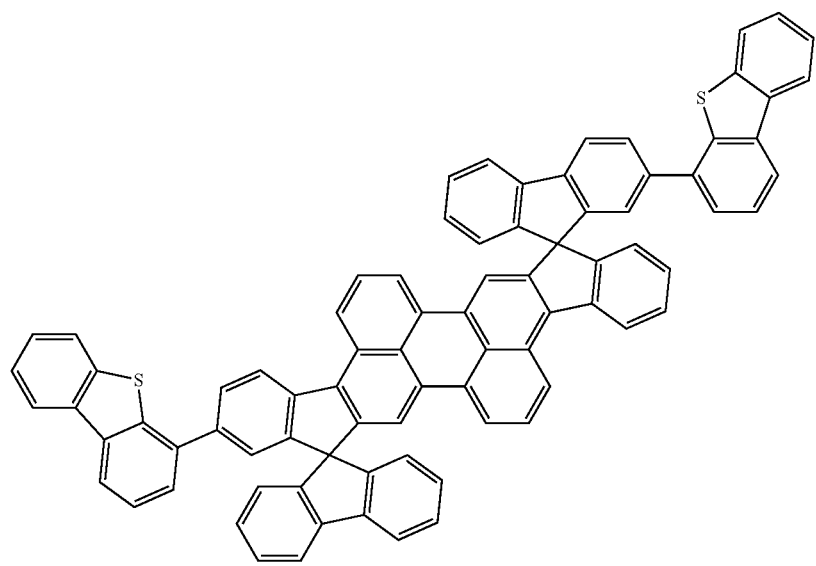
1-27
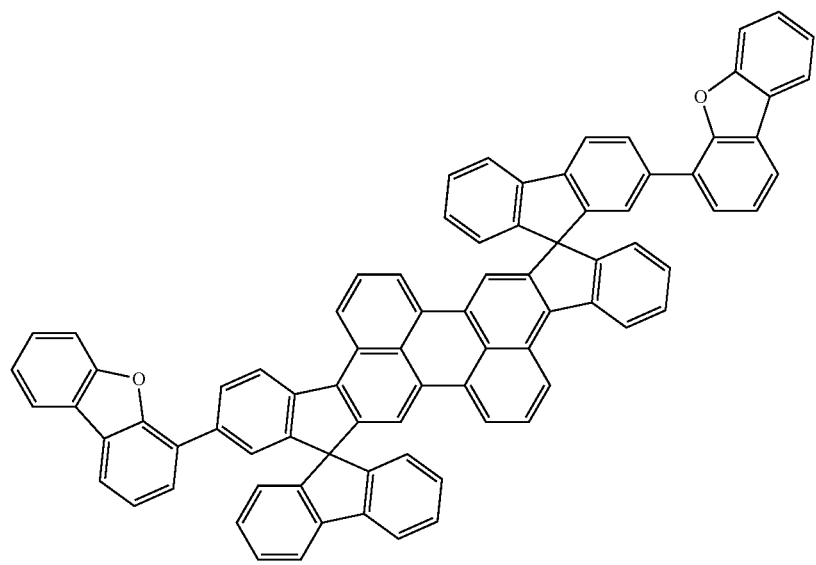

-continued
1-28
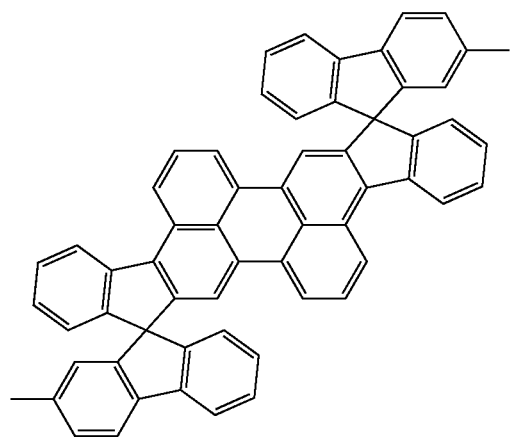
1-29
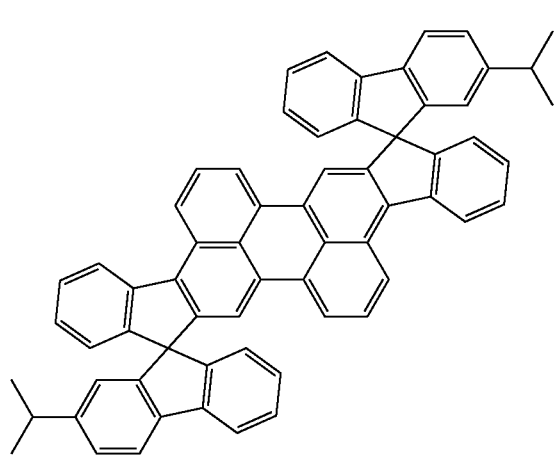
1-30
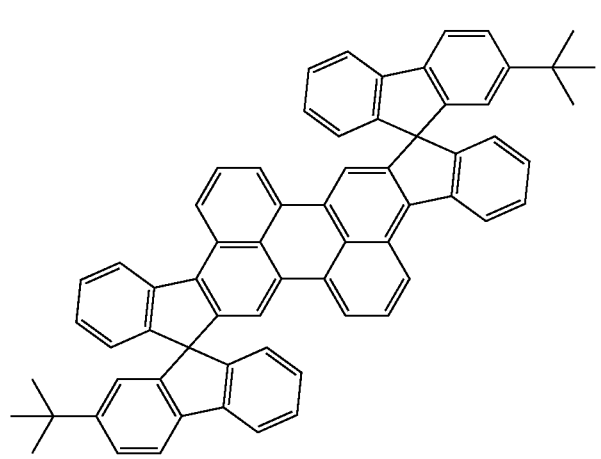

-continued
1-31
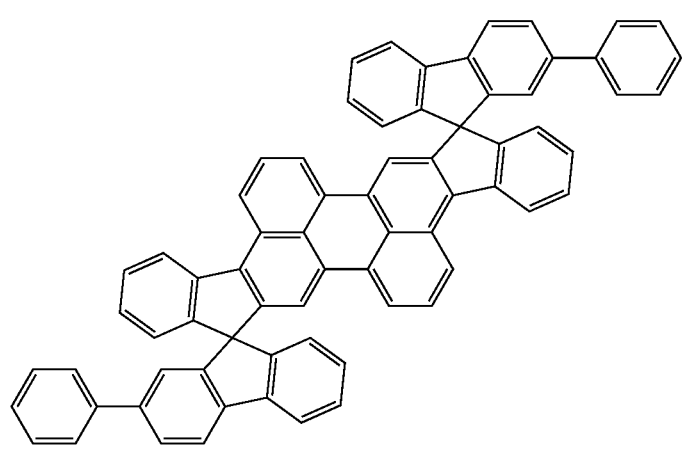
1-32
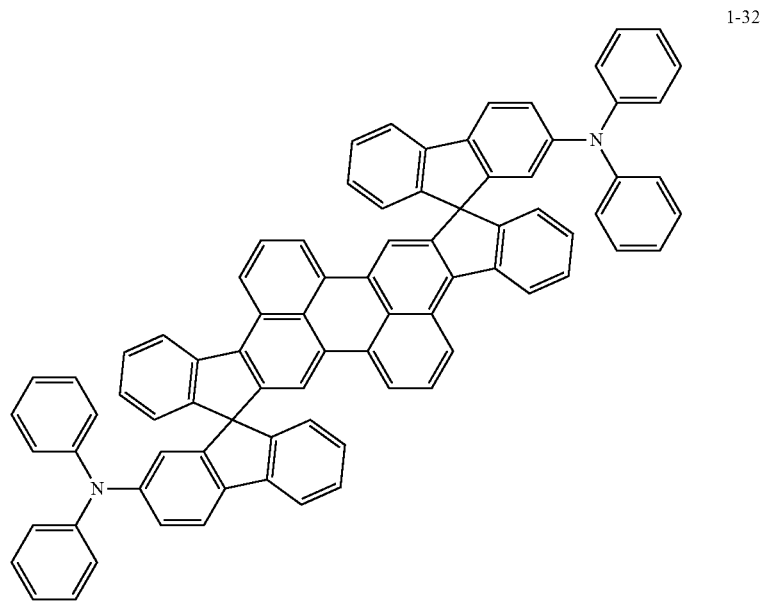
1-33
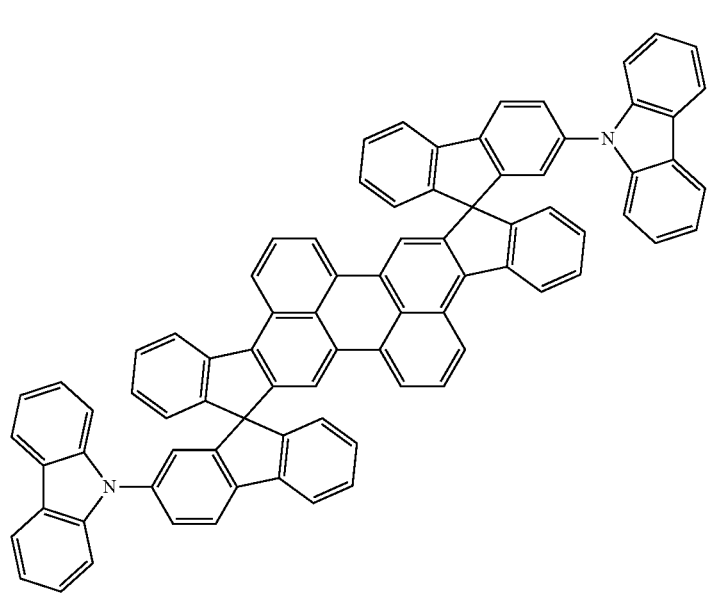

-continued
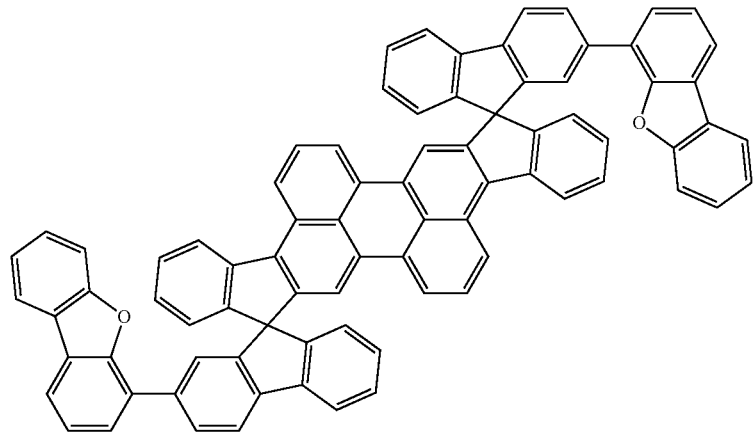
1-34
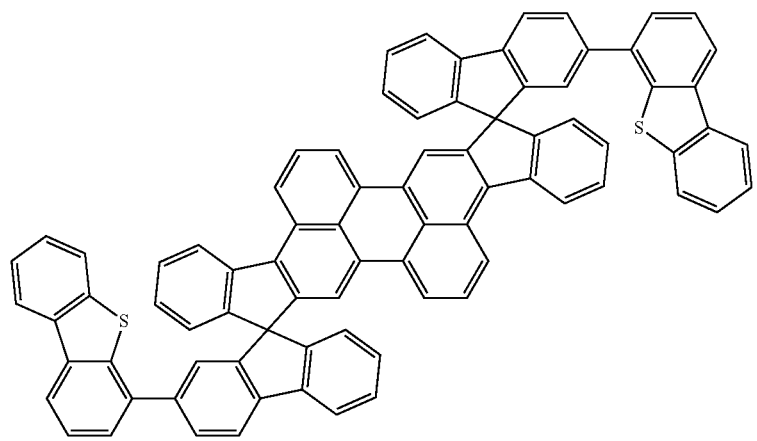
1-35
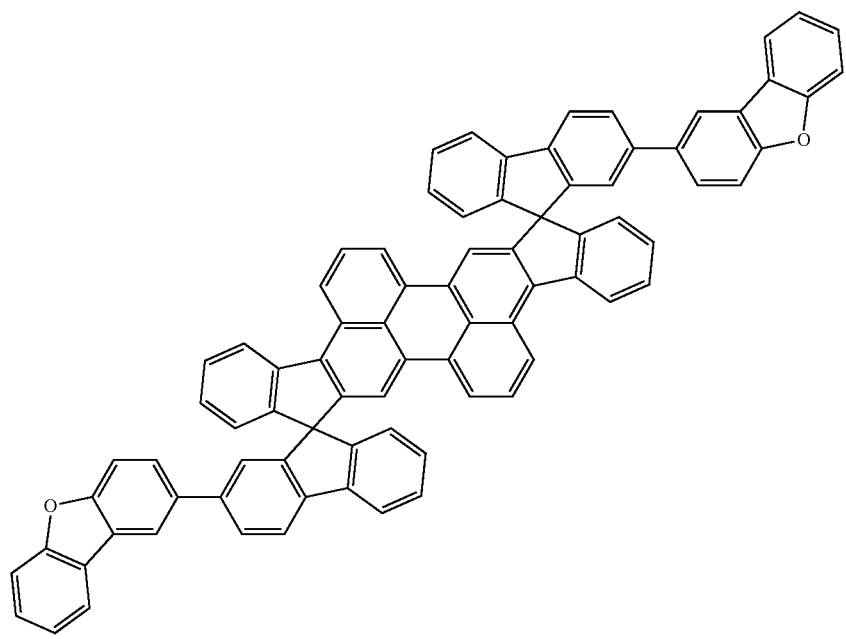
1-36

-continued
1-37
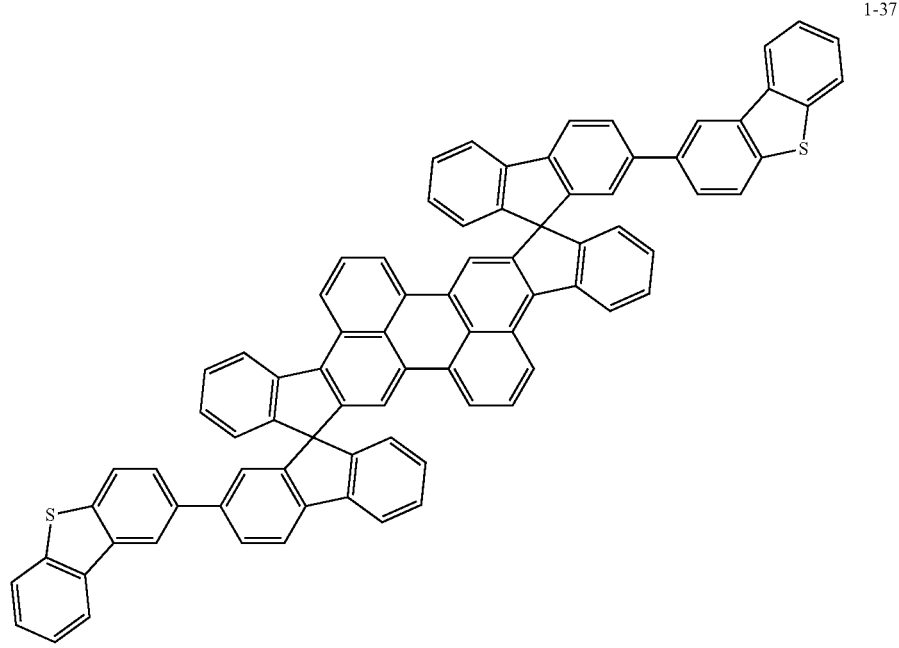
1-38
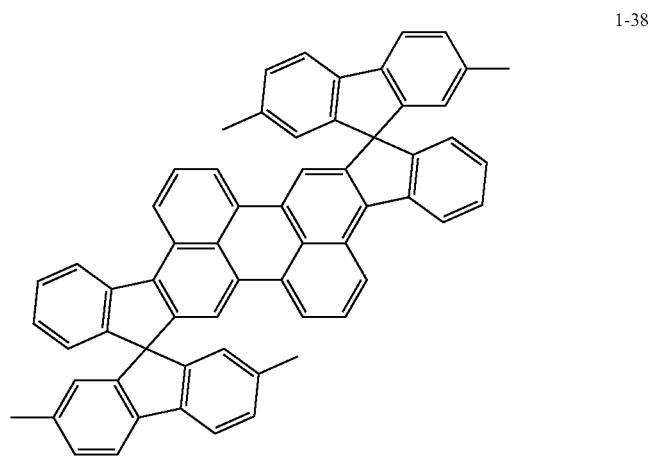
1-39
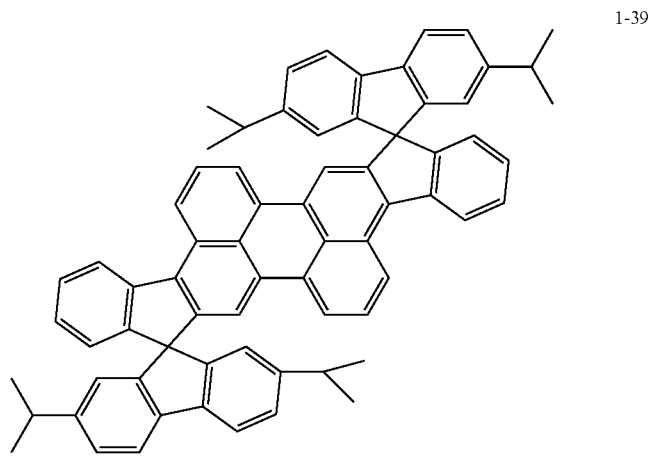

1-40
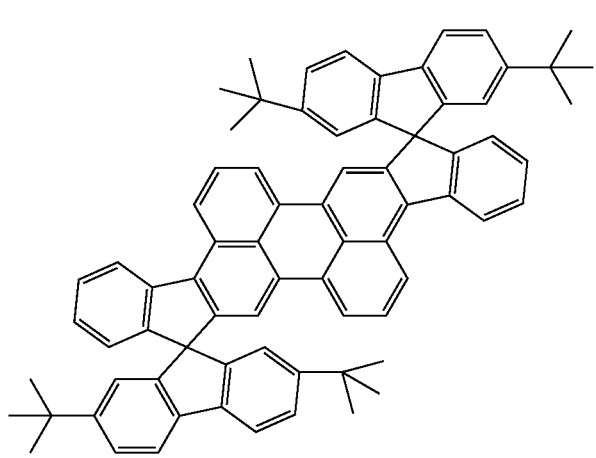
1-41
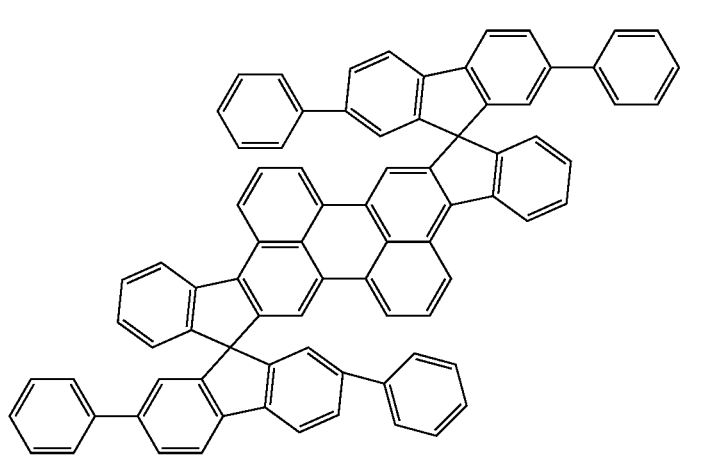
1-42
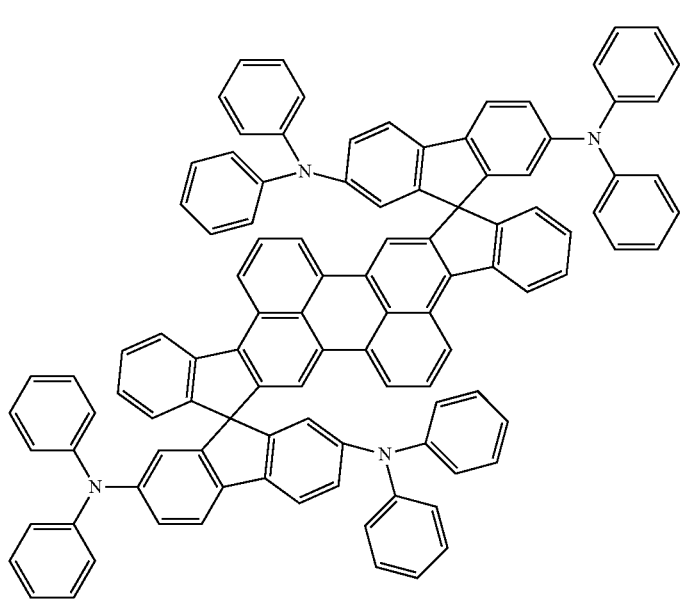

1-43
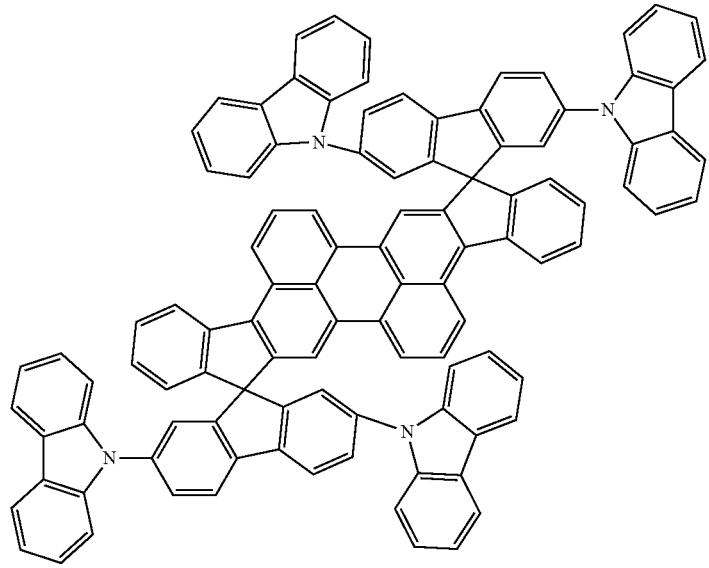
1-44
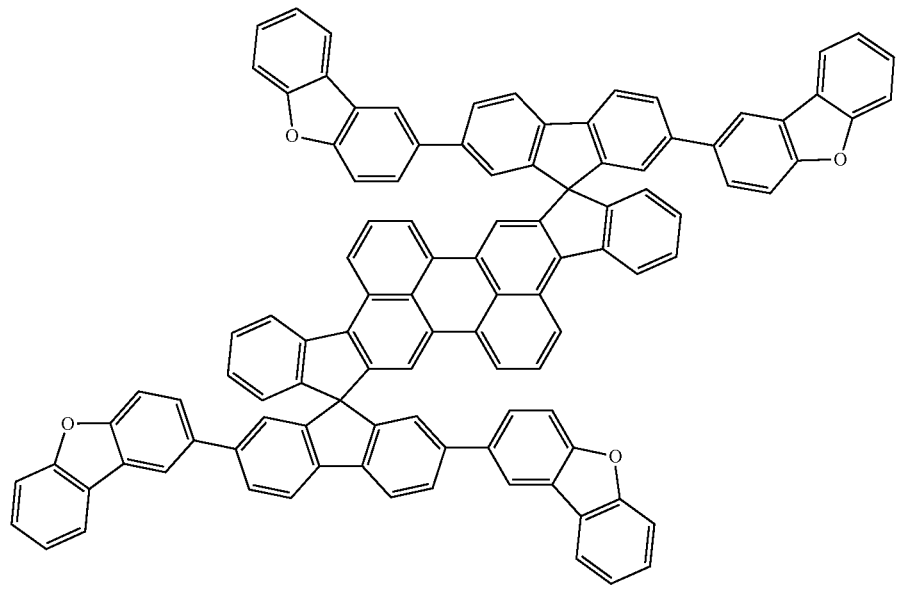

1-45
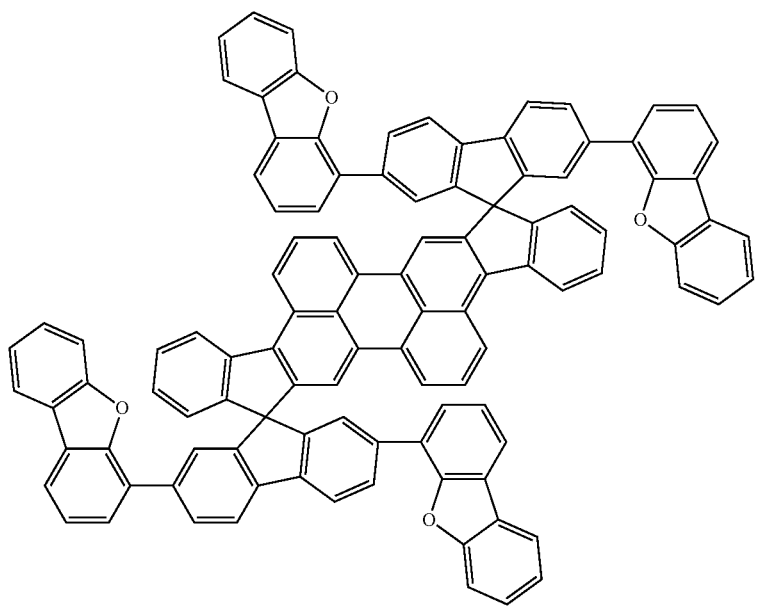
1-46
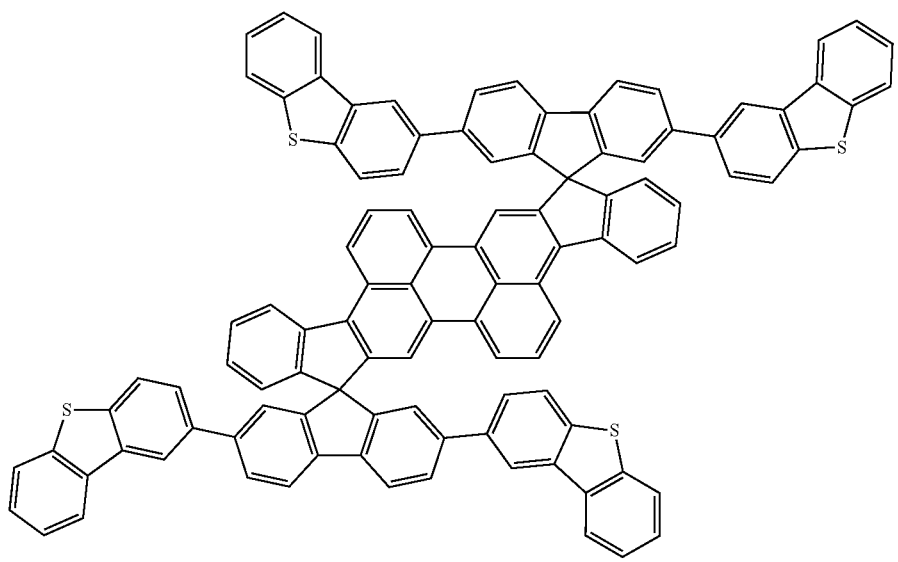

-continued

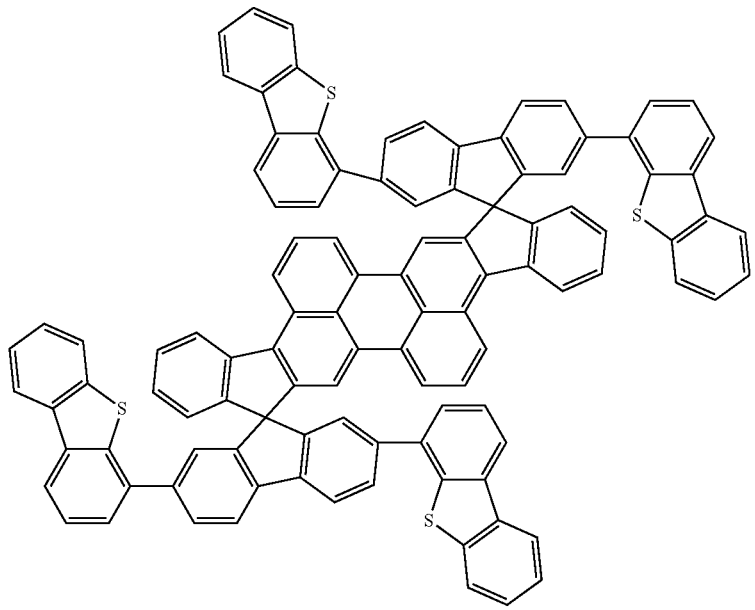

1-47

[Synthesis of Organic Compounds]
1. Synthesis of Compound 1-1
(1) Compound A-1

[Reaction Formula 1-1]

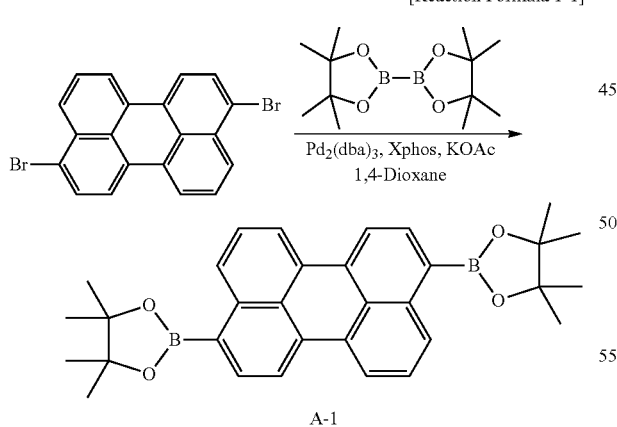

In a 2-neck flask (500 ml), 3,9-dibromoperylene (8.0 g, 19.51 mmol), bis(pinacolato)diboran (24.77 g, 97.54 mmol), $Pd_2(dba)_3$ (0.54 g, 0.59 mmol), XPhos (0.56 g, 1.17 mmol) and KOAc (6.70 g, 68.28 mmol) were dissolved by 1,4-dioxane (300 mL). The mixture was refluxed and stirred for 12 hrs. After completion of reaction, the mixture was columned by hexane and ethyl acetate (volume ratio=10.1) to obtain the compound A-1. (5.00 g, yield=50.83%)

(2) Compound A-2

[Reaction Formula 1-2]

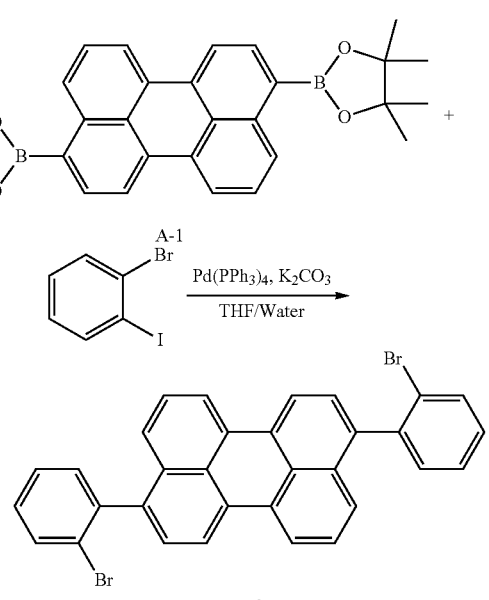

In a 2-neck flask (500 ml), the compound A-1 (5.00 g, 9.92 mmol), 1-bromo-2-iodobenzene (6.17 g, 21.82 mmol), $K_2CO_3$ (6.85 g, 49.58 mmol) and $Pd(PPh_3)_4$ (0.34 g, 0.30 mmol) were dissolved by a mixed solution of tetrahydrofuran (THF) and water (volume ratio=3:1, 200 ml). The mixture was refluxed and stirred for 12 hrs. After completion of reaction, the mixture was columned by methylenechloride (MC) and hexane (volume ratio=3:7) to obtain the compound A-2. (4.50 g, yield=80.71%)

(3) Compound 1-1

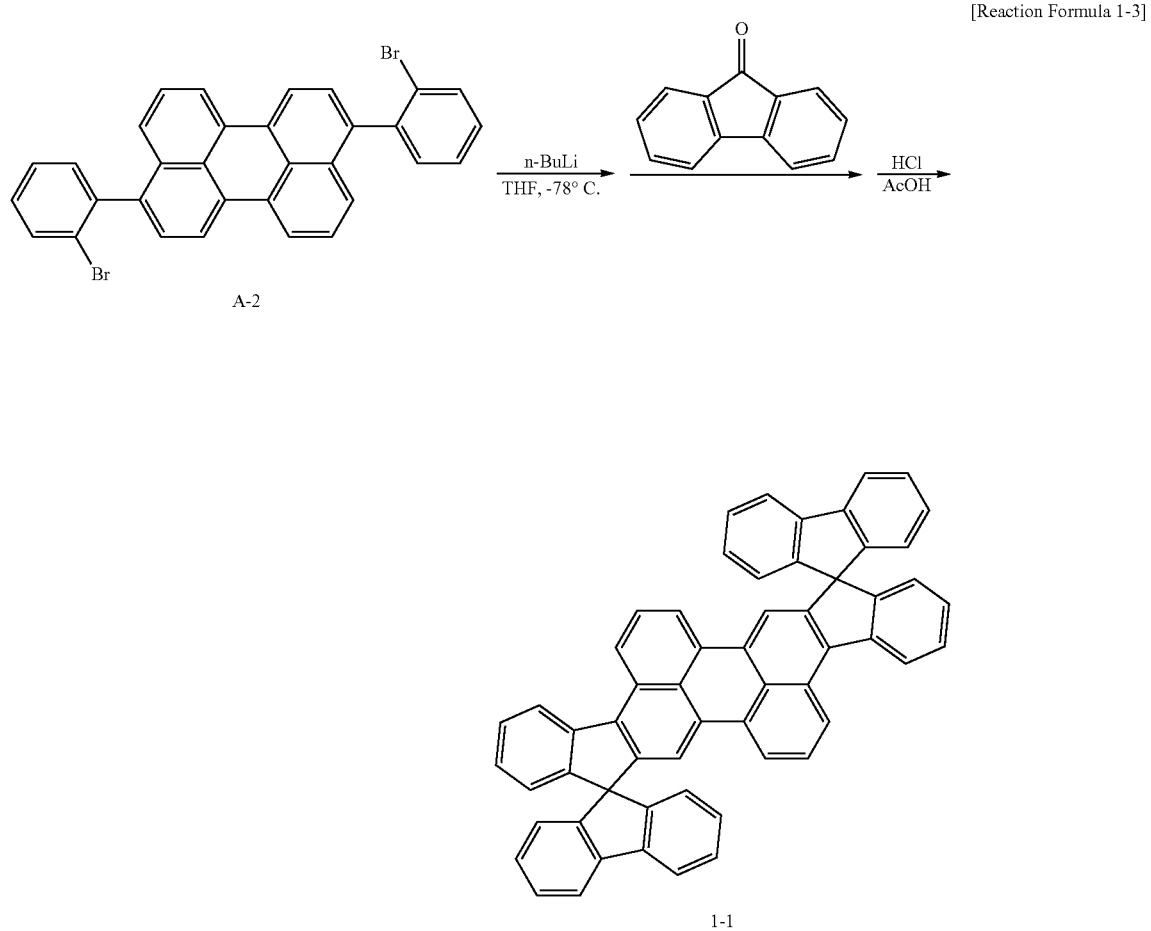

In a 2-neck flask (250 ml), the compound A-2 (3.00 g, 5.34 mmol) was dissolved by THF (100 ml). The mixture was cooled into −78° C., and n-butyllithium (2.5M in hexane, 4.70 mL, 11.74 mmol) was slowly added. After 2 hrs, 9H-fluoren-9-one (2.12 g, 11.74 mmol) was added into the mixture. After 3 hrs, the reaction was finished by adding distilled water, and the mixture was extracted by MC. The water in the mixture was dried by MgSO₄, and the solution in the mixture was removed. The mixture was precipitated by ethanol, and the solid was filtered. The solid was dissolved by acetic acid (100 ml), and HCl was added. The mixture was refluxed and stirred for 6 hrs and cooled into the room temperature. The solid was filtered and washed by ethanol. After the solid was dried, the solid was columned by MC and hexane (volume ratio=1:4) to obtain the compound 1-1. (1.5 g, yield=38.57%)

2. Synthesis of Compound 1-22

(1) Compound B-1

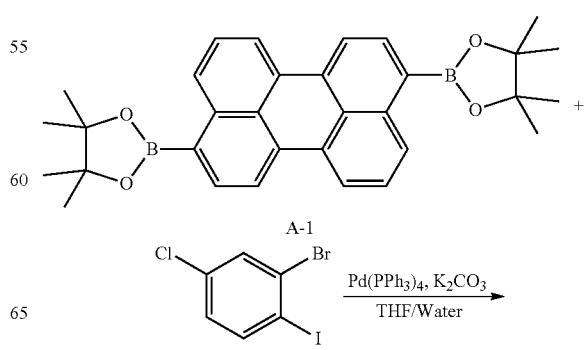

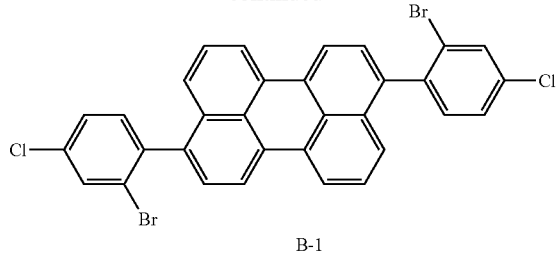

B-1

In a 2-neck flask (500 ml), the compound A-1 (5.00 g, 9.92 mmol), 2-bromo-4-chloro-1-iodobenzene (6.92 g, 21.82 mmol), $K_2CO_3$ (6.85 g, 49.58 mmol) and $Pd(PPh_3)_4$ (0.34 g, 0.30 mmol) were dissolved by a mixed solution of THF and water (volume ratio=3:1, 200 ml). The mixture was refluxed and stirred for 12 hrs. After completion of reaction, the mixture was columned by MC and hexane (volume ratio=3:7) to obtain the compound B-1. (2.0 g, yield=31.95%)

(2) Compound B-2

[Reaction Formula 2-2]

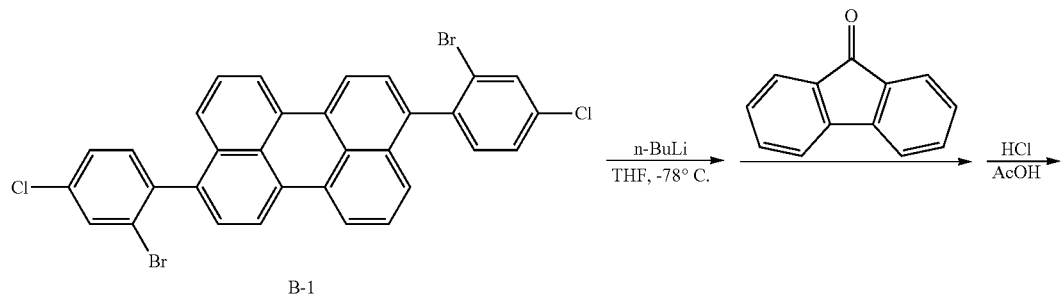

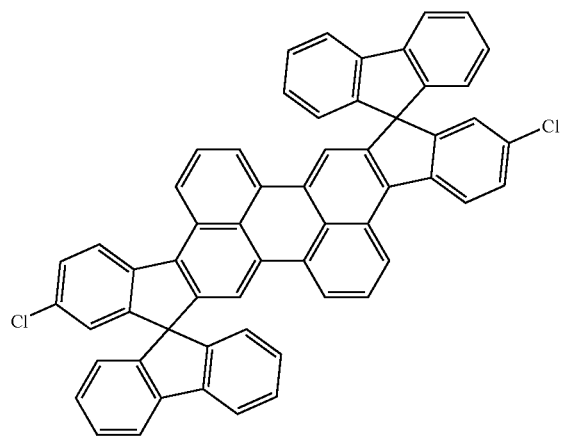

B-2

In a 2-neck flask (250 ml), the compound B-1 (2.00 g, 3.17 mmol) was dissolved by THF (100 ml). The mixture was cooled into −78° C., and n-butyllithium (2.5M in hexane, 2.79 mL, 6.97 mmol) was slowly added. After 2 hrs, 9H-fluoren-9-one (1.26 g, 6.97 mmol) was added into the mixture. After 3 hrs, the reaction was finished by adding distilled water, and the mixture was extracted by MC. The water in the mixture was dried by MgSO$_4$, and the solution in the mixture was removed. The mixture was precipitated by ethanol, and the solid was filtered. The solid was dissolved by acetic acid (100 ml), and HCl was added. The mixture was refluxed and stirred for 6 hrs and cooled into the room temperature. The solid was filtered and washed by ethanol. After the solid was dried, the solid was columned by MC and hexane (volume ratio=1:4) to obtain the compound B-2. (0.75 g, yield=29.67%)

(3) Compound 1-22

[Reaction Formula 2-3]

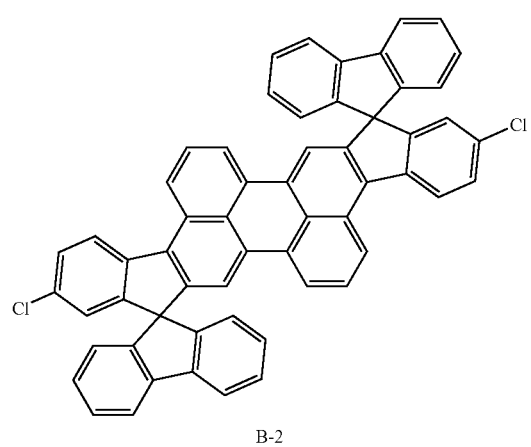

B-2

+

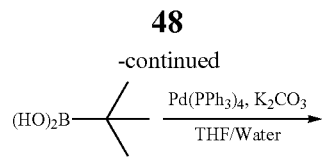

-continued

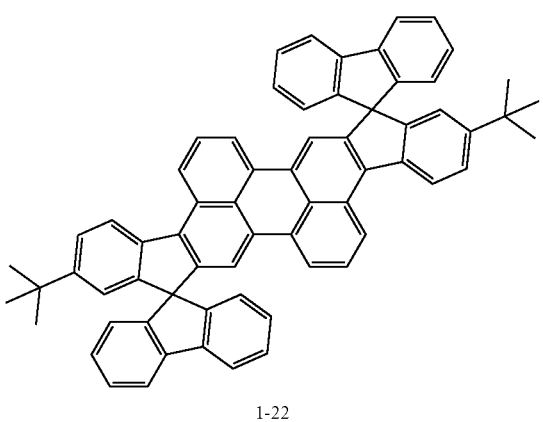

1-22

In a 2-neck flask (500 ml), the compound B-2 ((0.70 g, 0.88 mmol), tert-butylboronic acid (0.21 g, 2.02 mmol), K$_2$CO$_3$ (0.61 g, 4.39 mmol) and Pd(PPh$_3$)$_4$ (0.03 g, 0.03 mmol) were dissolved by a mixed solution of THF and water (volume ratio=3:1, 60 ml). The mixture was refluxed and stirred for 12 hrs. After completion of reaction, the mixture was columned by MC and hexane (volume ratio=3:7) to obtain the compound 1-22. (0.50 g, yield=67.75%)

3. Synthesis of Compound 1-30

(1) Compound C-1

[Reaction Formula 3-1]

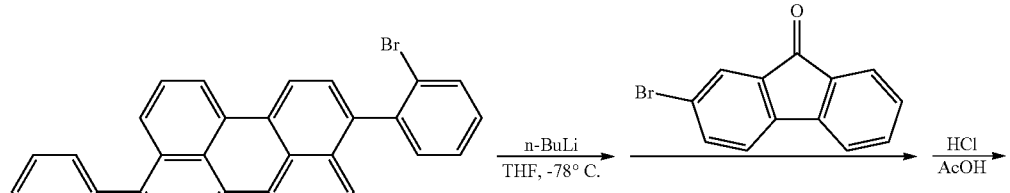

A-2

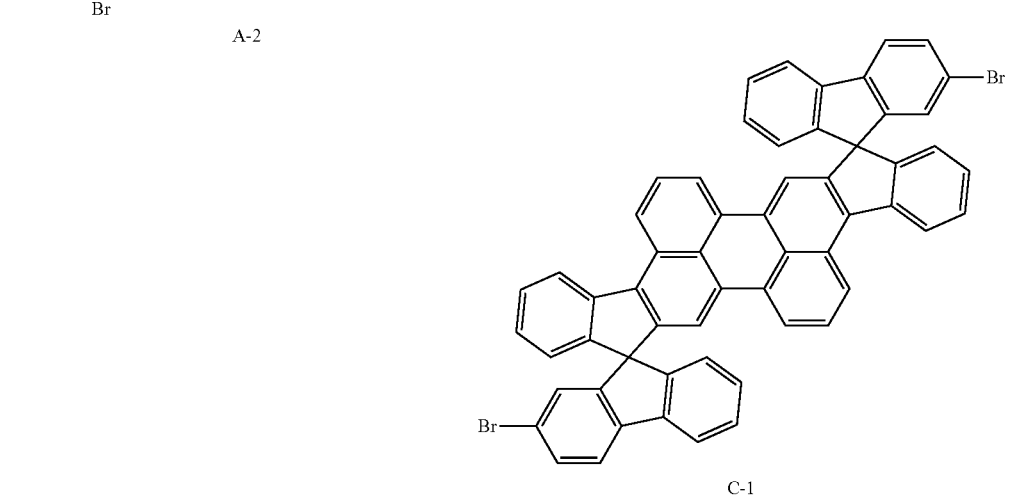

C-1

In a 2-neck flask (500 ml), the compound A-2 (5.00 g, 8.89 mmol) was dissolved by THF (150 ml). The mixture was cooled into −78° C., and n-butyllithium (2.5M in hexane, 7.83 mL, 19.56 mmol) was slowly added. After 2 hrs, 2-bromo-9H-fluoren-9-one (5.07 g, 19.56 mmol) was added into the mixture. After 3 hrs, the reaction was finished by adding distilled water, and the mixture was extracted by MC. The water in the mixture was dried by $MgSO_4$, and the solution in the mixture was removed. The mixture was precipitated by ethanol, and the solid was filtered. The solid was dissolved by acetic acid (100 ml), and HCl was added. The mixture was refluxed and stirred for 6 hrs and cooled into the room temperature. The solid was filtered and washed by ethanol. After the solid was dried, the solid was columned by MC and hexane (volume ratio=1:4) to obtain the compound C-1. (4.10 g, yield=52.00%)

(2) Compound 1-30

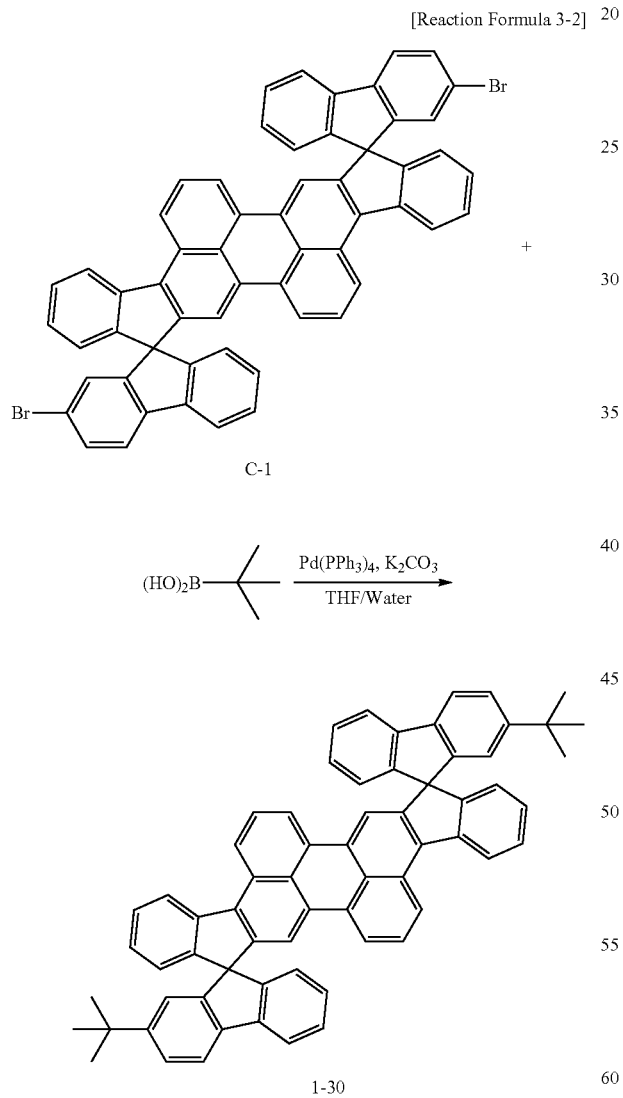

[Reaction Formula 3-2]

In a 2-neck flask (250 ml), the compound C-1 (2.00 g, 2.26 mmol), tert-butylboronic acid (0.53 g, 5.19 mmol), $K_2CO_3$ (1.56 g, 11.28 mmol) and $Pd(PPh_3)_4$ (0.08 g, 0.07 mmol) were dissolved by a mixed solution of THF and water (volume ratio=3:1, 120 ml). The mixture was refluxed and stirred for 12 hrs. After completion of reaction, the mixture was columned by MC and hexane (volume ratio=2:3) to obtain the compound 1-30. (1.10 g, yield=57.98%)

4. Synthesis of Compound 1-34

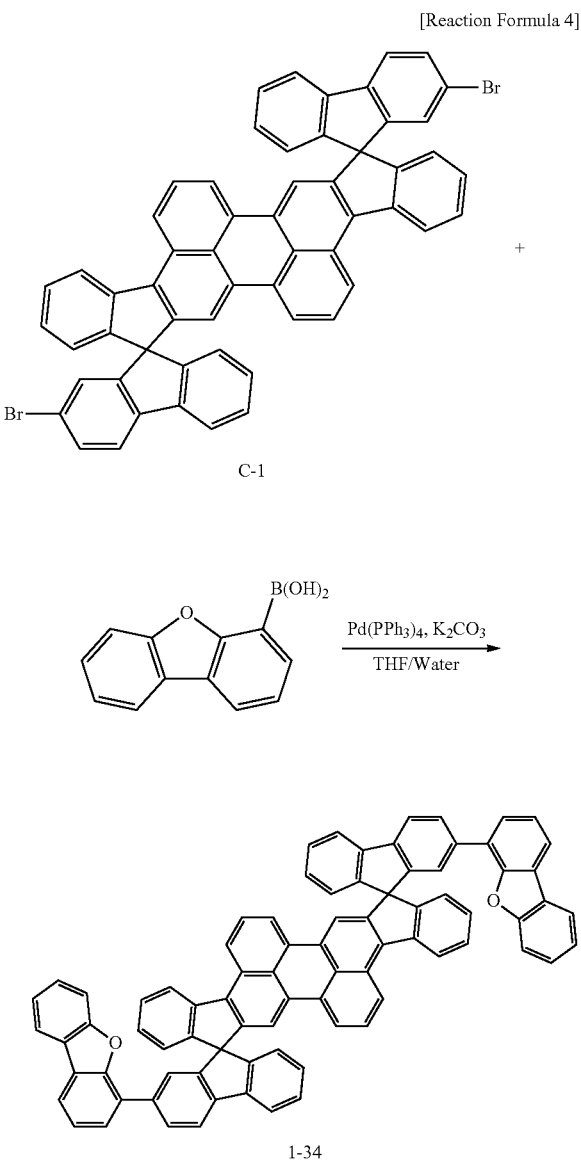

[Reaction Formula 4]

In a 2-neck flask (250 ml), the compound C-1 (2.00 g, 2.26 mmol), dibenzo[b,d]furan-4-ylboronic acid (1.10 g, 5.19 mmol), $K_2CO_3$ (1.56 g, 11.28 mmol), and $Pd(PPh_3)_4$ (0.08 g, 0.07 mmol) were dissolved by a mixed solution of THF and water (volume ratio=3:1, 120 ml). The mixture was refluxed and stirred for 12 hrs. After completion of reaction, the mixture was columned by MC and hexane (volume ratio=2:3) to obtain the compound 1-34. (0.90 g, yield=37.60%)

The EML 240 may further include a host. Namely, the organic compound of the present disclosure is used as a dopant and may have a wt % of about 0.1 to 10 in the EML 240.

For example, the host may be one of compounds in Formula 4.

[Formula 4]

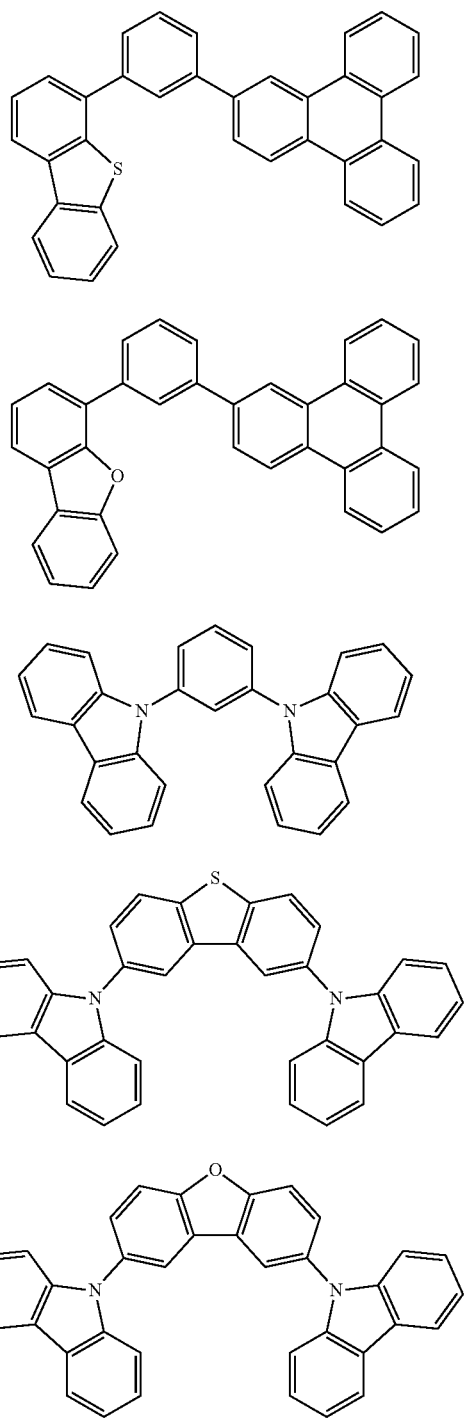

240, a wt % summation of the organic compound of the present disclosure and the delayed fluorescent compound may be about 10.1 to 60.

For example, the delayed fluorescent compound as the second dopant may be one of compounds in Formula 5.

[Formula 5]

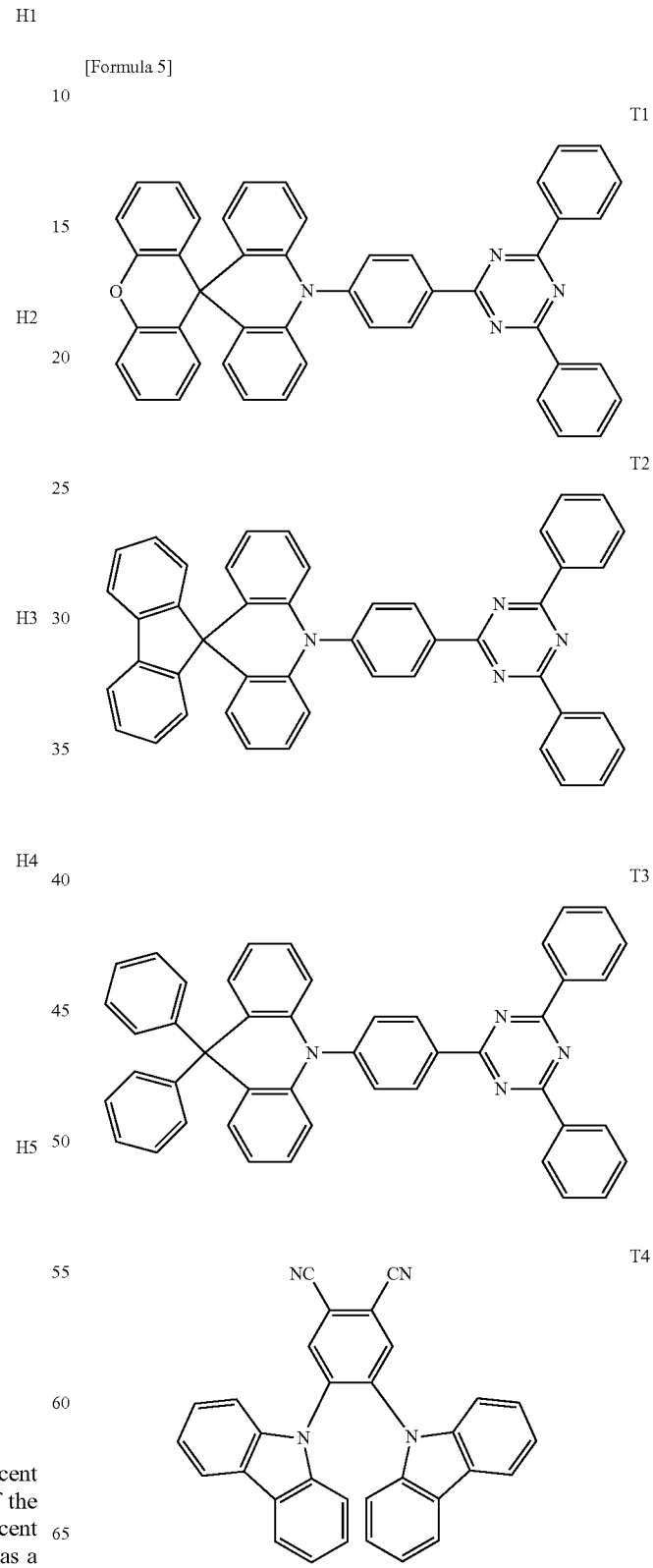

The EML 240 may further include a delayed fluorescent compound. In the EML 240, the organic compound of the present disclosure serves as a first dopant (a fluorescent dopant), and the delayed fluorescent compound serves as a second dopant (a delayed fluorescent dopant). In the EML

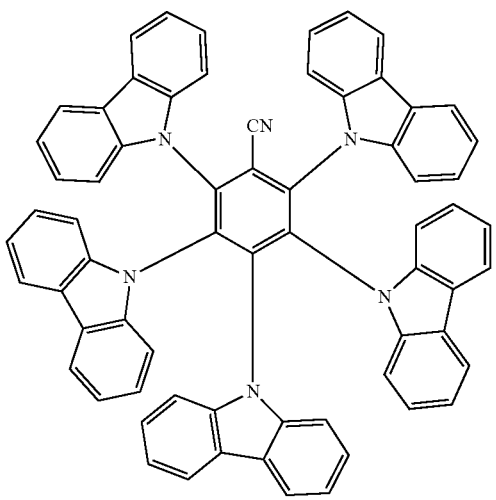

T5

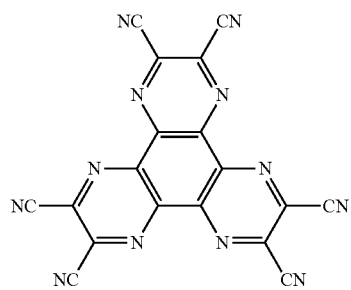

[Formula 6]

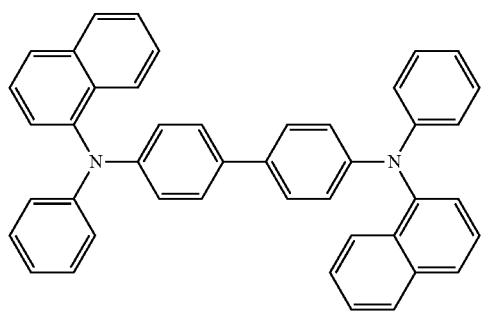

[Formula 7]

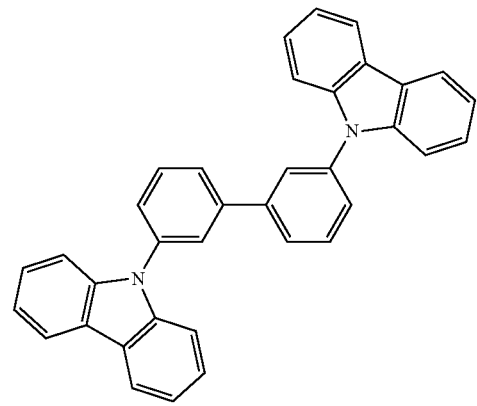

[Formula 8]

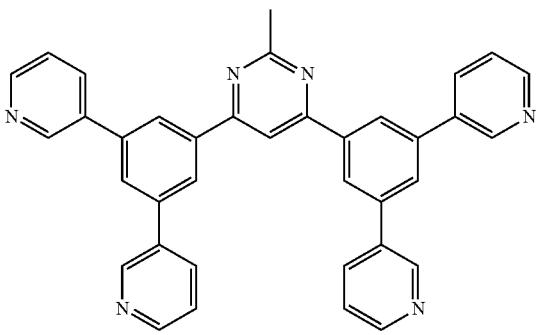

[Formula 9]

The weight ratio of the delayed fluorescent dopant may be greater than that of the fluorescent dopant.

In the delayed fluorescent compound, the difference between the triplet energy of and the singlet energy is less than 0.3 eV such that the triplet energy of is converted into the singlet energy by the reverse intersystem crossing (RISC) effect. Namely, in the delayed fluorescent compound, the triplet exciton is activated by a field or heat and up-converted to the singlet exciton. As a result, the single exciton and the triplet exciton of the delayed fluorescent compound are involved in the emission.

When the EML 240 includes the host, the organic compound of the present disclosure as the fluorescent dopant and the delayed fluorescent dopant, the exciton of the host is transferred into the delayed fluorescent dopant such that the emission occurs from the delayed fluorescent dopant. The light emitted from the delayed fluorescent dopant is absorbed by the fluorescent dopant. Namely, a main absorption wavelength range of the fluorescent dopant may be partially or completely overlap a main emission wavelength range of the delayed fluorescent dopant. Accordingly, the emission is finally generated from the fluorescent dopant.

Namely, since both the single exciton and the triplet exciton of the delayed fluorescent compound are involved in the emission, the emitting efficiency of the organic light emitting diode is improved. In addition, since the fluorescent dopant emits the light by absorbing the light from the delayed fluorescent dopant, the color purity of the light emitted from the EML 240 is improved.

The singlet energy of the delayed fluorescent dopant is greater (higher) than that of the fluorescent dopant. The singlet energy of the host is greater than that of the delayed fluorescent dopant. The triplet energy of the delayed fluorescent dopant is smaller than that of the host and greater than that of the fluorescent dopant.

[Organic Light Emitting Diode]

On an anode (ITO), an HIL (HATCN (Formula 6), 7 nm), an HTL (NPB (Formula 7), 55 nm), an EBL (m-CBP (Formula 8), 10 nm), an EML (35 nm), an HBL (B3PYMPM (Formula 9), 10 nm), an ETL (TPBi (Formula 10), 20 nm), an EIL (LiF), and a cathode (Al) are sequentially stacked.

[Formula 10]

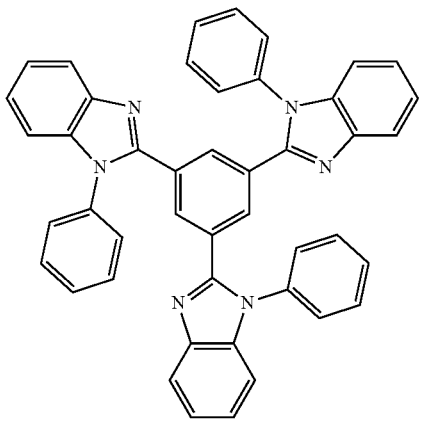

(1) Comparative Example 1 (Ref1)

The compound H1 (65 wt %) of Formula 4 and the compound T1 (35 wt %) of Formula 5 are respectively used as the host and the delayed fluorescent dopant to form the EML.

(2) Comparative Example 2 (Ref2)

The compound H1 (64.5 wt %) of Formula 4, the compound T1 (35 wt %) of Formula 5, and the compound (0.5 wt %) of Formula 11 are respectively used as the host, the delayed fluorescent dopant, and the fluorescent dopant to form the EML.

(3) Example 1 (Ex1)

The compound H1 (64.5 wt %) of Formula 4, the compound T1 (35 wt %) of Formula 5, and the compound 1-1 (0.5 wt %) of Formula 3 are respectively used as the host, the delayed fluorescent dopant, and the fluorescent dopant to form the EML.

(4) Example 2 (Ex2)

The compound H1 (64.5 wt %) of Formula 4, the compound T1 (35 wt %) of Formula 5, and the compound 1-22 (0.5 wt %) of Formula 3 are respectively used as the host, the delayed fluorescent dopant, and the fluorescent dopant to form the EML.

(5) Example 3 (Ex3)

The compound H1 (64.5 wt %) of Formula 4, the compound T1 (35 wt %) of Formula 5, and the compound 1-30 (0.5 wt %) of Formula 3 are respectively used as the host, the delayed fluorescent dopant, and the fluorescent dopant to form the EML.

(6) Example 4 (Ex4)

The compound H1 (64.5 wt %) of Formula 4, the compound T1 (35 wt %) of Formula 5, and the compound 1-34 (0.5 wt %) of Formula 3 are respectively used as the host, the delayed fluorescent dopant, and the fluorescent dopant to form the EML.

[Formula 11]

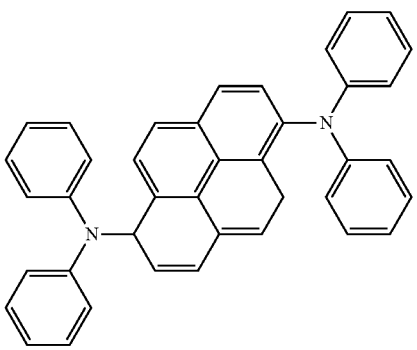

The properties, i.e., the current efficiency (cd/A), the power efficiency (lm/W), the external quantum efficiency (EQE), the CIE color coordinate index and the maximum emission wavelength ($EL_{\lambda max}$), of the organic light emitting diodes of Ref1, Ref2 and Ex1 to Ex4 are measured and listed in Table 1.

TABLE 1

| | cd/A | lm/W | EQE (%) | CIE | $EL_{\lambda max}$ (nm) |
|---|---|---|---|---|---|
| Ref1 | 25.58 | 21.45 | 13.16 | (0.161, 0.293) | 476 |
| Ref2 | 9.9 | 9.9 | 6.5 | (0.148, 0.208) | 470 |
| Ex1 | 25.37 | 20.17 | 14.02 | (0.163, 0.303) | 480 |
| Ex2 | 27.82 | 20.12 | 15.62 | (0.169, 0.308) | 482 |
| Ex3 | 33.6 | 32.0 | 16.6 | (0.167, 0.309) | 483 |
| Ex4 | 26.67 | 19.35 | 14.91 | (0.164, 0.297) | 479 |

As shown in Table 1, the emitting efficiency of the organic light emitting diode of Ex1 to Ex4, each of which includes the delayed fluorescent dopant and the organic compound of the present disclosure as the fluorescent dopant, is significantly improved. Particularly, in comparison to the organic light emitting diode of Ref1, which includes the delayed fluorescent dopant without a fluorescent dopant, the EQE of the organic light emitting diode of Ex1 to Ex4 is increased by 26.1% at a maximum. In comparison to the organic light emitting diode of Ref2, which includes the delayed fluorescent dopant and the fluorescent dopant of Formula 11, the EQE of the organic light emitting diode of Ex1 to Ex4 is increased by 155.4% at a maximum.

In comparison to the organic light emitting diode of Ref2, the current efficiency and the power efficiency of the organic light emitting diode of Ex1 to Ex4 are significantly improved. The current efficiency and the power efficiency of the organic light emitting diode of Ex1 to Ex4 have the same or improved results compared to those of the organic light emitting diode of Ref1.

In comparison to the organic light emitting diode of Ref1, which includes the delayed fluorescent dopant without a fluorescent dopant, the emitting efficiency of the organic light emitting diode of Ref2, which includes the delayed fluorescent dopant and the fluorescent dopant of Formula 11, is significantly decreased. In the emission system with the delayed fluorescent dopant and the fluorescent dopant, the singlet energy and the triplet energy of the delayed fluorescent dopant should be greater than the singlet energy and the triplet energy of the fluorescent dopant, respectively to provide high emitting efficiency. However, the fluorescent dopant and the delayed fluorescent dopant in the organic light emitting diode of Ref2 do not satisfy the above condition.

Namely, in the emission system with the delayed fluorescent dopant and the fluorescent dopant, the energy is transferred from the host into the delayed fluorescent dopant, and the triplet energy of the delayed fluorescent dopant is up-converted into the singlet energy of the delayed fluorescent dopant. The singlet energy of the delayed fluorescent dopant is transferred into the fluorescent dopant. In this case, the quantum efficiency of the organic light emitting diode is increased. However, in the organic light emitting diode of Ref2, the energy transfer from the delayed fluorescent dopant into the fluorescent dopant of Formula 11 is difficult, the emitting efficiency is lowered.

In the organic light emitting diode including the organic compound of the present disclosure, the energy transfer from the delayed fluorescent dopant into the fluorescent dopant efficiently occurs such that the emitting efficiency is increased.

Accordingly, the organic light emitting diode including the organic compound of the present disclosure and having high emitting efficiency is provided. The organic light emitting diode can be used for the OLED device or the lightening device.

Figure 3:
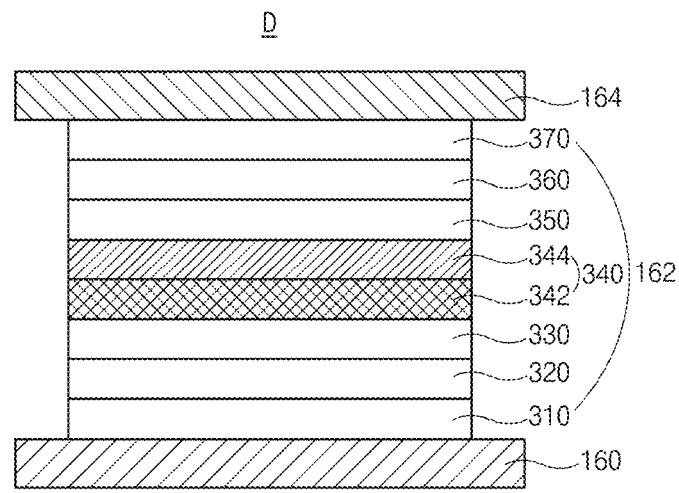
FIG. 3 is a schematic cross-sectional view of an organic light emitting diode according to a third embodiment of the present disclosure.

FIG. 3 is a schematic cross-sectional view of an organic light emitting diode according to a third embodiment of the present disclosure.

As shown in FIG. 3, an organic light emitting diode D includes the first and second electrodes 160 and 164, which face each other, and the organic emitting layer 162 therebetween. The organic emitting layer 162 includes an EML 340 including first and second layers 342 and 344 and being positioned between the first and second electrodes 160 and 164.

The organic emitting layer 162 may further include a HTL 320 between the first electrode 160 and the EML 340 and an ETL 360 between the second electrode 164 and the EML 340.

In addition, the organic emitting layer 162 may further include a HIL 310 between the first electrode 160 and the HTL 320 and an EIL 370 between the second electrode 164 and the ETL 360.

Moreover, the organic emitting layer 162 may further include an EBL 330 between the HTL 320 and the EML 340 and a HBL 350 between the EML 340 and the ETL 360.

The OLED device 100 (of FIG. 1) may include a red pixel region, a green pixel region and a blue pixel region, and the organic light emitting diode D may be positioned in the green pixel region.

For example, the HIL 310 may include at least one compound selected from the group consisting of 4,4',4"-tris (3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB; NPD), 1,4,5,8,9,11-hexaazatriphenylenehexacarbonitrile(dipyrazino[2,3-f:2'3'-h]quinoxaline-2,3,6,7,10,11-hexacarbonitrile; HAT-CN), 1,3,5-tris[4-(diphenylamino) phenyl]benzene (TDAPB), poly(3,4-ethylenedioxythiphene)polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine, but it is not limited thereto.

The HTL 320 may include at least one compound selected from the group consisting of N,N'-diphenyl-N,N'-bis(3-methylphenyl)-1,1'-biphenyl-4,4'-diamine; TPD), NPB (NPD), 4,4'-bis(N-carbazolyl)-1,1'-biphenyl(CBP), poly[N, N'-bis(4-butylpnehyl)-N,N'-bis(phenyl)-benzidine](Poly-TPD), (poly[(9,9-dioctylfluorenyl-2,7-diyl)-co-(4,4'-(N-(4-sec-butylphenyl)diphenylamine))] (TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl)biphenyl-4-amine, but it is not limited thereto.

The ETL 360 may include at least one of an oxadiazole-based compound, a triazole-based compound, a phenanthroline-based compound, a benzoxazole-based compound, a benzothiazole-based compound, a benzimidazole-based compound, and a triazine-based compound. For example, the ETL 260 may include at least one compound selected from the group consisting of tris-(8-hydroxyquinoline aluminum (Alq3), 2-biphenyl-4-yl-5-(4-t-butylphenyl)-1,3,4-oxadiazole (PBD), spiro-PBD, lithium quinolate (Liq), 1,3, 5-tris(N-phenylbenzimidazol-2-yl)benzene (TPBi), bis(2-methyl-8-quinolinolato-N1,O8)-(1,1'-biphenyl-4-olato) aluminum (BAlq), 4,7-diphenyl-1,10-phenanthroline (Bphen), 2,9-bis(naphthalene-2-yl)4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tri(p-pyrid-3-yl-phenyl)benzene (TpPyPB), 2,4,6-tris(3'-(pyridin-3-yl) biphenyl-3-yl)1,3,5-triazine (TmPPPyTz), Poly[9,9-bis(3'-((N,N-dimethyl)-N-ethylammonium)-propyl)-2,7-fluorene]-alt-2,7-(9,9-dioctylfluorene)](PFNBr), tris (phenylquinoxaline (TPQ), and diphenyl-4-triphenylsilyl-phenylphosphine oxide (TSPO1), but it is not limited thereto.

The EIL 370 may include at least one of an alkali halide compound, such as LiF, CsF, NaF, or $BaF_2$, and an organometallic compound, such as Liq, lithium benzoate, or sodium stearate, but it is not limited thereto.

The EBL 330, which is positioned between the HTL 320 and the EML 340 to block the electron transfer from the EML 340 into the HTL 320, may include at least one compound selected from the group consisting of TCTA, tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, MTDATA, 1,3-bis(carbazol-9-yl) benzene (mCP), 3,3'-bis(N-carbazolyl)-1,1'-biphenyl (mCBP), CuPc, N,N'-bis[4-[bis(3-methylphenyl)amino] phenyl]-N,N'-diphenyl-[1,1'-biphenyl]-4,4'-diamine (DNTPD), TDAPB, DCDPA, and 2,8-bis(9-phenyl-9H-carbazol-3-yl)dibenzo[b,d]thiophene), but it is not limited thereto.

The HBL 350, which is positioned between the EML 340 and the ETL 360 to block the hole transfer from the EML 340 into the ETL 360, may include the above material of the ETL 360. For example, the material of the HBL 350 has a HOMO energy level being lower than a material of the EML 240 and may be at least one compound selected from the group consisting of BCP, BAlq, Alq3, PBD, spiro-PBD, Liq, bis-4,6-(3,5-di-3-pyridylphenyl)-2-methylpyrimidine (B3PYMPM), bis[2-(diphenylphosphino)phenyl]teeth oxide (DPEPO), 9-(6-9H-carbazol-9-yl)pyridine-3-yl)-9H-3,9'-bicarbazole, and TSPO1, but it is not limited thereto.

For example, in the EML 340, one of the first layer 342 (e.g., a first emitting material layer or a lower emitting material layer) and the second layer 344 (e.g., a second emitting material layer or an upper emitting material layer) may include the organic compound of the present disclosure as a first dopant (fluorescent dopant) and a first host, and the other one of the first layer 342 and the second layer 344 may include a delayed fluorescent compound as a second dopant (delayed fluorescent dopant) and a second host. In addition, one of the first layer 342 and the second layer 344, which includes the organic compound of the present disclosure, may further include a delayed fluorescent compound as a third dopant.

Each of the second and third dopants as the delayed fluorescent compound is selected from the compounds in Formula 5. The second and third dopants may be same or different.

Each of the first and second hosts may be selected from the compounds in Formula 4, but it is not limited thereto. The first and second hosts may be same or different.

The organic light emitting diode, where the first layer 342 includes the fluorescent dopant and the first host, will be explained.

The fluorescent dopant may have a weight % of about 0.1 to 10 in the first layer 342, and the delayed fluorescent dopant may have a weight % of about 10 to 50 in the second layer 344.

In the organic light emitting diode D, the light from the delayed fluorescent dopant, which has high quantum efficiency, in the second layer 344 is absorbed by the fluorescent dopant in the first layer 342. Then, the fluorescent dopant in the first layer 342 provides the light emission.

Accordingly, the organic light emitting diode D has high emitting efficiency and excellent color purity.

For example, the first host of the first layer 342 may be same as a material of the EBL 330. In this instance, the first layer 342 may have an electron blocking function with an emission function. Namely, the first layer 342 may serve as a buffer layer for blocking the electron. When the EBL 330 is omitted, the first layer 342 serves as an emitting layer and an electron blocking layer.

When the first layer 342 includes the delayed fluorescent dopant and the second layer 344 includes the fluorescent dopant of the organic compound of the present disclosure, the second host in the second layer 344 may be same as a material of the HBL 350. In this instance, the second layer 344 may have a hole blocking function with an emission function. Namely, the second layer 344 may serve as a buffer layer for blocking the hole. When the HBL 350 is omitted, the second layer 344 serves as an emitting layer and a hole blocking layer.

Figure 4:
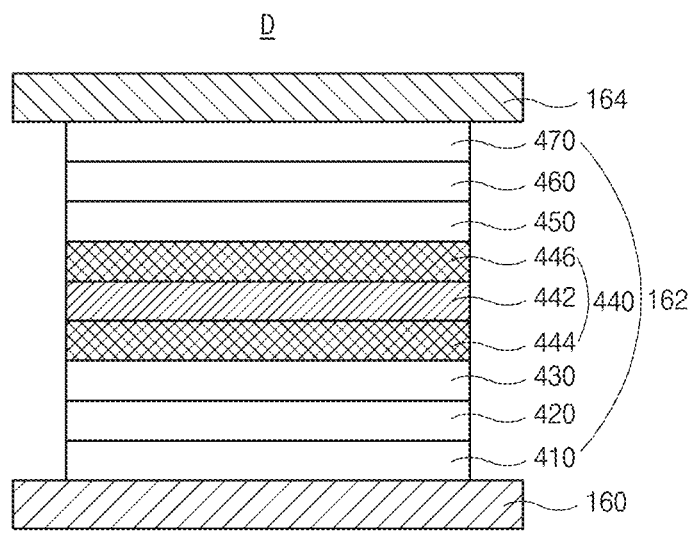
FIG. 4 is a schematic cross-sectional view of an organic light emitting diode according to a fourth embodiment of the present disclosure.

FIG. 4 is a schematic cross-sectional view of an organic light emitting diode according to a fourth embodiment of the present disclosure.

As shown in FIG. 4, an organic light emitting diode D includes the first and second electrodes 160 and 164, which face each other, and the organic emitting layer 162 therebetween. The organic emitting layer 162 includes an EML 440 including first to third layers 442, 444 and 446 and being positioned between the first and second electrodes 160 and 164.

The organic emitting layer 162 may further include a HTL 420 between the first electrode 160 and the EML 440 and an ETL 460 between the second electrode 164 and the EML 440.

In addition, the organic emitting layer 162 may further include a HIL 410 between the first electrode 160 and the HTL 420 and an EIL 470 between the second electrode 164 and the ETL 460.

Moreover, the organic emitting layer 162 may further include an EBL 430 between the HTL 420 and the EML 440 and a HBL 450 between the EML 440 and the ETL 460.

The OLED device 100 (of FIG. 1) may include a red pixel region, a green pixel region and a blue pixel region, and the organic light emitting diode D may be positioned in the green pixel region.

In the EML 440, the first layer 442 (an intermediate emitting material layer) is positioned between the second layer 444 (a lower emitting material layer) and the third layer 446 (an upper emitting material layer). Namely, the second layer 444 is positioned between the EBL 430 and the first layer 442, and the third layer 446 is positioned between the first layer 442 and the HBL 450.

The first layer 442 (e.g., a first emitting material layer) may include a delayed fluorescent compound as a first dopant (delayed fluorescent dopant) and a first host, and the second layer 344 (e.g., a second emitting material layer) may include the organic compound of the present disclosure as a second dopant (first fluorescent dopant) and a second host. The third layer 446 (e.g., a third emitting material layer) may include the organic compound of the present disclosure as a third dopant (second fluorescent dopant) and a third host. Namely, the first layer 442 includes the delayed fluorescent dopant, and each of the second and third layers 444 and 446 at both sides of the first layer 442 includes the fluorescent dopant.

Each of the second and third layers 444 and 446 may further include a delayed fluorescent compound as a fourth dopant and a fifth dopant.

The second and third dopants may be same or different. The delayed fluorescent compounds as the first, fourth and fifth dopants are selected from the compounds in Formula 5 and may be same or different.

Each of the first to third hosts may be selected from the compounds in Formula 4, but it is not limited thereto. The first to third hosts may be same or different.

The delayed fluorescent dopant may have a weight % of about 10 to 50 in the first layer 442, and the first and second fluorescent dopant may have a weight % of about 0.1 to 10 in the second and third layers 444 and 446, respectively.

In the organic light emitting diode D, the light from the delayed fluorescent dopant, which has high quantum efficiency, in the first layer 444 is absorbed by the first and second fluorescent dopants in the second and third layers 444 and 446. Then, the first and second fluorescent dopants in the second and third layers 444 and 446 provide the light emission.

Accordingly, the organic light emitting diode D has high emitting efficiency and excellent color purity.

For example, the second host in the second layer 444 may be same as a material of the EBL 430. In this instance, the second layer 444 may have an electron blocking function with an emission function. Namely, the second layer 444 may serve as a buffer layer for blocking the electron. When the EBL 430 is omitted, the second layer 444 serves as an emitting layer and an electron blocking layer.

The third host in the third layer 446 may be same as a material of the HBL 450. In this instance, the third layer 446 may have a hole blocking function with an emission function. Namely, the third layer 446 may serve as a buffer layer for blocking the hole. When the HBL 450 is omitted, the third layer 446 serves as an emitting layer and a hole blocking layer.

The second host in the second layer 444 may be same as a material of the EBL 430, and the third host in the third layer 446 may be same as a material of the HBL 450. In this instance, the second layer 444 may have an electron blocking function with an emission function, and the third layer 446 may have a hole blocking function with an emission function. Namely, the second layer 444 may serve as a buffer layer for blocking the electron, and the third layer 446 may serve as a buffer layer for blocking the hole. When the EBL 430 and the HBL 450 are omitted, the second layer 444 serves as an emitting layer and an electron blocking layer and the third layer 446 serves as an emitting layer and a hole blocking layer.

Figure 5:
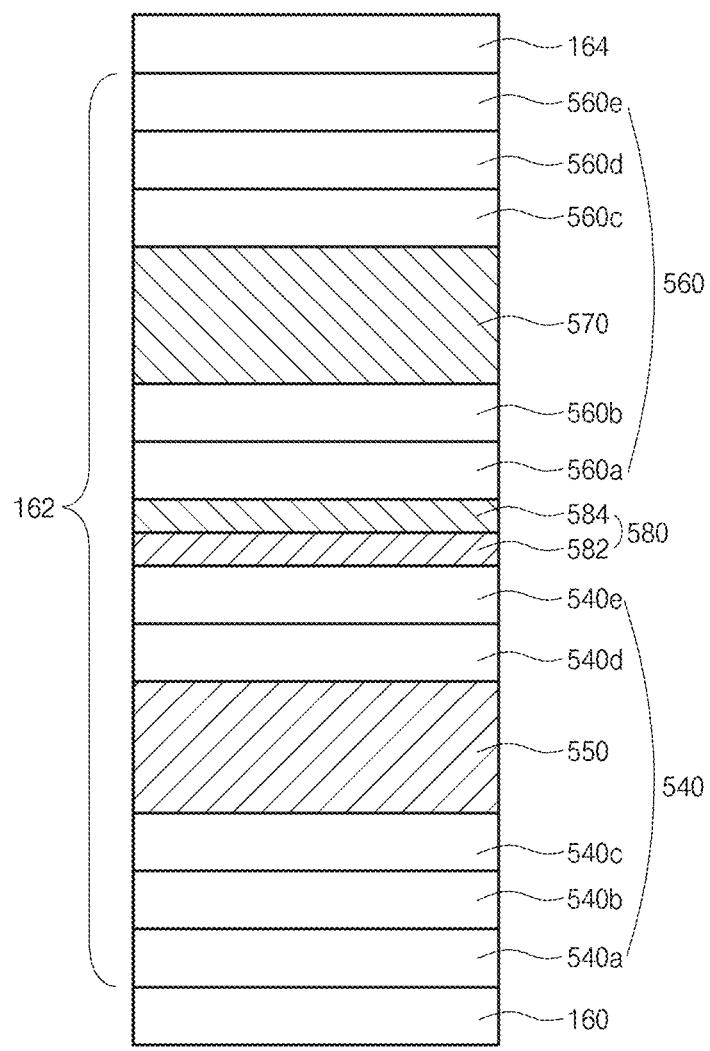
FIG. 5 is a schematic cross-sectional view of an organic light emitting diode according to a fifth embodiment of the present disclosure.

FIG. 5 is a schematic cross-sectional view of an organic light emitting diode according to a fifth embodiment of the present disclosure.

As shown in FIG. 5, the organic light emitting diode D includes the first and second electrodes 160 and 164, which face each other, and the organic emitting layer 162 therebetween. The OLED device 100 (of FIG. 1) may include a red pixel region, a green pixel region and a blue pixel region, and the organic light emitting diode D may be positioned in the green pixel region.

The first electrode 160 may be an anode, and the second electrode 164 may be a cathode.

The organic emitting layer 162 includes a first emitting part 540 including a first EML 550 and a second emitting part 560 including a second EML 570. In addition, the organic emitting layer 162 may further include a charge generation layer (CGL) 580 between the first and second emitting parts 540 and 560.

The CGL 580 is positioned between the first and second emitting parts 540 and 560 such that the first emitting part 540, the CGL 580 and the second emitting part 560 are sequentially stacked on the first electrode 160. Namely, the first emitting part 540 is positioned between the first electrode 160 and the CGL 580, and the second emitting part 580 is positioned between the second electrode 164 and the CGL 580.

The first emitting part 540 includes the first EML 550.

In addition, the first emitting part 540 may further include at least one of a first HTL 540b between the first electrode 160 and the first EML 550, an HIL 540a between the first electrode 160 and the first HTL 540b, and a first ETL 540e between the first EML 550 and the CGL 580.

Moreover, the first emitting part 540 may further include at least one of a first EBL 540c between the first HTL 540b and the first EML 550 and a first HBL 540d between the first EML 550 and the first ETL 540e.

The second emitting part 560 includes the second EML 570.

In addition, the second emitting part 560 may further include at least one of a second HTL 560a between the CGL 580 and the second EML 570, a second ETL 560d between the second EML 570 and the second electrode 164, and an EIL 560e between the second ETL 560d and the second electrode 164.

Moreover, the second emitting part 560 may further include at least one of a second EBL 560b between the second HTL 560a and the second EML 570 and a second HBL 560c between the second EML 570 and the second ETL 560d.

The CGL 580 is positioned between the first and second emitting parts 540 and 560. Namely, the first and second emitting parts 540 and 560 is connected to each other through the CGL 580. The CGL 580 may be a P-N junction type CGL of an N-type CGL 582 and a P-type CGL 584.

The N-type CGL 582 is positioned between the first ETL 540e and the second HTL 560a, and the P-type CGL 584 is positioned between the N-type CGL 582 and the second HTL 560a. The N-type CGL 582 provides an electron into the first EML 550 of the first emitting part 540, and the P-type CGL 584 provides a hole into the second EML 570 of the second emitting part 560.

The first and second EMLs 550 and 570 are a green EML. At least one of the first and second EMLs 550 and 570 includes the organic compound of Formula 1. For example, the first EML 550 may include the organic compound of Formula 1. The first EML 550 may further include a host. For example, the host may be one of the compounds in Formula 3. In the first EML 550, the organic compound acts as a dopant (emitter) and may have a weight % of about 0.1 to 10.

In addition, the first EML 550 may further include a delayed fluorescent compound. For example, the delayed fluorescent compound may be one of the compounds in Formula 5.

The second EML 570 may include the organic compound of Formula 1. Namely, the second EML 570 may have the same organic compound as the first EML 550. Alternatively, the second EML 570 may include a compound being different from the organic compound in the first EML 550 such that the first and second EMLs 550 and 570 have a different in an emitted-light wavelength or an emitting efficiency.

Figure 6:
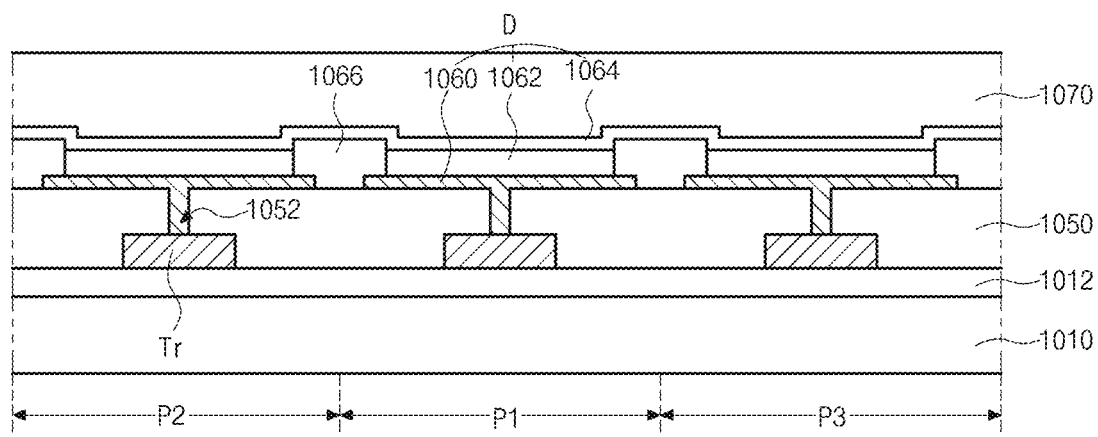
FIG. 6 is a schematic cross-sectional view of an OLED device according to a sixth embodiment of the present disclosure.

FIG. 6 is a schematic cross-sectional view of an OLED device according to a sixth embodiment of the present disclosure.

As shown in FIG. 6, the OLED device 1000 includes a substrate 1010, wherein first to third pixel regions P1, P2 and P3 are defined, a TFT Tr over the substrate 1010 and an organic light emitting diode D. The organic light emitting diode D is disposed over the TFT Tr and is connected to the TFT Tr. For example, the first to third pixel regions P1, P2 and P3 may be a green pixel region, a red pixel region and a blue pixel region, respectively.

The substrate 1010 may be a glass substrate or a plastic substrate. For example, the substrate 1010 may be a polyimide substrate.

A buffer layer 1012 is formed on the substrate 1010, and the TFT Tr is formed on the buffer layer 1012. The buffer layer 1012 may be omitted.

As explained with FIG. 1, the TFT Tr may include a semiconductor layer, a gate electrode, a source electrode and a drain electrode and may serve as a driving element.

A planarization layer (or passivation layer) 1050 is formed on the TFT Tr. The planarization layer 1050 has a flat top surface and includes a drain contact hole 1052 exposing the drain electrode of the TFT Tr.

The organic light emitting diode D is disposed on the planarization layer 1050 and includes a first electrode 1060, an organic emitting layer 1062 and a second electrode 1064. The first electrode 1060 is connected to the drain electrode of the TFT Tr, and the organic emitting layer 1062 and the second electrode 1064 are sequentially stacked on the first electrode 1060. The organic light emitting diode D is disposed in each of the first to third pixel regions P1 to P3 and emits different color light in the first to third pixel regions P1 to P3. For example, the organic light emitting diode D in the first pixel region P1 may emit the green light, the organic light emitting diode D in the second pixel region P2 may emit the red light, and the organic light emitting diode D in the third pixel region P3 may emit the blue light.

The first electrode 1060 is formed to be separate in the first to third pixel regions P1 to P3, and the second electrode 1064 is formed as one-body to cover the first to third pixel regions P1 to P3.

The first electrode 1060 is one of an anode and a cathode, and the second electrode 1064 is the other one of the anode and the cathode. In addition, one of the first and second electrodes 1060 and 1064 may be a light transmitting electrode (or a semi-transmitting electrode), and the other one of the first and second electrodes 1060 and 1064 may be a reflecting electrode.

For example, the first electrode 1060 may be the anode and may include a transparent conductive oxide material layer formed of a transparent conductive oxide (TCO) material having a relatively high work function. The second electrode 1064 may be the cathode and may include a metallic material layer formed of a low resistance metallic material having a relatively low work function. For example, the transparent conductive oxide material layer of the first electrode 1060 include at least one of indium-tin-oxide (ITO), indium-zinc-oxide (IZO), indium-tin-zinc oxide (ITZO), tin oxide (SnO), zinc oxide (ZnO), indium-copper-oxide (ICO) and aluminum-zinc oxide alloy (Al:ZnO), and the second electrode 1064 may include Al, Mg, Ca, Ag, their alloy, e.g., Mg—Ag alloy, or their combination.

In the bottom-emission type OLED device 1000, the first electrode 1060 may have a single-layered structure of the transparent conductive oxide material layer.

On the other hand, in the top-emission type OLED device 1000, a reflection electrode or a reflection layer may be formed under the first electrode 1060. For example, the reflection electrode or the reflection layer may be formed of Ag or aluminum-palladium-copper (APC) alloy. In this instance, the first electrode 1060 may have a triple-layered structure of ITO/Ag/ITO or ITO/APC/ITO. In addition, the second electrode 1064 may have a thin profile (small thickness) to provide a light transmittance property (or a semi-transmittance property).

A bank layer 1066 is formed on the planarization layer 1050 to cover an edge of the first electrode 1060. Namely, the bank layer 1066 is positioned at a boundary of the first to third pixel regions P1 to P3 and exposes a center of the first electrode 1060 in the first to third pixel regions P1 to P3.

The organic emitting layer 1062 as an emitting unit is formed on the first electrode 1060. The organic emitting layer 1062 may have a single-layered structure of an EML. Alternatively, the organic emitting layer 1062 may further include at least one of an HIL, an HTL, an EBL, which are sequentially stacked between the first electrode 1060 and the EML, an HBL, an ETL and an EIL, which are sequentially stacked between the EML and the second electrode 1064.

As mentioned above, in the first pixel region P1 being the green pixel region, the EML of the organic emitting layer 1062 includes the organic compound of Formula 1. In addition, the EML of the organic emitting layer 1062 may further include a host. Moreover, the EML of the organic emitting layer 1062 may further include a delayed fluorescent compound. In this instance, the host may be a compound of Formula 4, and the delayed fluorescent compound may be a compound of Formula 5.

An encapsulation film 1070 is formed on the second electrode 1064 to prevent penetration of moisture into the organic light emitting diode D. The encapsulation film 1070 may have a triple-layered structure including a first inorganic insulating layer, an organic insulating layer and a second inorganic insulating layer, but it is not limited thereto.

The OLED device 1000 may further include a polarization plate (not shown) for reducing an ambient light reflection. For example, the polarization plate may be a circular polarization plate. In the bottom-emission type OLED device 1000, the polarization plate may be disposed under the substrate 1010. In the top-emission type OLED device 1000, the polarization plate may be disposed on or over the encapsulation film 1070.

Figure 7:
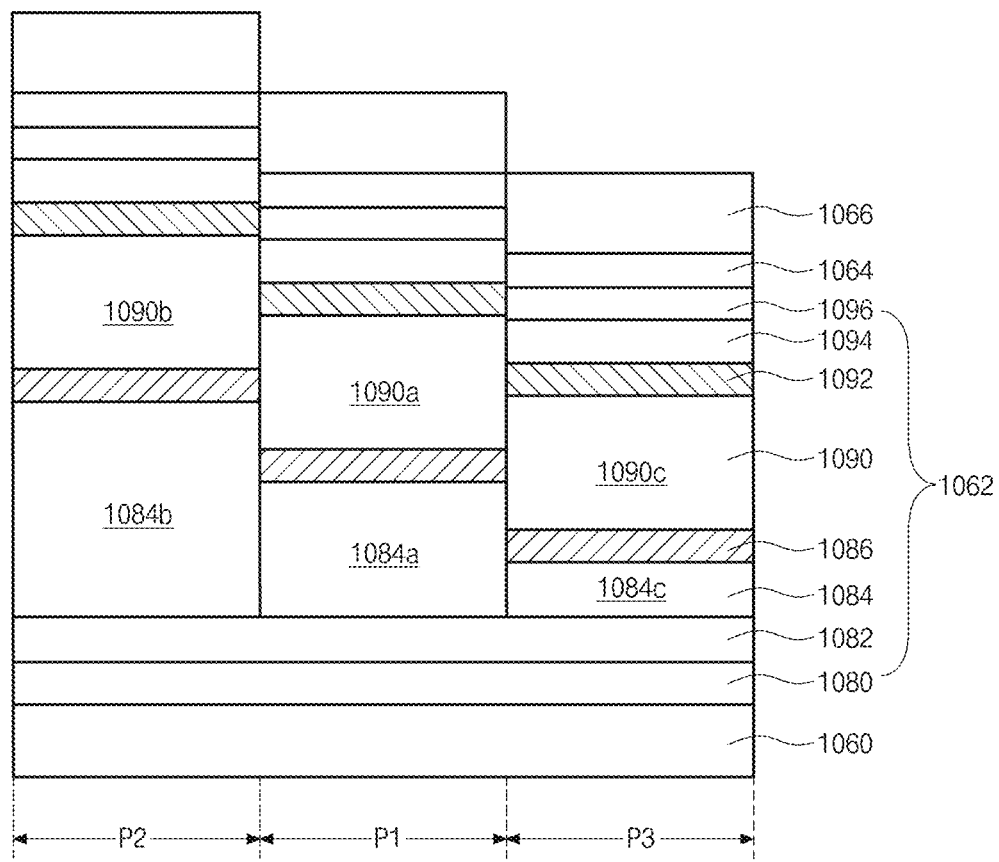
FIG. 7 is a schematic cross-sectional view of an organic light emitting diode according to a seventh embodiment of the present disclosure.

FIG. 7 is a schematic cross-sectional view of an organic light emitting diode according to a seventh embodiment of the present disclosure.

As shown in FIG. 7, the organic light emitting diode D is positioned in each of first to third pixel regions P1 to P3 and includes the first and second electrodes 1060 and 1064, which face each other, and the organic emitting layer 1062 therebetween. The organic emitting layer 1062 includes an EML 1092.

The first electrode 1060 may be an anode, and the second electrode 1064 may be a cathode. For example, the first electrode 1060 may be a reflective electrode, and the second electrode 1064 may be a transmitting electrode (or a semi-transmitting electrode).

The organic emitting layer 1062 may further include an HTL 1082 between the first electrode 1060 and the EML 1090 and an ETL 1094 between the EML 1090 and the second electrode 1064.

In addition, the organic emitting layer 1062 may further include an HIL 1080 between the first electrode 1060 and the HTL 1082 and an EIL 1096 between the ETL 1094 and the second electrode 1064.

Moreover, the organic emitting layer 1062 may further include an EBL 1086 between the EML 1090 and the HTL 1082 and an HBL 1092 between the EML 1090 and the ETL 1094.

Furthermore, the organic emitting layer 1062 may further include an auxiliary HTL 1084 between the HTL 1082 and the EBL 1086. The auxiliary HTL 1084 may include a first auxiliary HTL 1084a in the first pixel region P1, a second auxiliary HTL 1084b in the second pixel region P2 and a third auxiliary HTL 1084c in the third pixel region P3.

The first auxiliary HTL 1084a has a first thickness, the second auxiliary HTL 1084b has a second thickness, and the third auxiliary HTL 1084c has a third thickness. The first thickness is smaller than the second thickness and greater than the third thickness such that the organic light emitting diode D provides a micro-cavity structure.

Namely, by the first to third auxiliary HTLs 1084a, 1084b and 1084c having a difference in a thickness, a distance between the first and second electrodes 1060 and 1064 in the first pixel region P1, in which a first wavelength range light, e.g., green light, is emitted, is smaller than a distance between the first and second electrodes 1060 and 1064 in the second pixel region P2, in which a second wavelength range light, e.g., red light, being greater than the first wavelength range is emitted, and is greater than a distance between the first and second electrodes 1060 and 1064 in the third pixel region P3, in which a third wavelength range light, e.g., blue light, being smaller than the first wavelength range is emitted. Accordingly, the emitting efficiency of the organic light emitting diode D is improved.

In FIG. 7, the third auxiliary HTL 1084c is formed in the third pixel region P3. Alternatively, a micro-cavity structure may be provided without the third auxiliary HTL 1084c.

A capping layer (not shown) for improving a light-extracting property may be further formed on the second electrode 1084.

The EML 1090 includes a first EML 1090a in the first pixel region P1, a second EML 1090b in the second pixel region P2 and a third EML 1090c in the third pixel region P3. The first to third EMLs 1090a, 1090b and 1090c may be a green EML, a red EML and a blue EML, respectively.

The first EML 1090a in the first pixel region P1 includes the organic compound of Formula 1. In addition, the first EML 1090a may further include a host. The host may be a compound of Formula 4. In the first EML 1090a, the organic compound may serve as a dopant and may have a weight % of about 0.1 to 10.

Moreover, the first EML 1090a may further include a delayed fluorescent compound. The delayed fluorescent compound may be a compound of Formula 5.

Each of the second EML 1090b in the second pixel region P2 and the third EML 1090c in the third pixel region P3 may include a host and a dopant. For example, in each of the second EML 1090b in the second pixel region P2 and the third EML 1090c in the third pixel region P3, the dopant may include at least one of a phosphorescent compound, a fluorescent compound and a delayed fluorescent compound.

The organic light emitting diode D in FIG. 7 respectively emits the green light, the red light and the blue light in the first to third pixel regions P1 to P3 such that the OLED device 1000 (of FIG. 6) can provide a full-color image.

The OLED device 1000 may further include a color filter layer corresponding to the first to third pixel regions P1 to P3 to improve a color purity. For example, the color filter layer may include a first color filter layer, e.g., a green color filter layer, corresponding to the first pixel region P1, a second color filter layer, e.g., a red color filter layer, corresponding to the second pixel region P2, and a third color filter layer, e.g., a blue color filter layer, corresponding to the third pixel region P3.

In the bottom-emission type OLED device 1000, the color filter layer may be disposed between the organic light emitting diode D and the substrate 1010. On the other hand, in the top-emission type OLED device 1000, the color filter layer may be disposed on or over the organic light emitting diode D.

Figure 8:
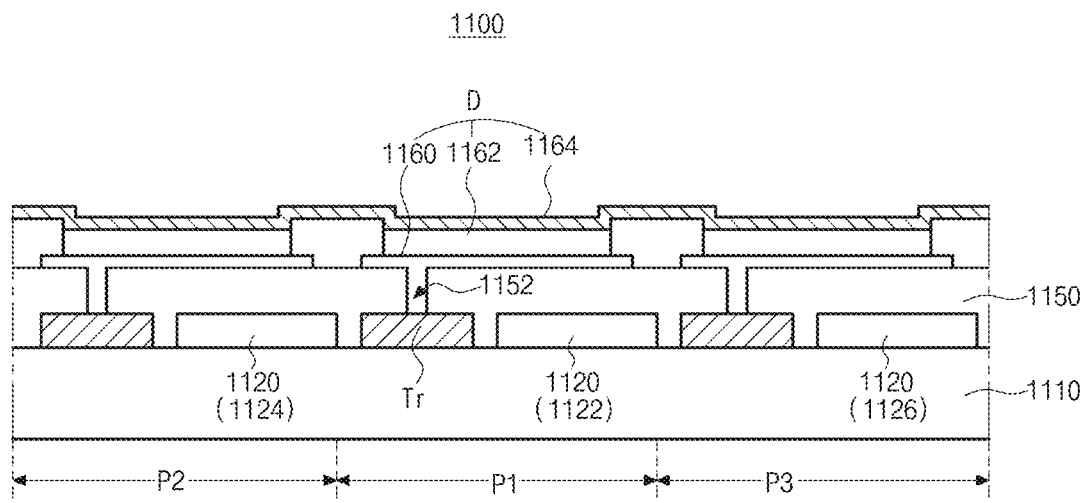
FIG. 8 is a schematic cross-sectional view of an OLED device according to an eighth embodiment of the present disclosure.

FIG. 8 is a schematic cross-sectional view of an OLED device according to an eighth embodiment of the present disclosure.

As shown in FIG. 8, the OLED device 1100 includes a substrate 1110, wherein first to third pixel regions P1, P2 and P3 are defined, a TFT Tr over the substrate 1110, an organic light emitting diode D, which is disposed over the TFT Tr and is connected to the TFT Tr, and a color filter layer 1120 corresponding to the first to third pixel regions P1 to P3. For example, the first to third pixel regions P1, P2 and P3 may be a green pixel region, a red pixel region and a blue pixel region, respectively.

The substrate 1110 may be a glass substrate or a plastic substrate. For example, the substrate 1110 may be a polyimide substrate.

The TFT Tr is formed on the substrate 1110. Alternatively, a buffer layer (not shown) may be formed on the substrate 1110, and the TFT Tr may be formed on the buffer layer.

As explained with FIG. 1, the TFT Tr may include a semiconductor layer, a gate electrode, a source electrode and a drain electrode and may serve as a driving element.

In addition, the color filter layer 1120 is disposed on the substrate 1110. For example, the color filter layer 1120 may include a first color filter layer 1122 corresponding to the first pixel region P1, a second color filter layer 1124 corresponding to the second pixel region P2, and a third color filter layer 1126 corresponding to the third pixel region P3. The first to third color filter layers 1122, 1124 and 1126 may be a green color filter layer, a red color filter layer and a blue color filter layer, respectively. For example, the first color filter layer 1122 may include at least one of a green dye and a green pigment, and the second color filter layer 1124 may include at least one of a red dye and a red pigment. The third color filter layer 1126 may include at least one of a blue dye and a blue pigment.

A planarization layer (or passivation layer) 1150 is formed on the TFT Tr and the color filter layer 1120. The planarization layer 1150 has a flat top surface and includes a drain contact hole 1152 exposing the drain electrode of the TFT Tr.

The organic light emitting diode D is disposed on the planarization layer 1150 and corresponds to the color filter layer 1120. The organic light emitting diode D includes a first electrode 1160, an organic emitting layer 1162 and a second electrode 1164. The first electrode 1160 is connected to the drain electrode of the TFT Tr, and the organic emitting layer 1162 and the second electrode 1164 are sequentially stacked on the first electrode 1160. The organic light emitting diode D emits the white light in each of the first to third pixel regions P1 to P3.

The first electrode 1160 is formed to be separate in the first to third pixel regions P1 to P3, and the second electrode 1164 is formed as one-body to cover the first to third pixel regions P1 to P3.

The first electrode 1160 is one of an anode and a cathode, and the second electrode 1164 is the other one of the anode and the cathode. In addition, the first electrode 1160 may be a light transmitting electrode (or a semi-transmitting electrode), and the second electrode 1164 may be a reflecting electrode.

For example, the first electrode 1160 may be the anode and may include a transparent conductive oxide material layer formed of a transparent conductive oxide (TCO) material having a relatively high work function. The second electrode 1164 may be the cathode and may include a metallic material layer formed of a low resistance metallic material having a relatively low work function. For example, the transparent conductive oxide material layer of the first electrode 1160 include at least one of indium-tin-oxide (ITO), indium-zinc-oxide (IZO), indium-tin-zinc oxide (ITZO), tin oxide (SnO), zinc oxide (ZnO), indium-copper-oxide (ICO) and aluminum-zinc oxide alloy (Al:ZnO), and the second electrode 1164 may include Al, Mg, Ca, Ag, their alloy, e.g., Mg—Ag alloy, or their combination.

The organic emitting layer 1162 as an emitting unit is formed on the first electrode 1160. The organic emitting layer 1162 includes at least two emitting parts emitting different color light. Each emitting part may have a single-layered structure of an EML. Alternatively, each emitting part may further include at least one of an HIL, an HTL, an EBL an HBL, an ETL and an EIL. In addition, the organic emitting layer 1162 may further include a charge generation layer (CGL) between the emitting parts.

The EML of one of the emitting parts includes the organic compound of Formula 1. In addition, the EML of one of the emitting parts may further include at least one of a host and a delayed fluorescent compound. In this instance, the host may be a compound of Formula 4, and the delayed fluorescent compound may be a compound of Formula 5.

A bank layer 1166 is formed on the planarization layer 1150 to cover an edge of the first electrode 1160. Namely, the bank layer 1166 is positioned at a boundary of the first to third pixel regions P1 to P3 and exposes a center of the first electrode 1160 in the first to third pixel regions P1 to P3. As mentioned above, since the organic light emitting diode D emits the white light in the first to third pixel regions P1 to P3, the organic emitting layer 1162 may be formed as a common layer in the first to third pixel regions P1 to P3 without separation in the first to third pixel regions P1 to P3.

The bank layer 1166 may be formed to prevent the current leakage at an edge of the first electrode 1160 and may be omitted.

Although not shown, the OLED device 1100 may further include an encapsulation film is formed on the second electrode 1164 to prevent penetration of moisture into the organic light emitting diode D. In addition, the OLED device 1100 may further include a polarization plate under the substrate 1110 for reducing an ambient light reflection.

In the OLED device 1100 of FIG. 8, the first electrode 1160 is a transparent electrode (light transmitting electrode), and the second electrode 1164 is a reflecting electrode. In addition, the color filter layer 1120 is positioned between the substrate 1110 and the organic light emitting diode D. Namely, the OLED device 11000 is a bottom-emission type.

Alternatively, in the OLED device 1100, the first electrode 1160 may be a reflecting electrode, and the second electrode 1154 may be a transparent electrode (or a semi-transparent electrode). In this case, the color filter layer 1120 is positioned on or over the organic light emitting diode D.

In the OLED device 1100, the organic light emitting diode D in the first to third pixel regions P1 to P3 emits the white light, and the white light passes through the first to third color filter layers 1122, 1124 and 1126. Accordingly, the green light, the red light and the blue light are displayed in the first to third pixel regions P1 to P3, respectively.

Although not shown, a color conversion layer may be formed between the organic light emitting diode D and the color filter layer 1120. The color conversion layer may include a green color conversion layer, a red color conversion layer and a blue color conversion layer respectively corresponding to the first to third pixel regions P1 to P3, and the white light from the organic light emitting diode D can be converted into the green light, the red light and the blue light. The color conversion layer may include a quantum dot. Accordingly, the color purity of the organic light emitting diode D may be further improved.

The color conversion layer may be included instead of the color filter layer 1120.

Figure 9:
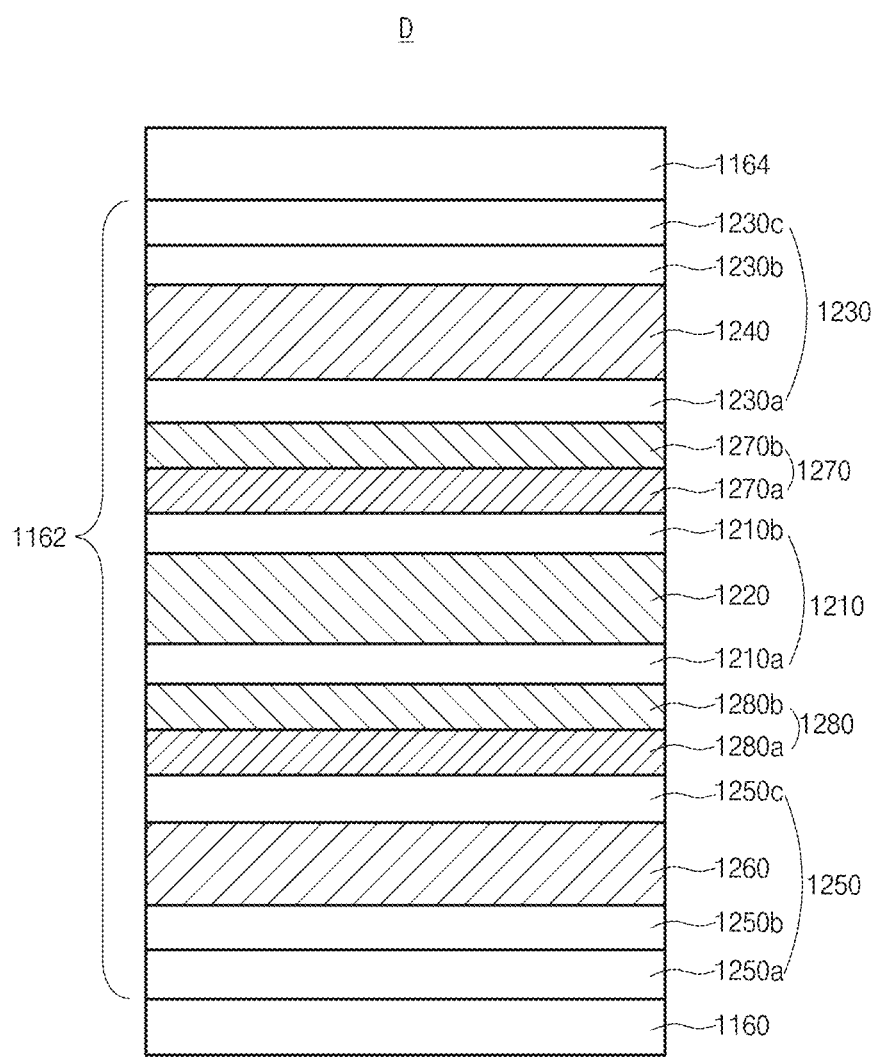
FIG. 9 is a schematic cross-sectional view of an organic light emitting diode according to a ninth embodiment of the present disclosure.

FIG. 9 is a schematic cross-sectional view of an organic light emitting diode according to a ninth embodiment of the present disclosure.

As shown in FIG. 9, the organic light emitting diode D includes the first and second electrodes 1160 and 1164, which face each other, and the organic emitting layer 1162 therebetween.

The first electrode 1160 may be an anode, and the second electrode 1164 may be a cathode. The first electrode 1160 is a transparent electrode (a light transmitting electrode), and the second electrode 1164 is a reflecting electrode.

The organic emitting layer 1162 includes a first emitting part 1210 including a first EML 1220, a second emitting part 1230 including a second EML 1240 and a third emitting part 1250 including a third EML 1260. In addition, the organic emitting layer 1162 may further include a first CGL 1270 between the first and second emitting parts 1210 and 1230 and a second CGL 1280 between the first emitting part 1210 and the third emitting part 1250.

The first CGL 1270 is positioned between the first and second emitting parts 1210 and 1230, and the second CGL 1280 is positioned between the first and third emitting parts 1210 and 1250. Namely, the third emitting part 1250, the second CGL 1280, the first emitting part 1210, the first CGL 1270 and the second emitting part 1230 are sequentially stacked on the first electrode 1160. In other words, the first emitting part 1210 is positioned between the first and second CGLs 1270 and 1280, and the second emitting part 1230 is positioned between the first CGL 1270 and the second electrode 1164. The third emitting part 1250 is positioned between the second CGL 1280 and the first electrode 1160.

The first emitting part 1210 may further include a first HTL 1210a under the first EML 1220 and a first ETL 1210b over the first EML 1220. Namely, the first HTL 1210a may positioned between the first EML 1220 and the second CGL 1270, and the first ETL 1210b may be positioned between the first EML 1220 and the first CGL 1270.

In addition, the first emitting part 1210 may further include an EBL (not shown) between the first HTL 1210a and the first EML 1220 and an HBL (not shown) between the first ETL 1210b and the first EML 1220.

The second emitting part 1230 may further include a second HTL 1230a under the second EML 1240, a second ETL 1230b over the second EML 1240 and an EIL 1230c on the second ETL 1230b. Namely, the second HTL 1230a may be positioned between the second EML 1240 and the first CGL 1270, and the second ETL 1230b and the EIL 1230c may be positioned between the second EML 1240 and the second electrode 1164.

In addition, the second emitting part 1230 may further include an EBL (not shown) between the second HTL 1230a and the second EML 1240 and an HBL (not shown) between the second ETL 1230b and the second EML 1240.

The third emitting part 1250 may further include a third HTL 1250b under the third EML 1260, an HIL 1250a under the third HTL 1250b and a third ETL 1250c over the third EML 1260. Namely, the HIL 1250a and the third HTL 1250b may be positioned between the first electrode 1160 and the third EML 1260, and the third ETL 1250c may be positioned between the third EML 1260 and the second CGL 1280.

In addition, the third emitting part 1250 may further include an EBL (not shown) between the third HTL 1250b and the third EML 1260 and an HBL (not shown) between the third ETL 1250c and the third EML 1260.

One of the first to third EMLs 1220, 1240 and 1260 is a green EML. Another one of the first to third EMLs 1220, 1240 and 1260 may be a blue EML, and the other one of the first to third EMLs 1220, 1240 and 1260 may be a red EML.

For example, the first EML 1220 may be the green EML, the second EML 1240 may be the blue EML, and the third EML 1260 may be the red EML. Alternatively, the first EML 1220 may be the green EML, the second EML 1240 may be the red EML, and the third EML 1260 may be the blue EML.

The first EML 1220 includes the organic compound of Formula 1. The first EML 1220 may further include at least one of a host and a delayed fluorescent compound. The host may be a compound of Formula 4, and the delayed fluorescent compound may be a compound of Formula 5.

The second EML 1240 includes a host and a blue dopant (or a red dopant), and the third EML 1260 includes a host and a red dopant (or a blue dopant). For example, in each of the second and third EMLs 1240a and 1260, the dopant may include at least one of a phosphorescent compound, a fluorescent compound and a delayed fluorescent compound.

The organic light emitting diode D in the first to third pixel regions P1 to P3 (of FIG. 8) emits the white light, and the white light passes through the color filter layer 1120 (of FIG. 8) in the first to third pixel regions P1 to P3. Accordingly, the OLED device 1100 (of FIG. 8) can provide a full-color image.

Figure 10:
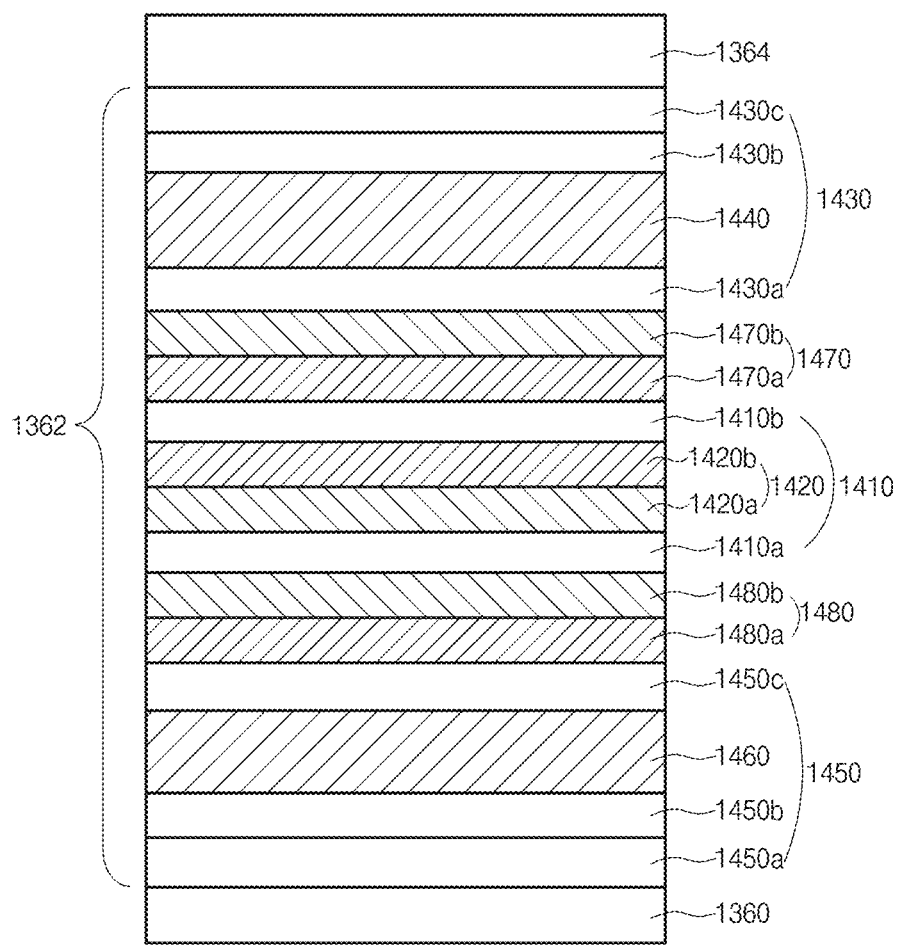
FIG. 10 is a schematic cross-sectional view of an organic light emitting diode according to a tenth embodiment of the present disclosure.

FIG. 10 is a schematic cross-sectional view of an organic light emitting diode according to a tenth embodiment of the present disclosure.

As shown in FIG. 10, the organic light emitting diode D includes the first and second electrodes 1360 and 1364, which face each other, and the organic emitting layer 1362 therebetween.

The first electrode 1360 may be an anode, and the second electrode 1364 may be a cathode. The first electrode 1360 is a transparent electrode (a light transmitting electrode), and the second electrode 1364 is a reflecting electrode.

The organic emitting layer 1362 includes a first emitting part 1410 including a first EML 1420, a second emitting part 1430 including a second EML 1440 and a third emitting part 1450 including a third EML 1460. In addition, the organic emitting layer 1362 may further include a first CGL 1470 between the first and second emitting parts 1410 and 1430 and a second CGL 1480 between the first emitting part 1410 and the third emitting part 1450.

The first emitting part 1420 includes a lower EML 1420a and an upper EML 1420b. Namely, the lower EML 1420a is positioned to be closer to the first electrode 1360, and the upper EML 1420b is positioned to be closer to the second electrode 1364.

The first CGL 1470 is positioned between the first and second emitting parts 1410 and 1430, and the second CGL 1480 is positioned between the first and third emitting parts 1410 and 1450. Namely, the third emitting part 1450, the second CGL 1480, the first emitting part 1410, the first CGL 1470 and the second emitting part 1430 are sequentially stacked on the first electrode 1360. In other words, the first emitting part 1410 is positioned between the first and second CGLs 1470 and 1480, and the second emitting part 1430 is positioned between the first CGL 1470 and the second electrode 1364. The third emitting part 1450 is positioned between the second CGL 1480 and the first electrode 1360.

The first emitting part 1410 may further include a first HTL 1410a under the first EML 1420 and a first ETL 1410b over the first EML 1420. Namely, the first HTL 1410a may positioned between the first EML 1420 and the second CGL 1470, and the first ETL 1410b may be positioned between the first EML 1420 and the first CGL 1470.

In addition, the first emitting part 1410 may further include an EBL (not shown) between the first HTL 1410a and the first EML 1420 and an HBL (not shown) between the first ETL 1410b and the first EML 1420.

The second emitting part 1430 may further include a second HTL 1430a under the second EML 1440, a second ETL 1430b over the second EML 1440 and an EIL 1430c on the second ETL 1430b. Namely, the second HTL 1430a may be positioned between the second EML 1440 and the first CGL 1470, and the second ETL 1430b and the EIL 1430c may be positioned between the second EML 1440 and the second electrode 1364.

In addition, the second emitting part 1430 may further include an EBL (not shown) between the second HTL 1430a and the second EML 1440 and an HBL (not shown) between the second ETL 1430b and the second EML 1440.

The third emitting part 1450 may further include a third HTL 1450b under the third EML 1460, an HIL 1450a under the third HTL 1450b and a third ETL 1450c over the third EML 1460. Namely, the HIL 1450a and the third HTL 1450b may be positioned between the first electrode 1360 and the third EML 1460, and the third ETL 1450c may be positioned between the third EML 1460 and the second CGL 1480.

In addition, the third emitting part 1450 may further include an EBL (not shown) between the third HTL 1450b and the third EML 1460 and an HBL (not shown) between the third ETL 1450c and the third EML 1460.

One of the lower and upper EMLs 1420a and 1420b of the first EML 1420 is a green EML, and the other one of the lower and upper EMLs 1420a and 1420b of the first EML 1420 may be a red EML. Namely, the green EML (or the red EML) and the red EML (or the green EML) are sequentially stacked to form the first EML 1420.

For example, the upper EML 1420b being the green EML includes the organic compound of Formula 1. The upper EML 1420b may further include at least one of a host and a delayed fluorescent compound. The host may be a compound of Formula 4, and the delayed fluorescent compound may be a compound of Formula 5.

The lower EML 1420a being the red EML may include a host and a red dopant.

Each of the second and third EMLs 1440 and 1460 may be a blue EML. Each of the second and third EMLs 1440 and 1460 may include a host and a blue dopant. The host and the dopant of the second EML 1440 may be same as the host and the dopant of the third EML 1460. Alternatively, the host and the dopant of the second EML 1440 may be different from the host and the dopant of the third EML 1460. For example, the dopant in the second EML 1440 may have a difference in the emitting efficiency and/or the emitting light wavelength from the dopant in the third EML 1460.

In each of the lower EML 1420a, the second EML 1440 and the third EML 1460, the dopant may include at least one of a phosphorescent compound, a fluorescent compound and a delayed fluorescent compound.

The organic light emitting diode D in the first to third pixel regions P1 to P3 (of FIG. 8) emits the white light, and the white light passes through the color filter layer 1120 (of FIG. 8) in the first to third pixel regions P1 to P3. Accordingly, the OLED device 1100 (of FIG. 8) can provide a full-color image.

In FIG. 10, the organic light emitting diode D has a three-stack (triple-stack) structure including the second and third EMLs 1440 and 1460 being the blue EML with the first EML 1420. Alternatively, one of the second and third EMLs 1440 and 1460 may be omitted such that the organic light emitting diode D may have a two-stack (double-stack) structure.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic compound of formula 1:

[Formula 1]

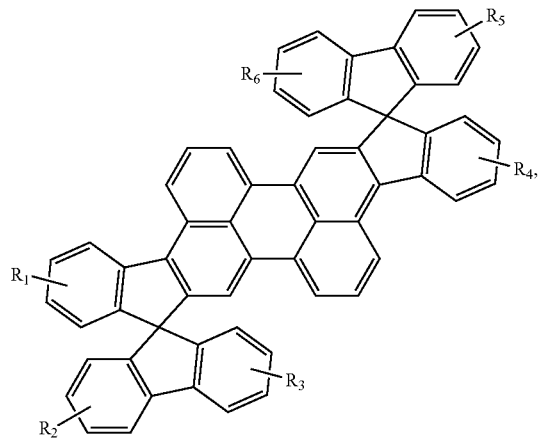

wherein each of $R_1$ to $R_6$ is independently selected from hydrogen, deuterium, tritium, halogen, a cyano group, a C1 to C20 alkyl group, a C6 to C30 aryl group, a C5 to C30 heteroaryl group and a C1 to C20 amine group.

2. The organic compound according to claim 1, wherein one or two of $R_1$ to $R_3$ and one or two of $R_4$ to $R_6$ are each independently selected from halogen, a cyano group, a C1 to C20 alkyl group, a C6 to C30 aryl group, a C5 to C30 heteroaryl group and a C1 to C20 amine group, and the rest of $R_1$ to $R_6$ are selected from hydrogen, deuterium, and tritium.

3. The organic compound according to claim 1, wherein the organic compound is represented by one of Formulas 2-1 to 2-3:

[Formula 2-1]

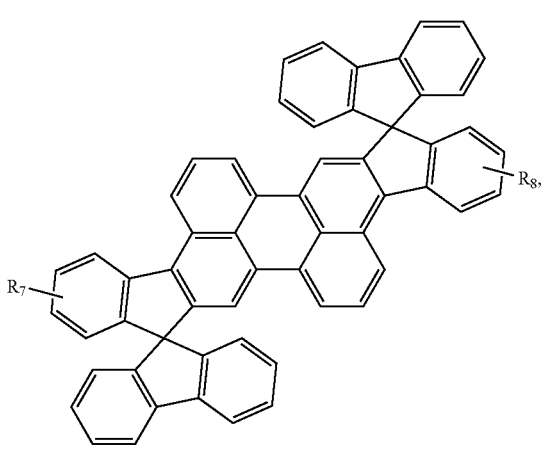

[Formula 2-2]

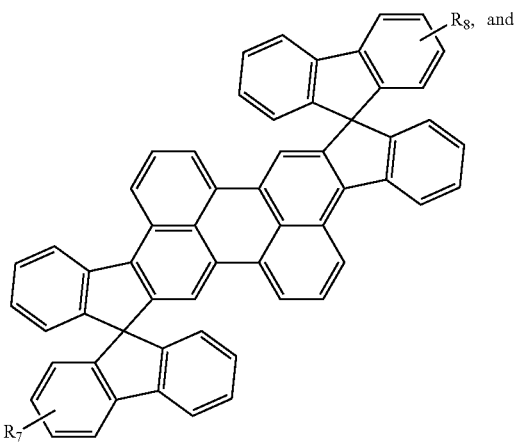

[Formula 2-3]

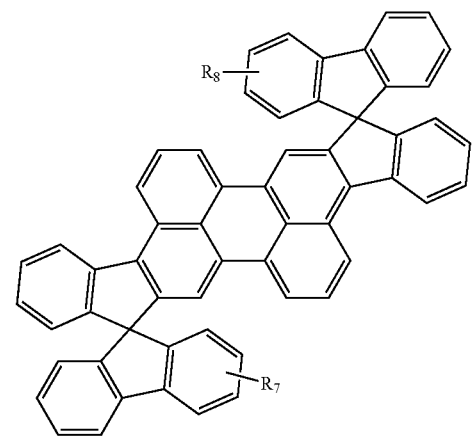

wherein each of $R_7$ and $R_8$ is independently selected from hydrogen, deuterium, tritium, halogen, cyano group, a C1 to C20 alkyl group, a C6 to C30 aryl group, a C5 to C30 heteroaryl group and a C1 to C20 amine group.

4. The organic compound according to claim 3, wherein at least one of $R_7$ and $R_8$ is selected from hydrogen, deuterium and tritium.

5. The organic compound according to claim 1, wherein the organic compound is selected from the group consisting of:
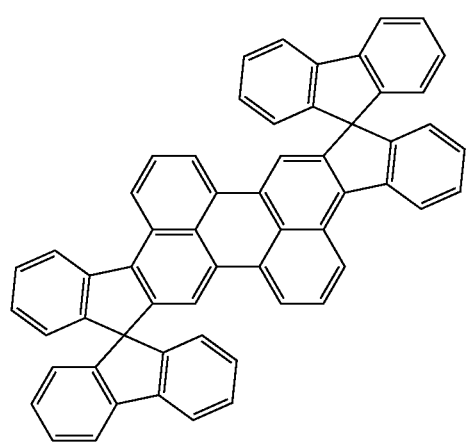
1-1
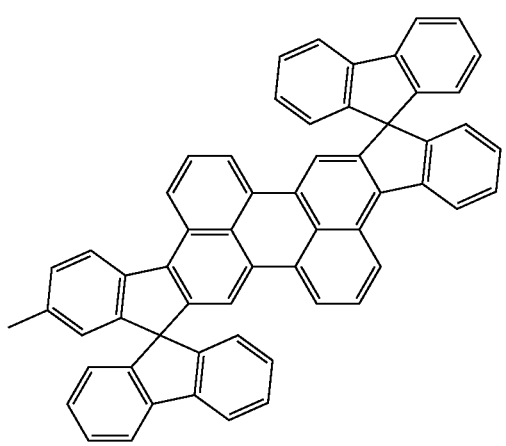
1-2
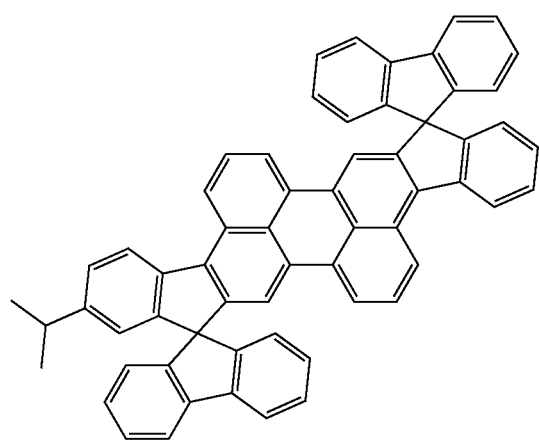
1-3
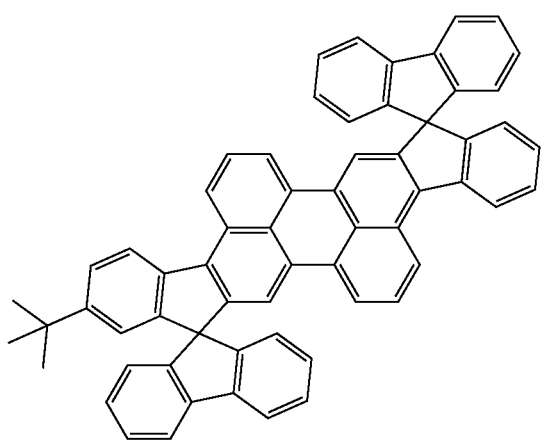
1-4
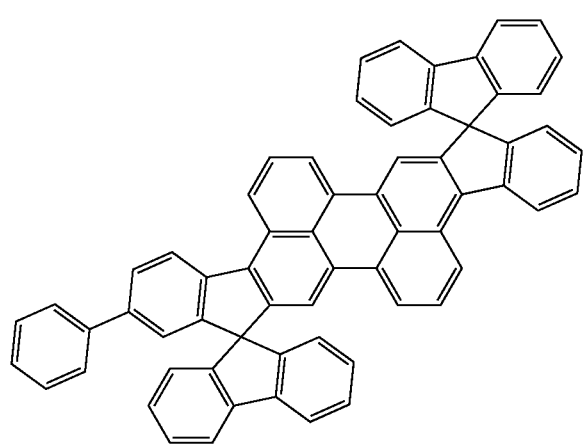
1-5
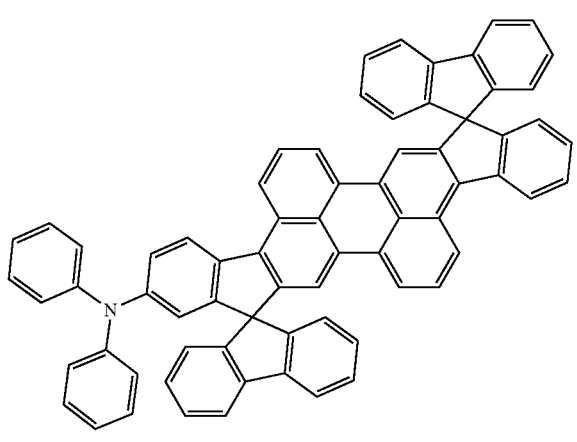
1-6

-continued
1-7
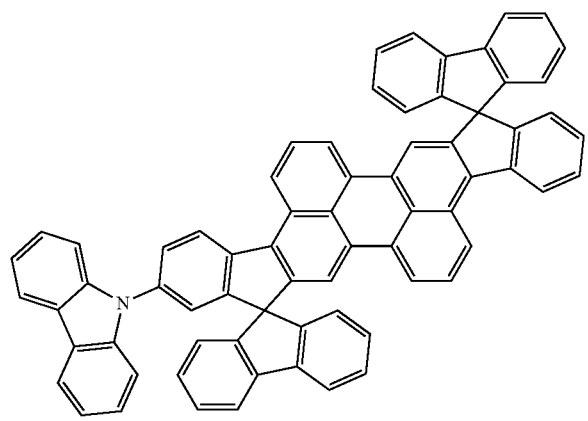
1-8
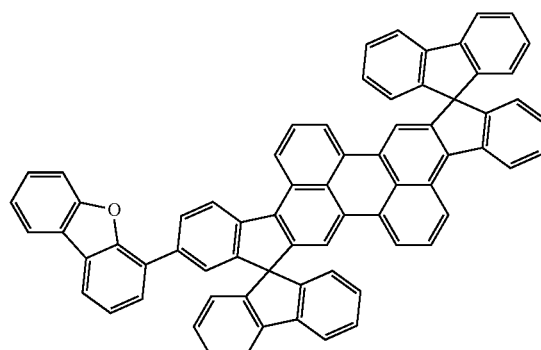
1-9
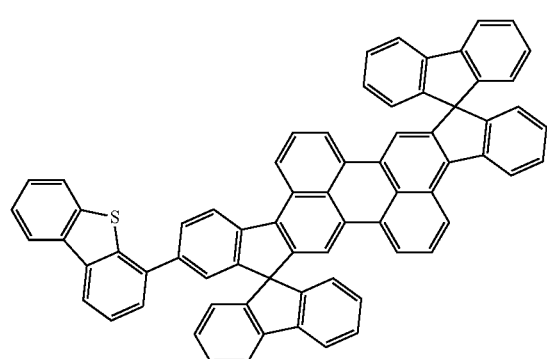
1-10
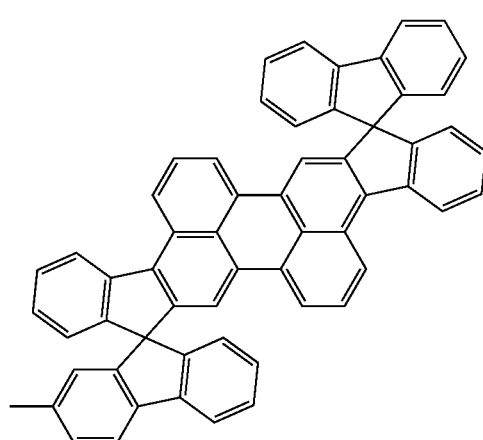
1-11
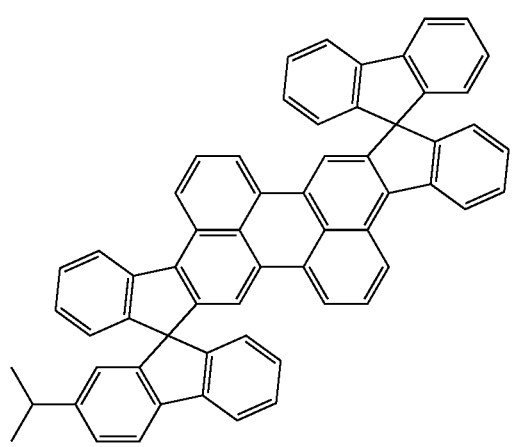
1-12
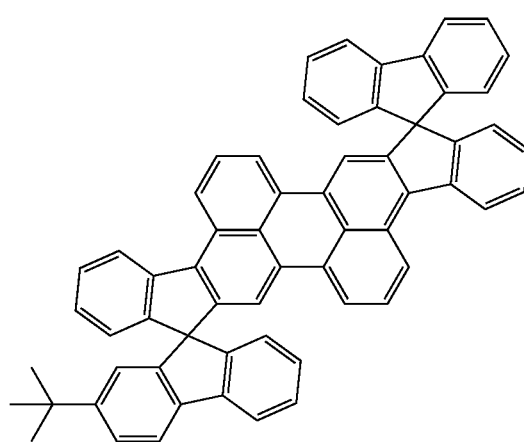

-continued
1-13
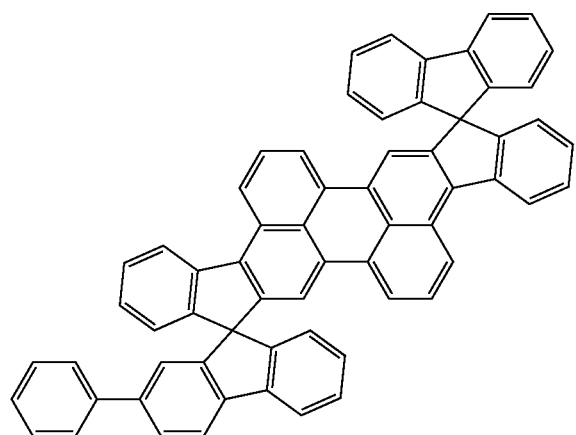
1-14
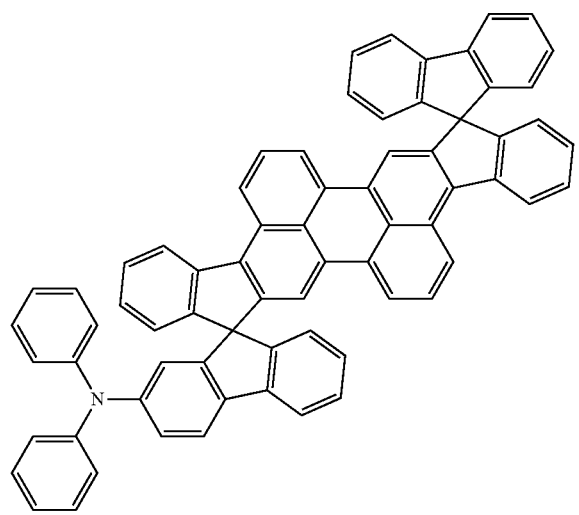
1-15
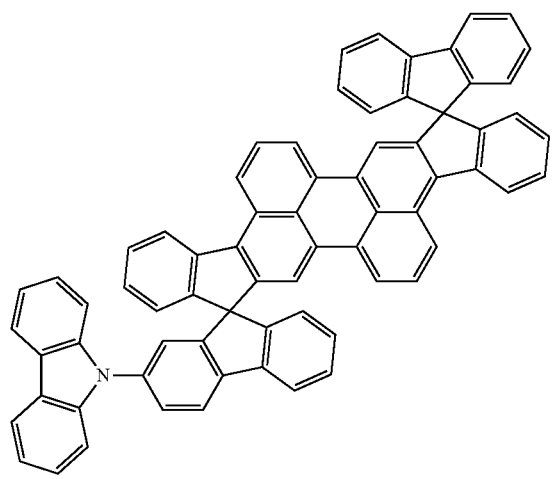
1-16
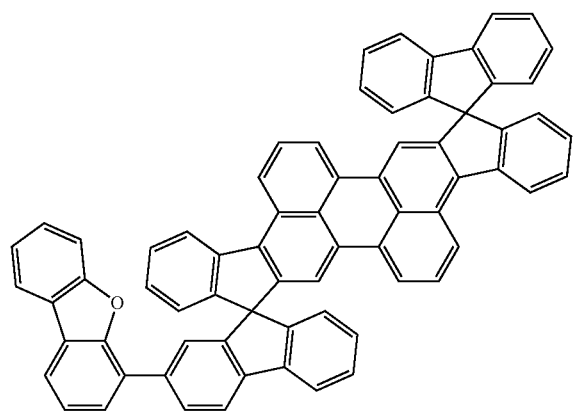
1-17
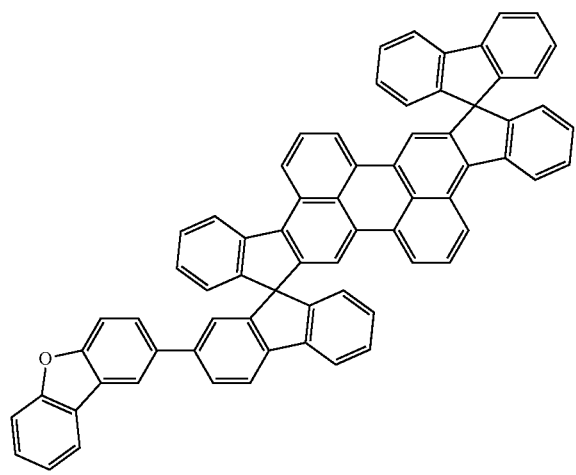
1-18
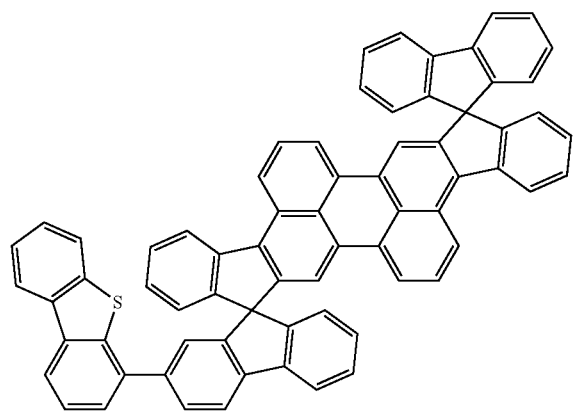

-continued
1-19
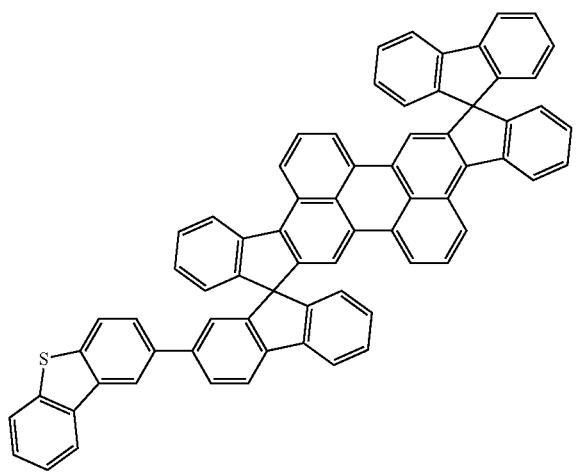
1-20
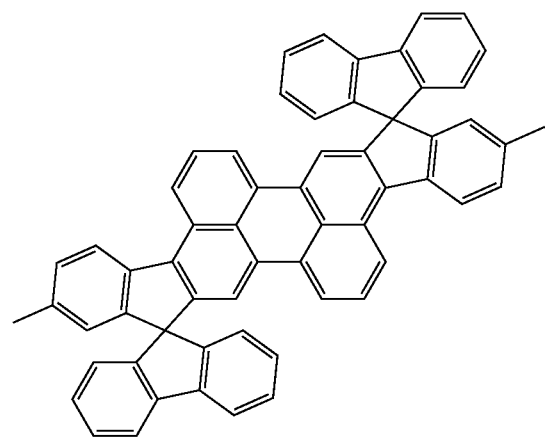
1-21
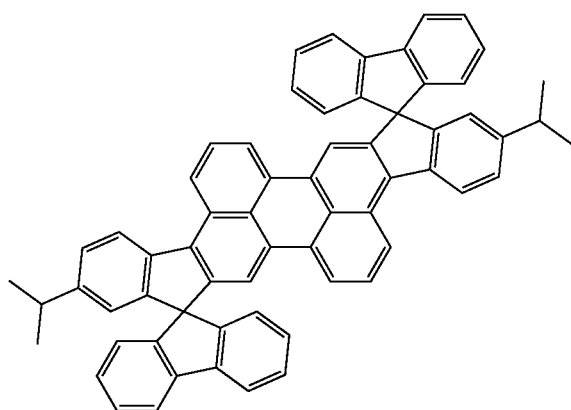
1-22
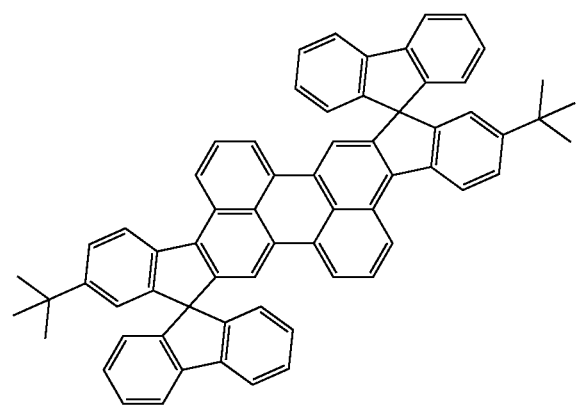
1-23
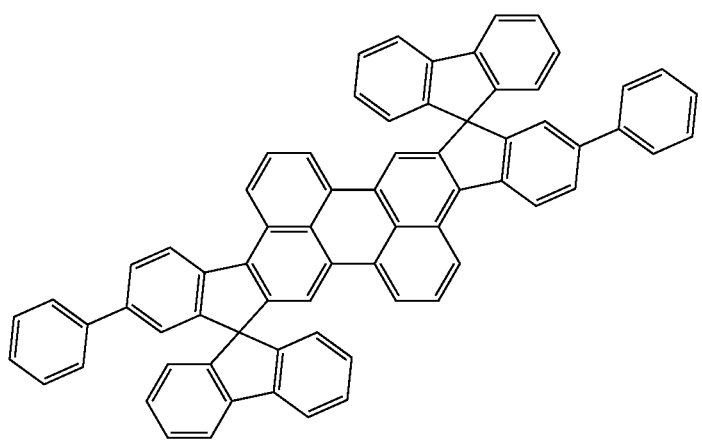

1-24
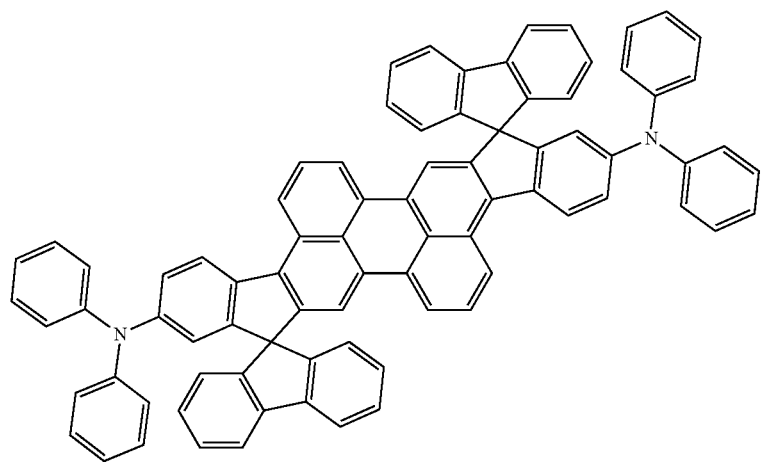
1-25
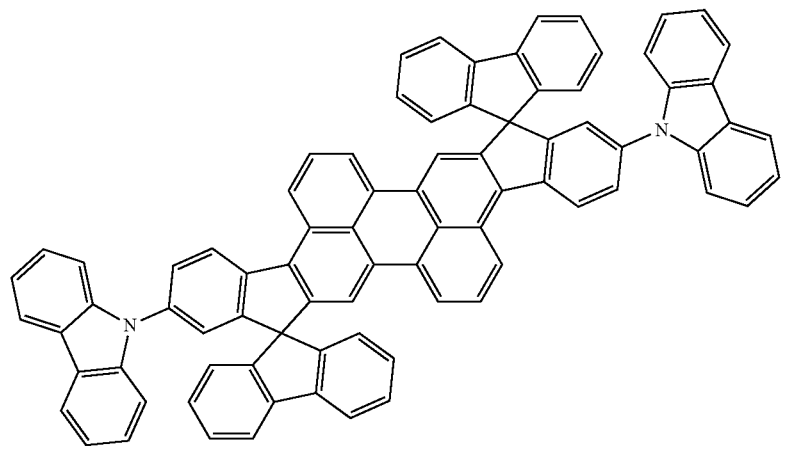
1-26
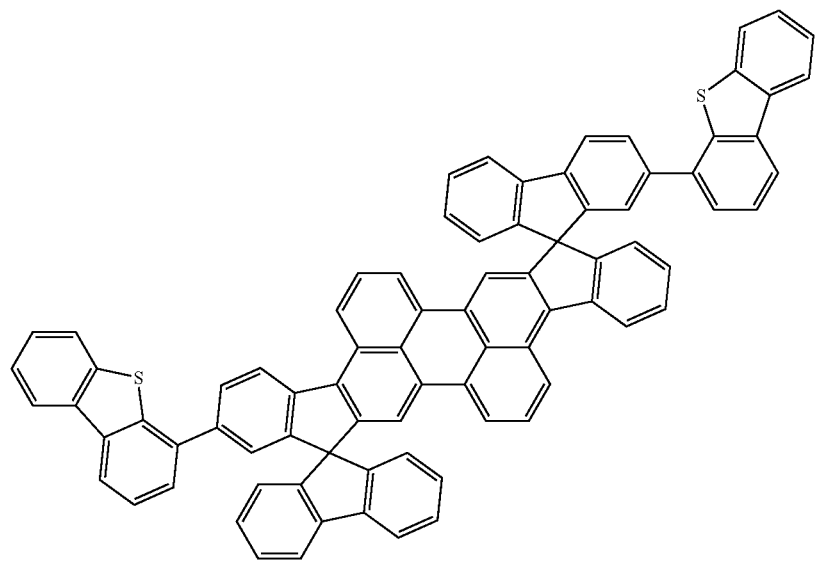

1-27
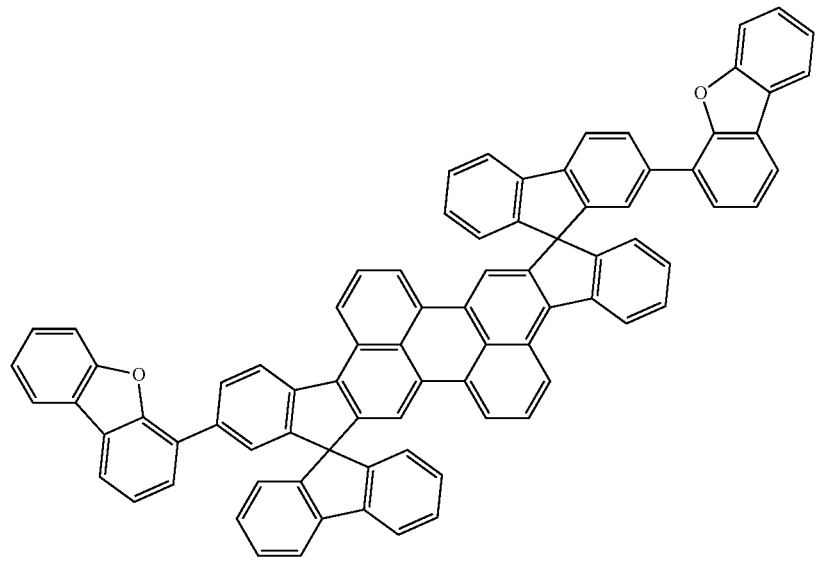
1-28
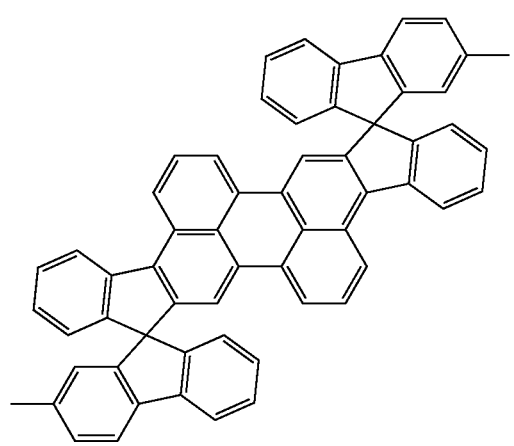
1-29
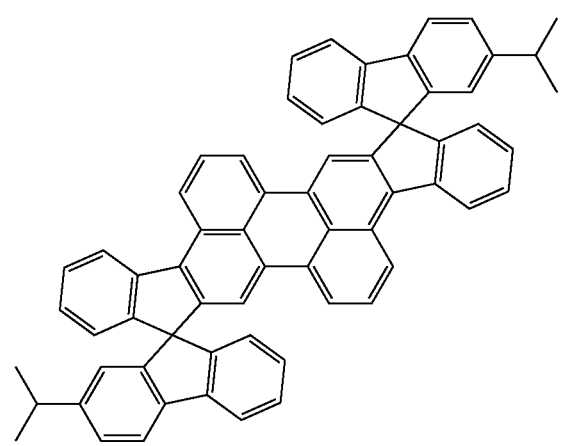
1-30
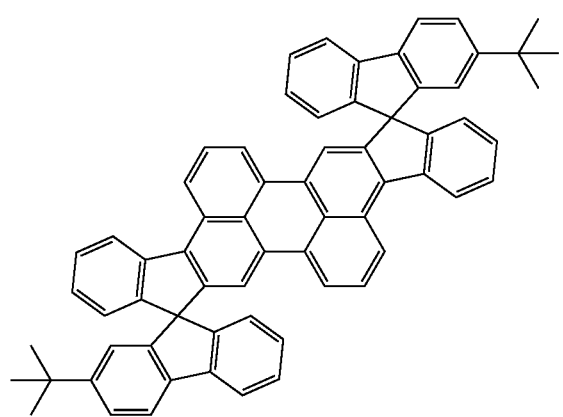
1-31
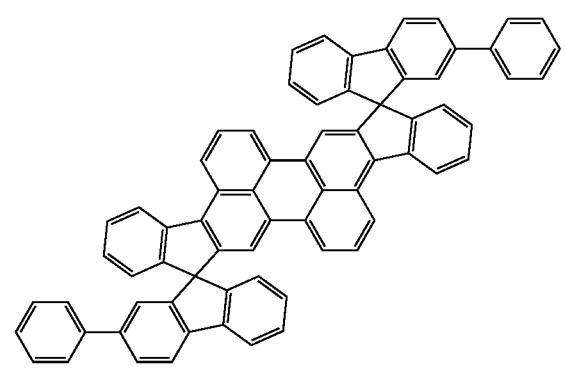

-continued
1-32
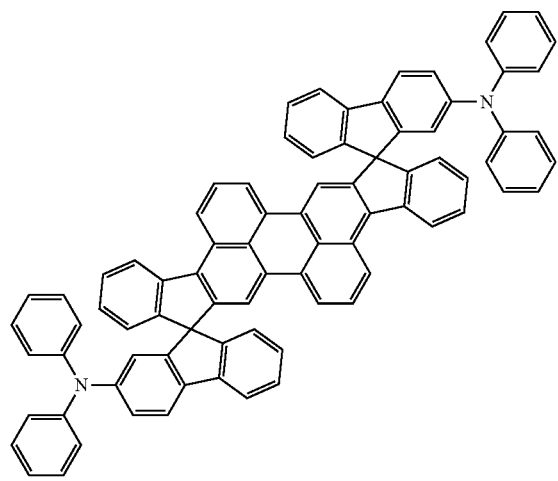
1-33
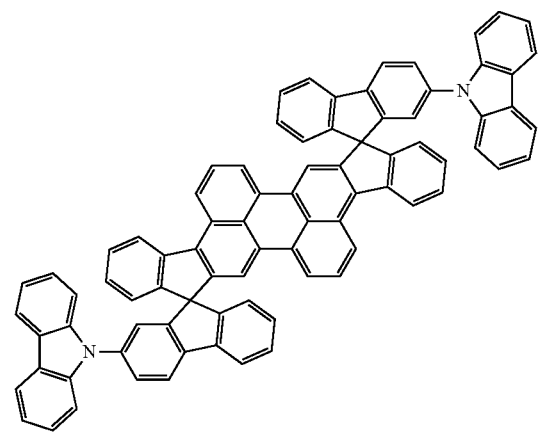
1-34
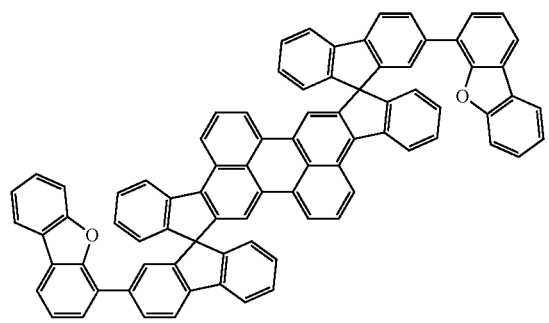
1-35
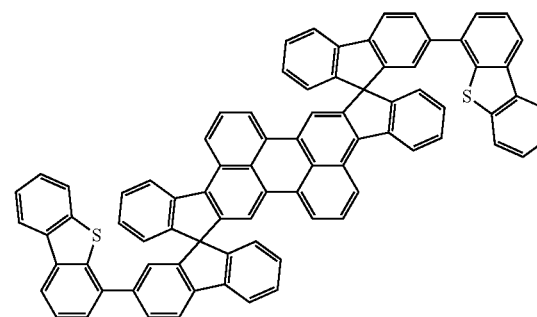
1-36
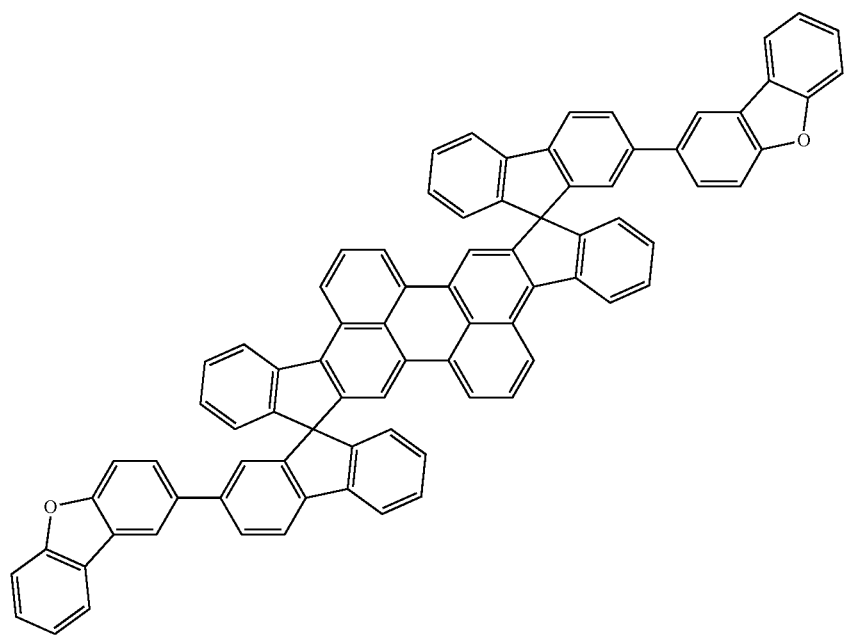

-continued
1-37
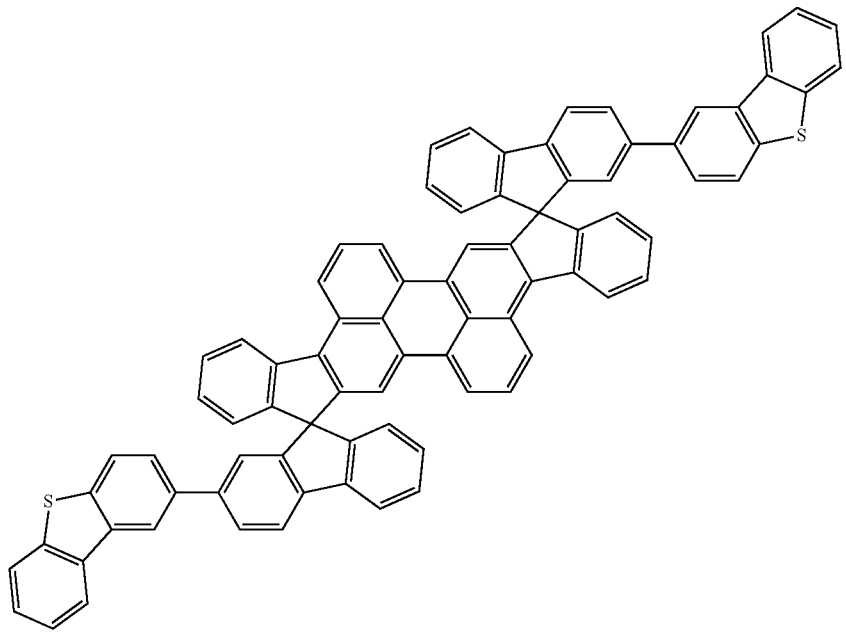
1-38
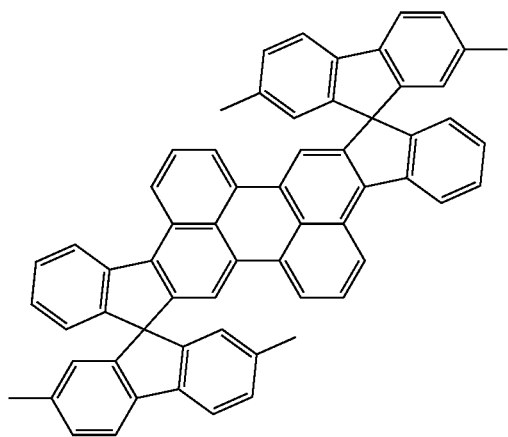
1-39
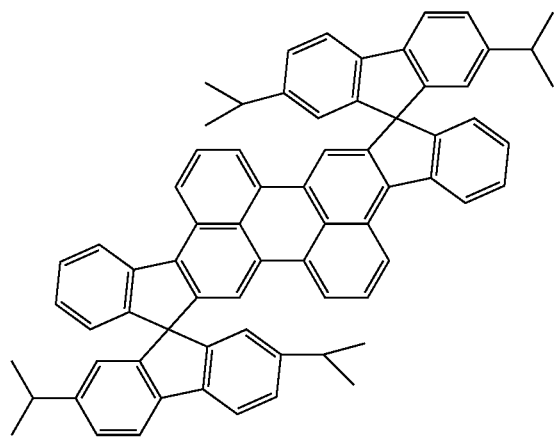
1-40
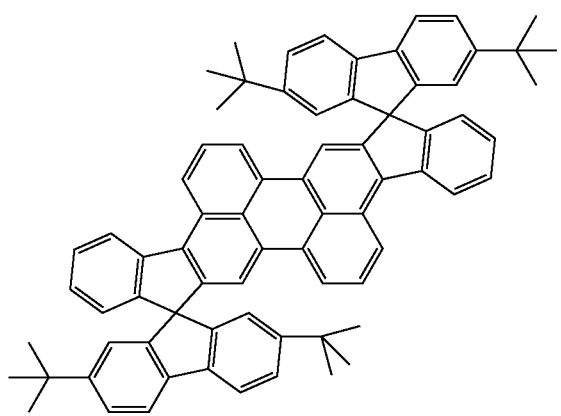
1-41
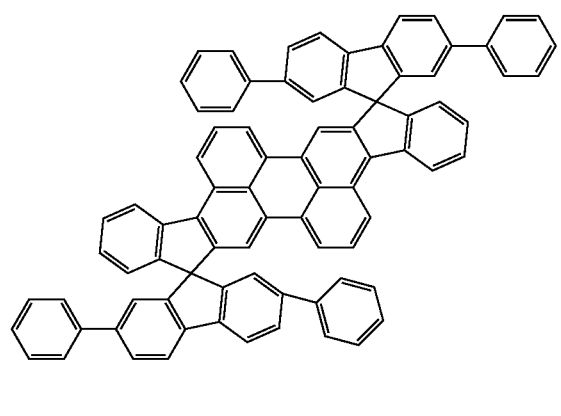

1-42
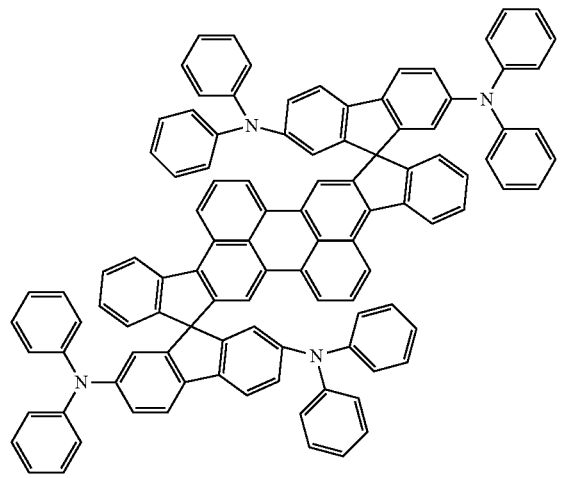
1-43
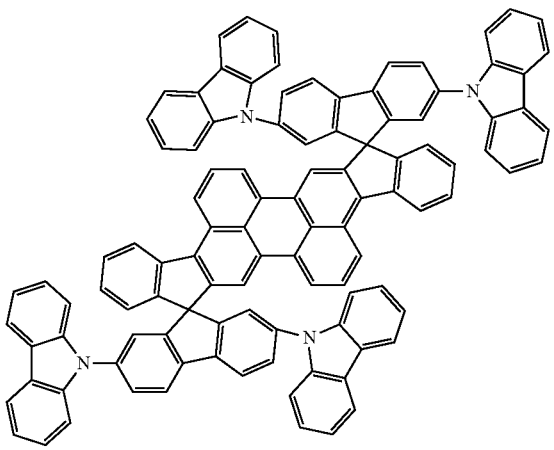
1-44
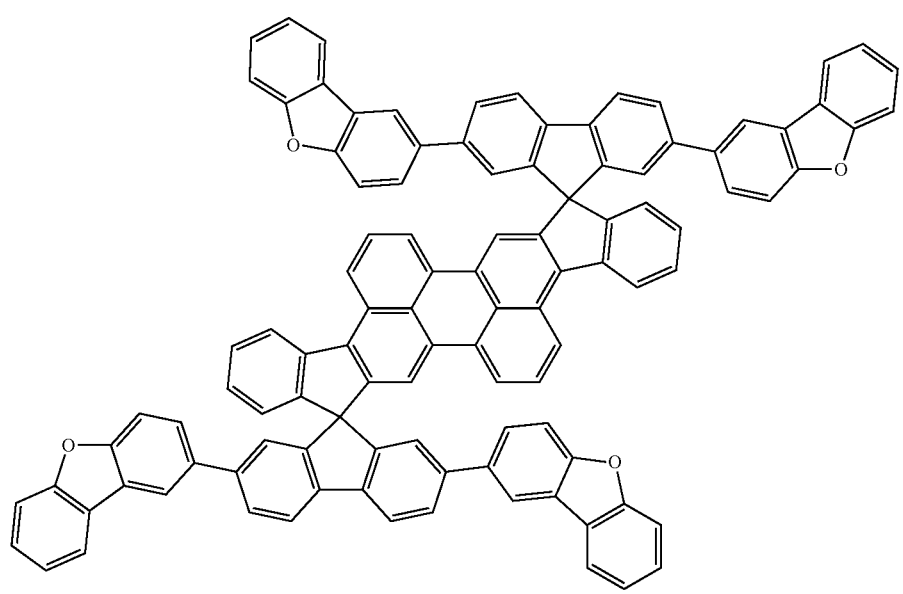

-continued
1-45
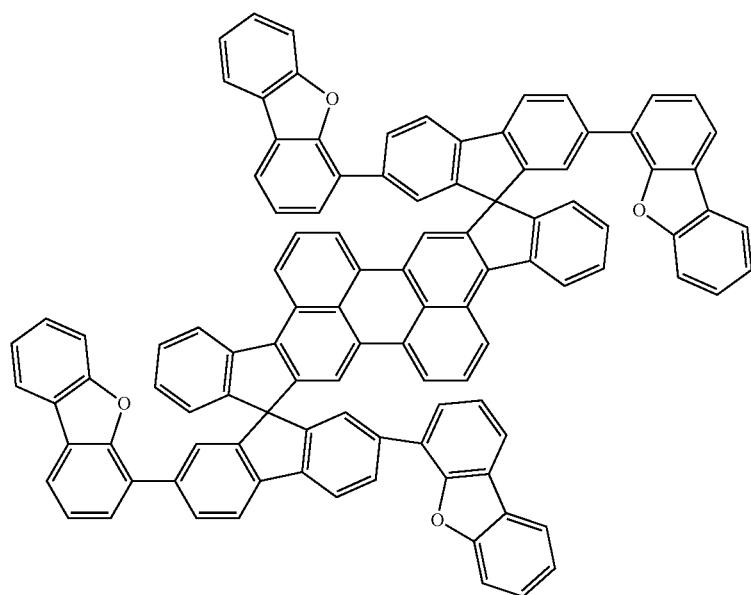
1-46
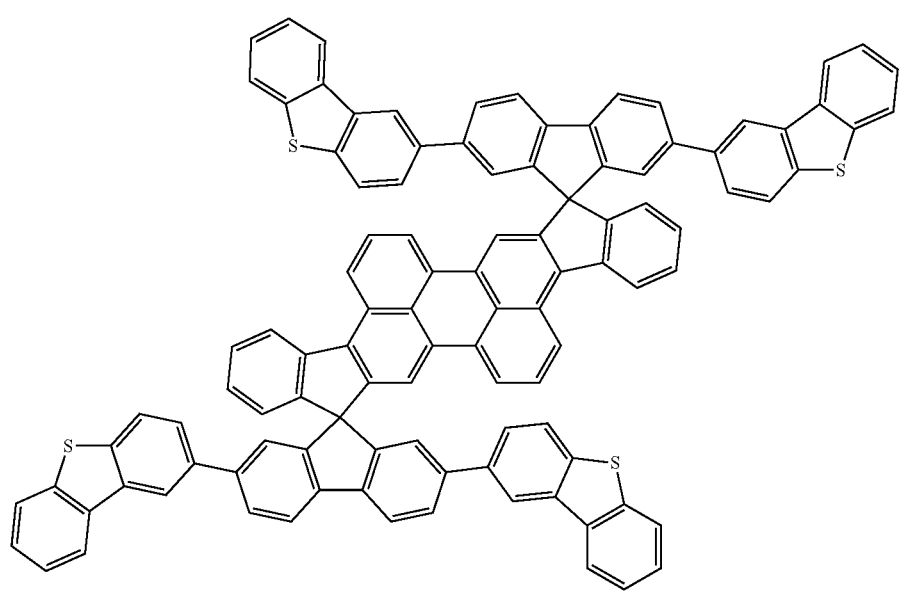

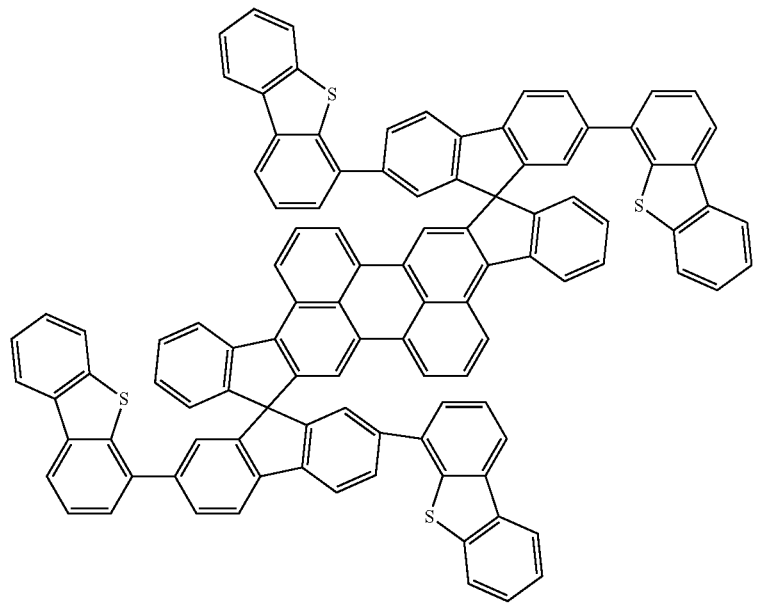

1-47

6. An organic light emitting diode, comprising:
   a first electrode;
   a second electrode facing the first electrode; and
   a first emitting material layer between the first and second electrodes and including an organic compound of formula 1:
   wherein each of $R_1$ to $R_6$ is independently selected from hydrogen, deuterium, tritium, halogen, a cyano group, a C1 to C20 alkyl group, a C6 to C30 aryl group, a C5 to C30 heteroaryl group and a C1 to C20 amine group.

7. The organic light emitting diode according to claim 6, wherein the organic compound is used as a first fluorescent dopant, and the first emitting material layer further includes a first host.

8. The organic light emitting diode according to claim 7, wherein the first emitting material layer further includes a delayed fluorescent dopant.

9. The organic light emitting diode according to claim 8, wherein the first host is one of compounds in Formula 4:

[Formula 4]

H1

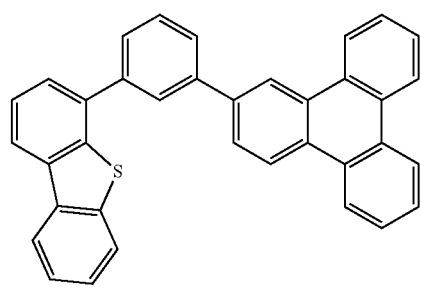

-continued

H2

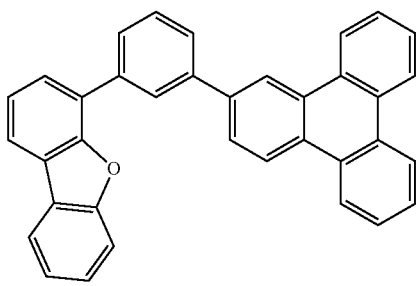

H3

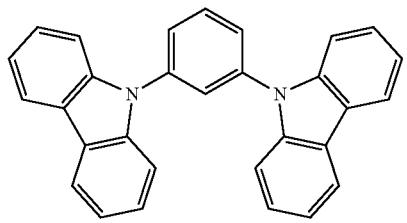

H4

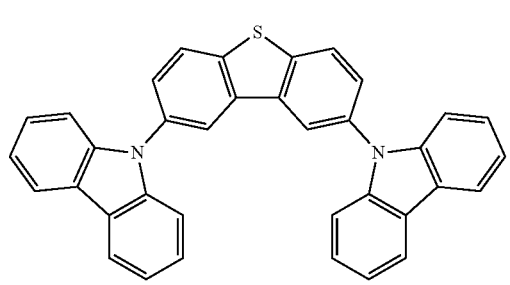

-continued

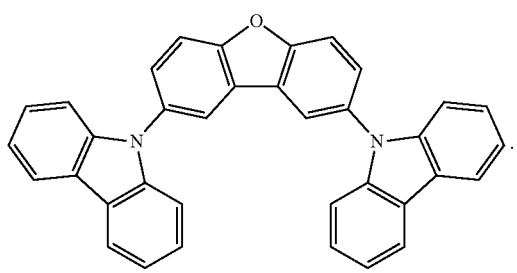
H5

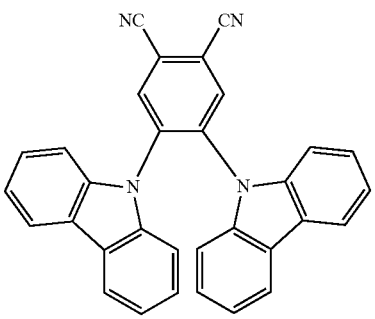
T4

10. The organic light emitting diode according to claim 8, wherein the delayed fluorescent dopant is one of compounds in Formula 5:

[Formula 5]

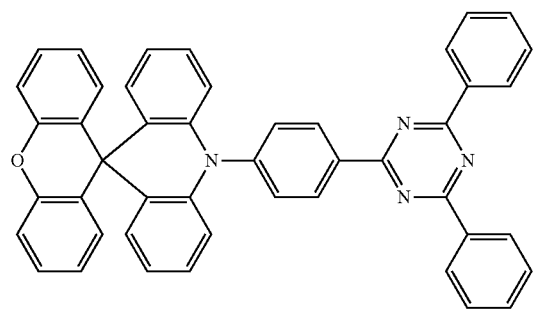
T1

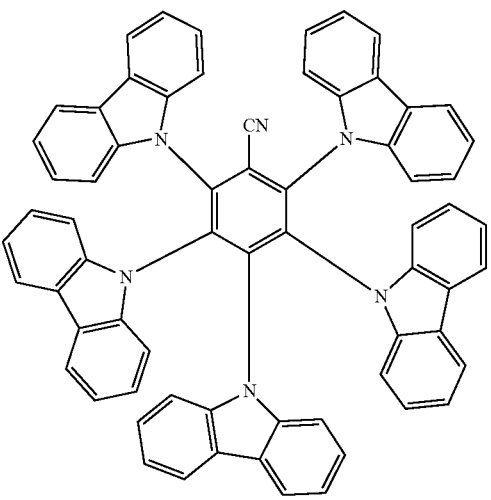
T5

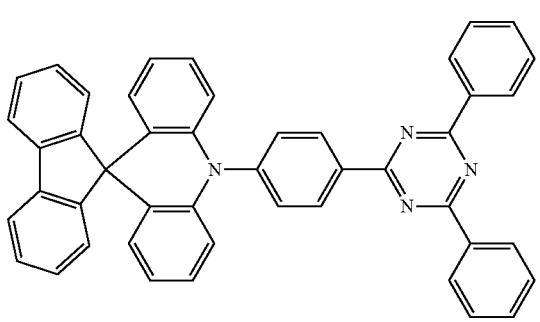
T2

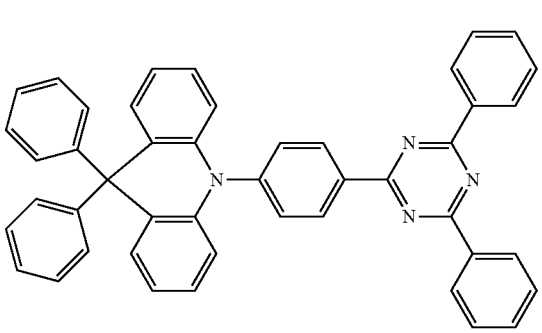
T3

11. The organic light emitting diode according to claim 7, further comprising:
   a second emitting material layer including a second host and a delayed fluorescent dopant and positioned between the first electrode and the first emitting material layer.

12. The organic light emitting diode according to claim 11, further comprising:
   a third emitting material layer including a third host and a second fluorescent dopant and positioned between the second electrode and the first emitting material layer.

13. The organic light emitting diode according to claim 12, wherein the second fluorescent dopant is the organic compound of Formula 1.

14. The organic light emitting diode according to claim 7, further comprising:
   a second emitting material layer including a second host and a delayed fluorescent dopant and positioned between the second electrode and the first emitting material layer.

15. The organic light emitting diode according to claim 6, wherein one or two of $R_1$ to $R_3$ and one or two of $R_4$ to $R_6$ are each independently selected from halogen, a cyano group, a C1 to C20 alkyl group, a C6 to C30 aryl group, a C5 to C30 heteroaryl group and a C1 to C20 amine group, and the rest of $R_1$ to $R_6$ are selected from hydrogen, deuterium, and tritium.

16. The organic light emitting diode according to claim 6, wherein the organic compound is selected from the group consisting of:
1-1
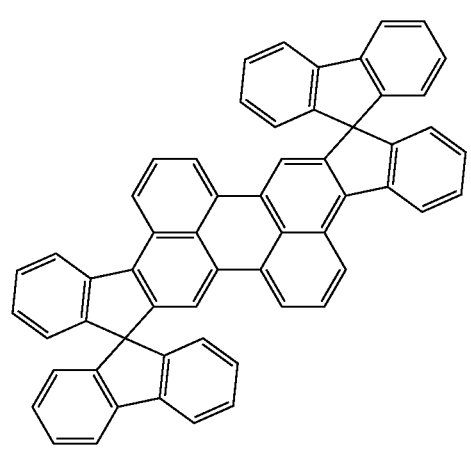
1-2
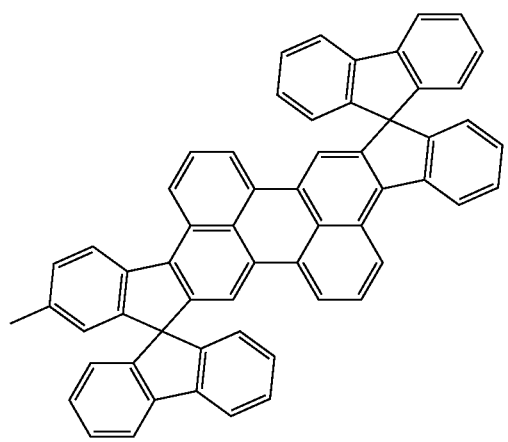
1-3
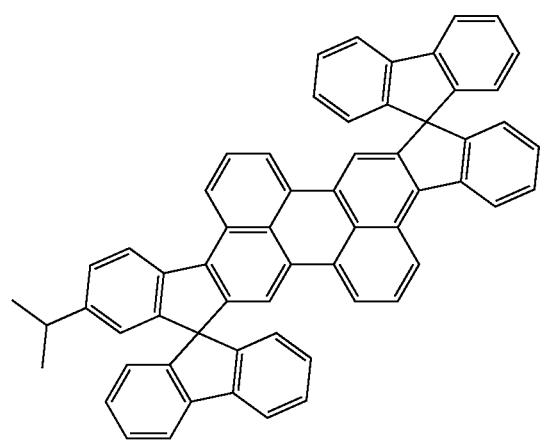
1-4
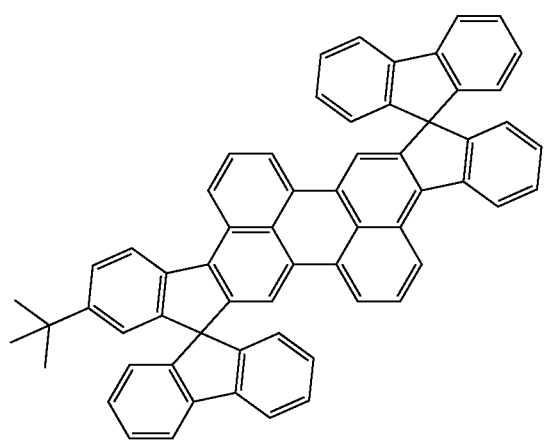
1-5
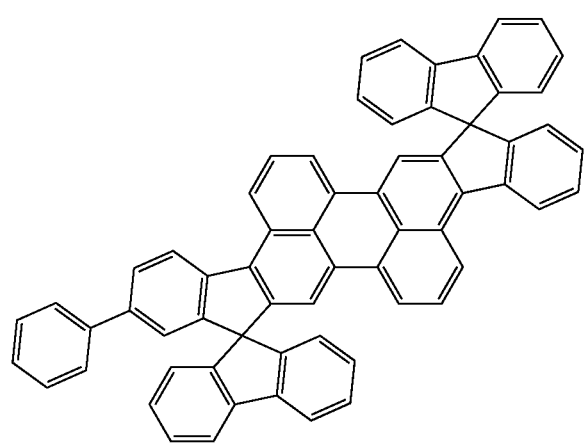
1-6
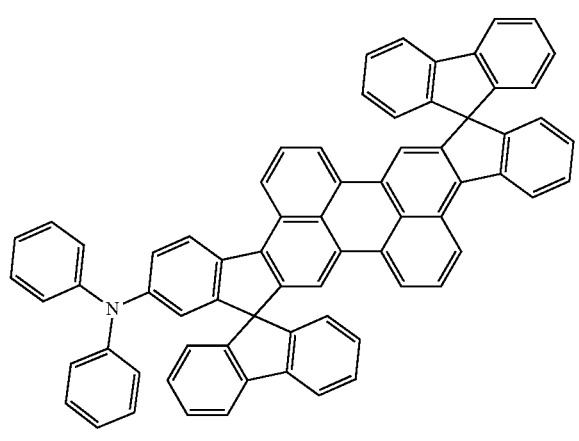

-continued
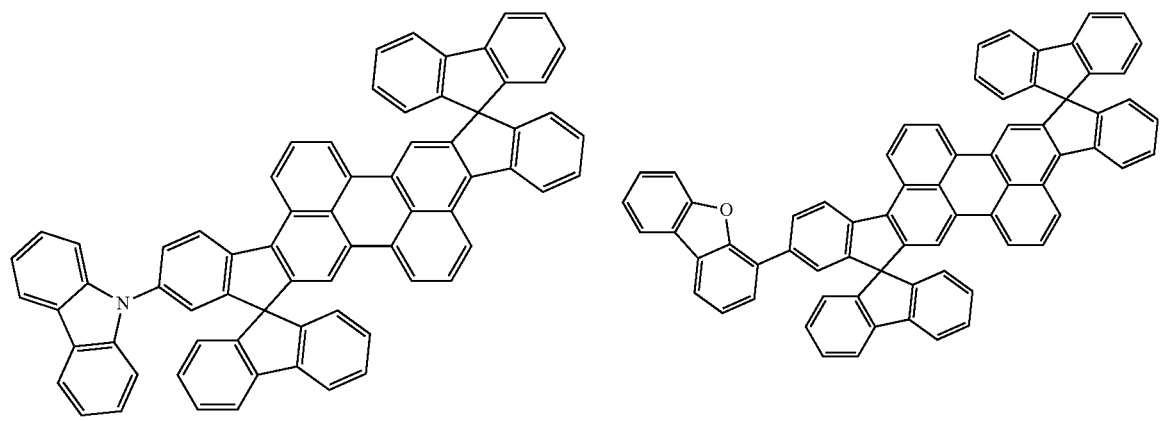
1-7
1-8
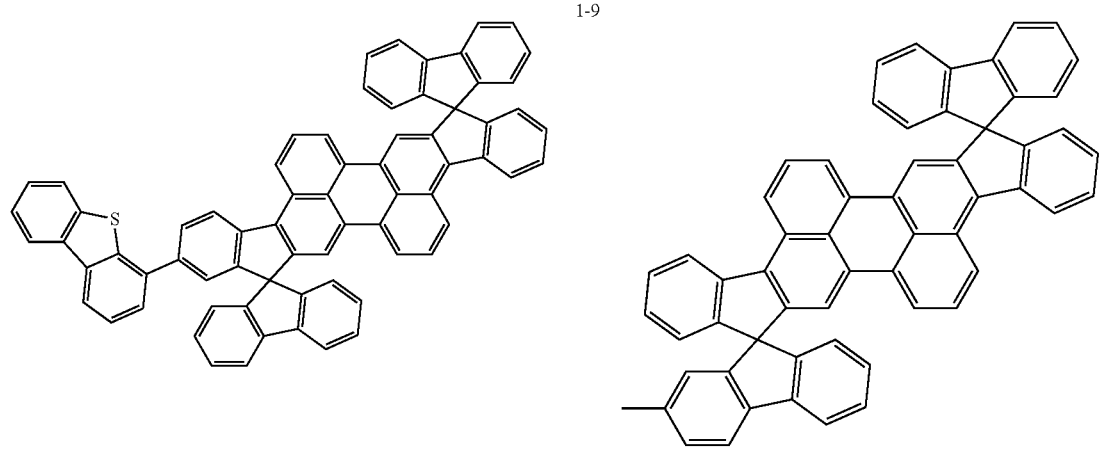
1-9
1-10
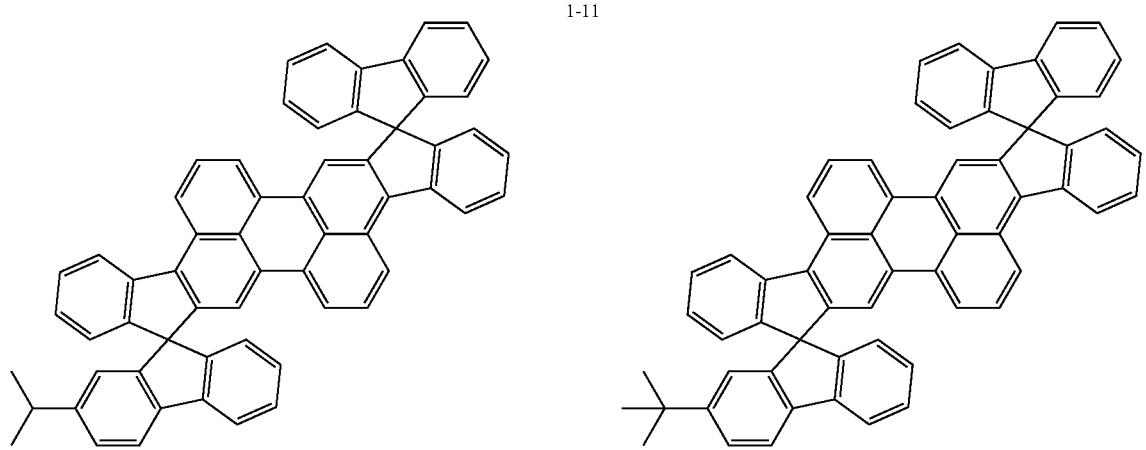
1-11
1-12

-continued
1-13
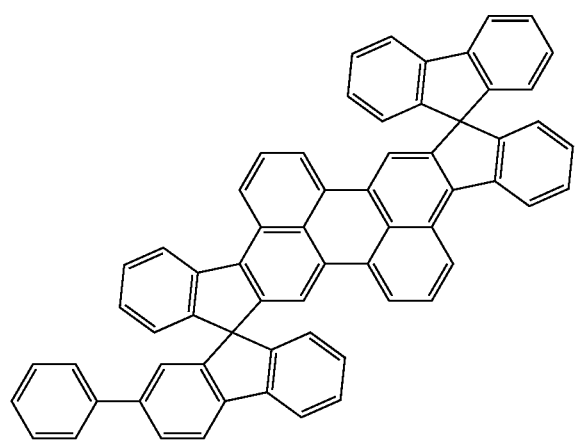
1-14
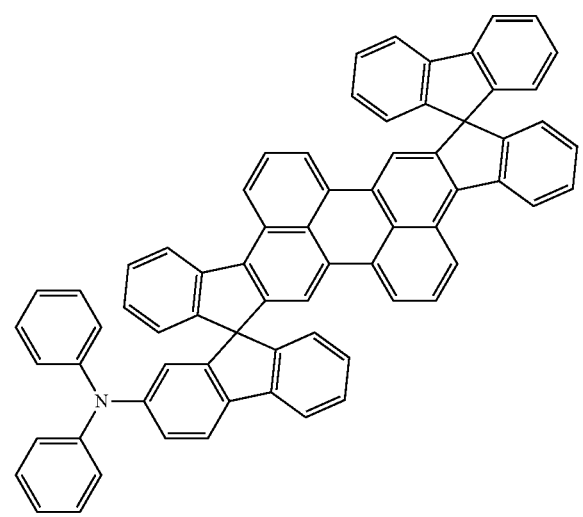
1-15
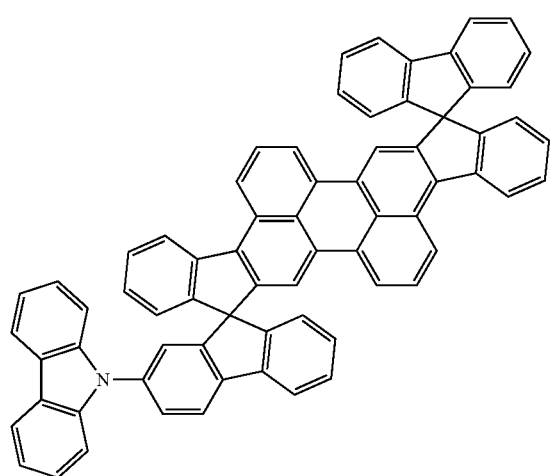
1-16
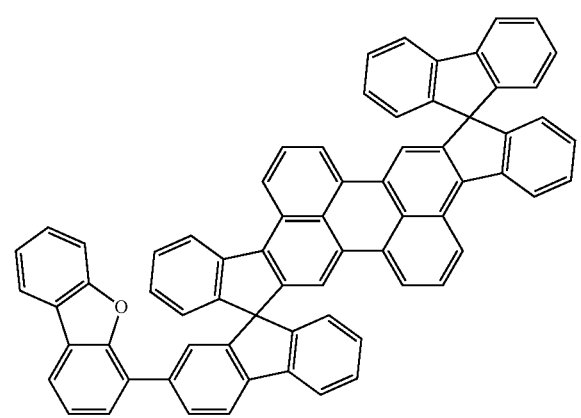
1-17
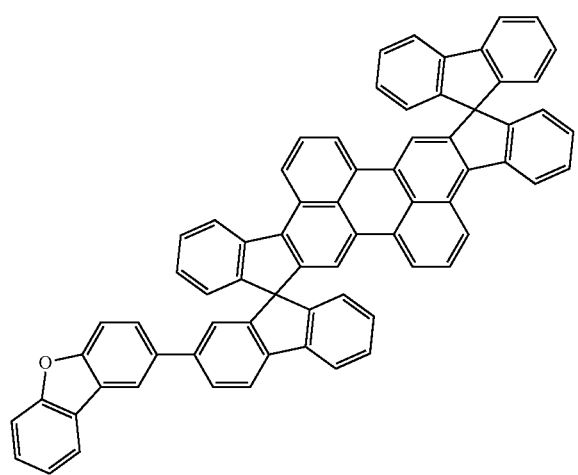
1-18
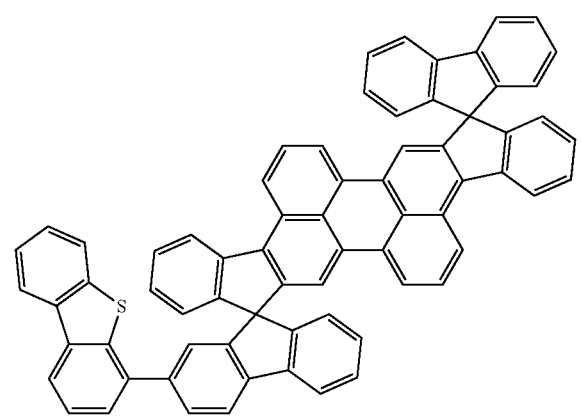

-continued
1-19
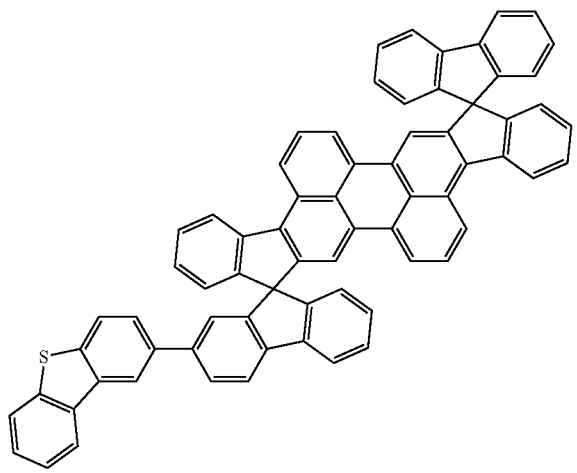
1-20
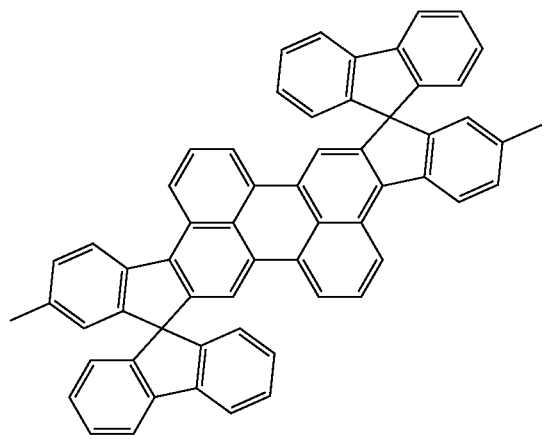
1-21
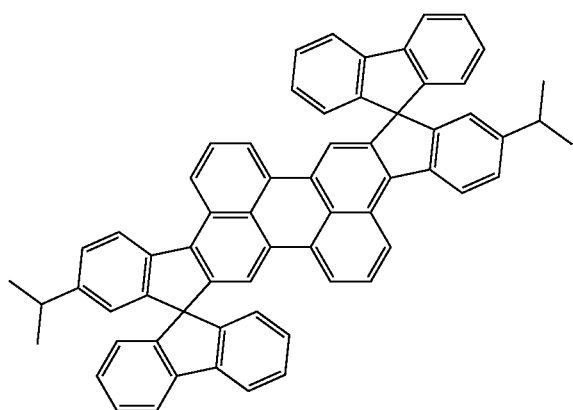
1-22
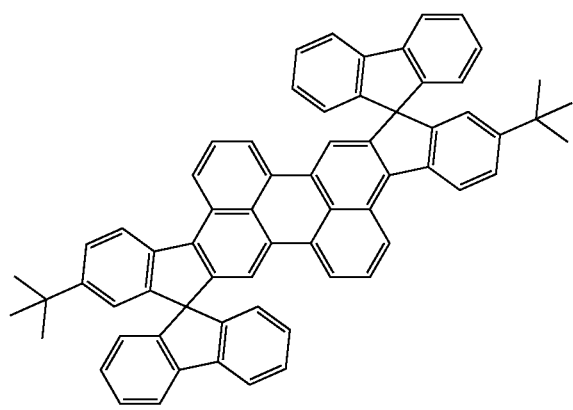
1-23
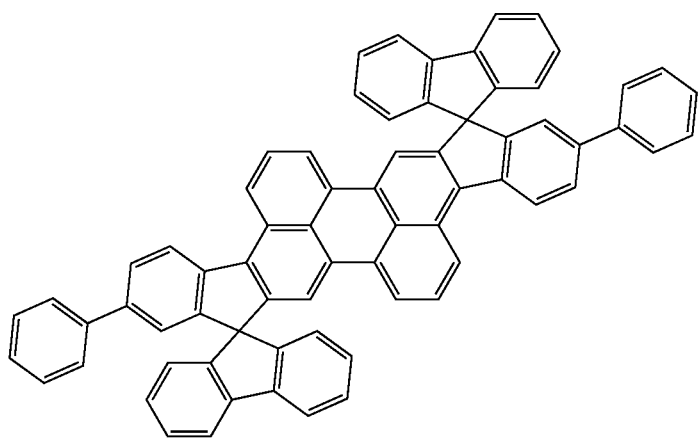

1-24
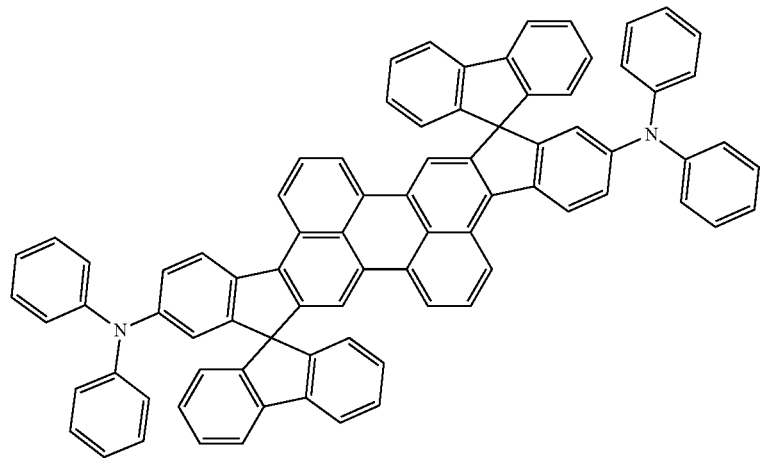
1-25
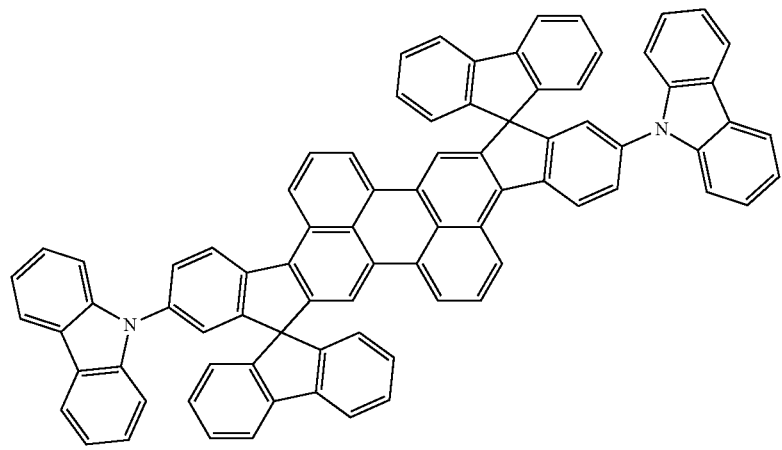
1-26
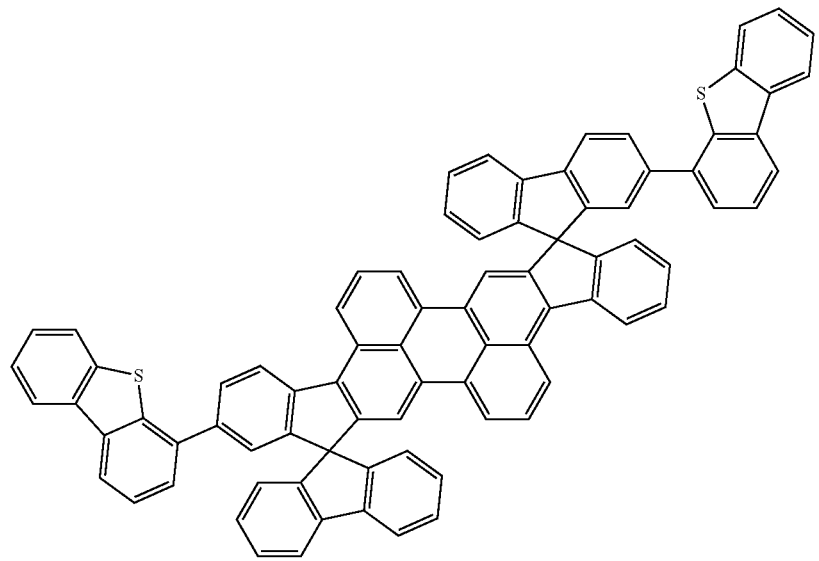

1-27
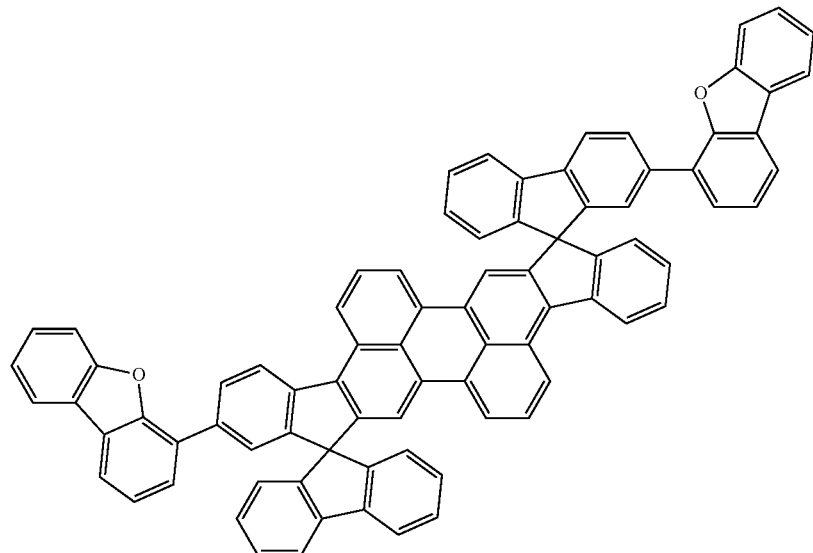
1-28
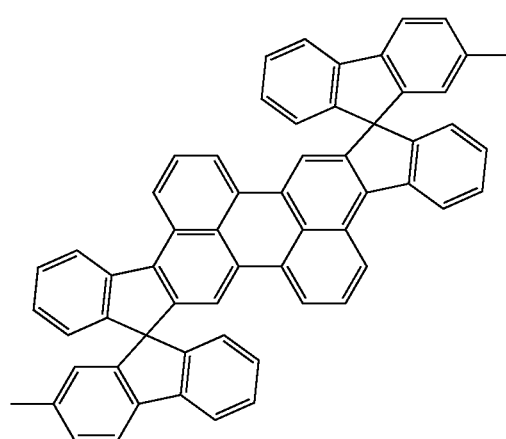
1-29
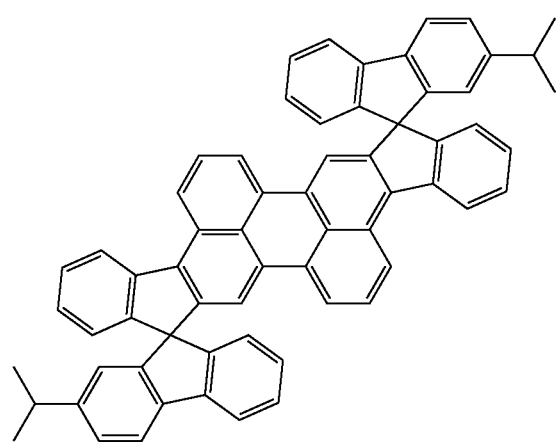
1-30
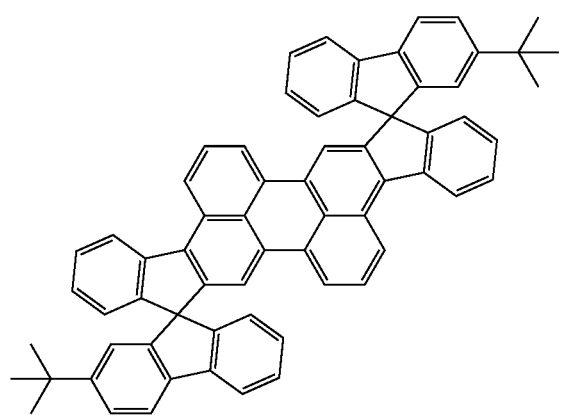
1-31
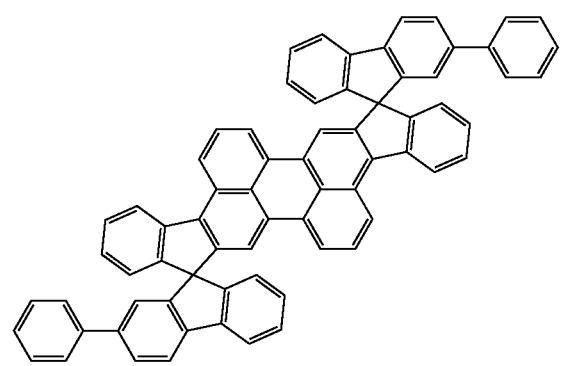

-continued
1-32
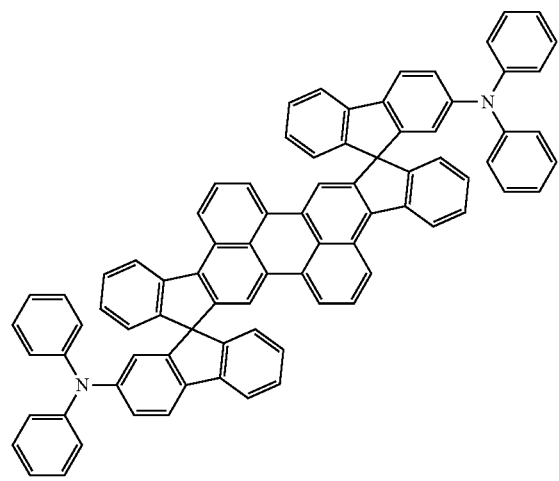
1-33
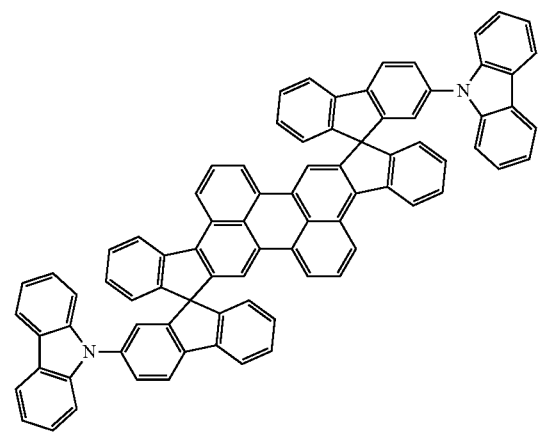
1-34
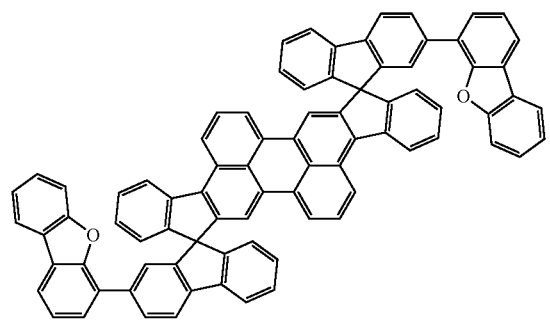
1-35
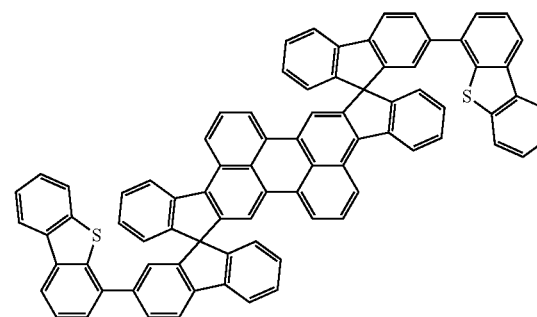
1-36
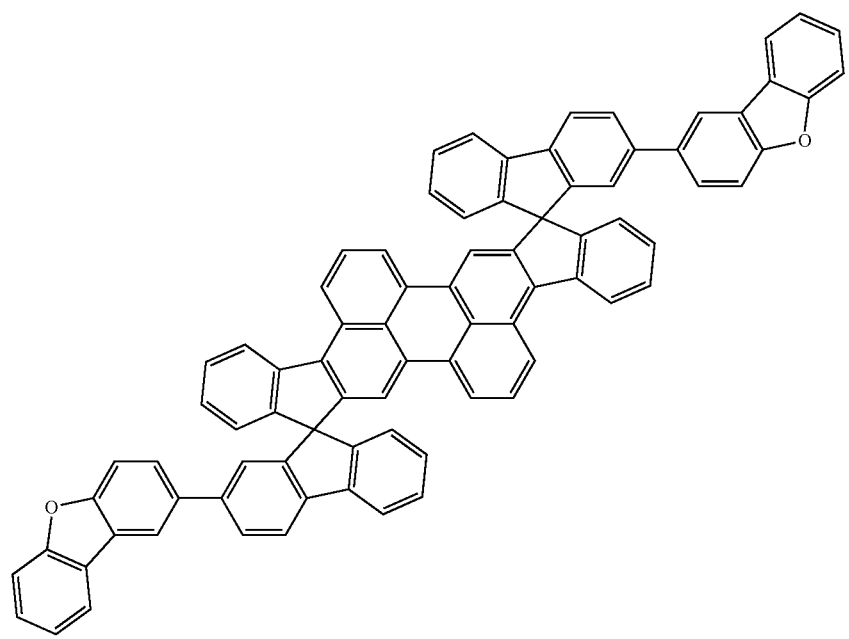

1-37
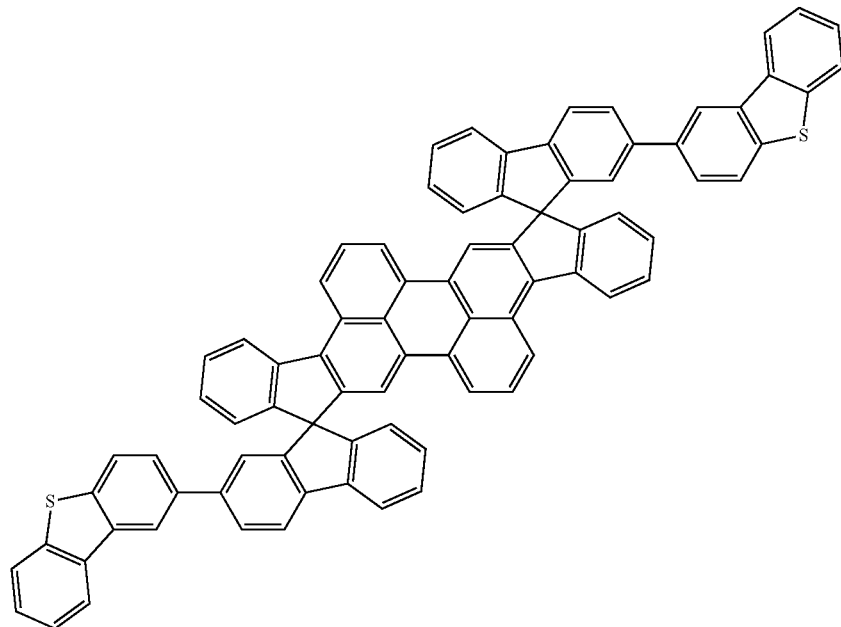
1-38
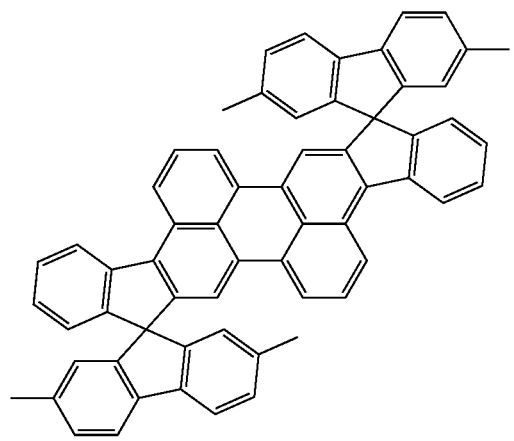
1-39
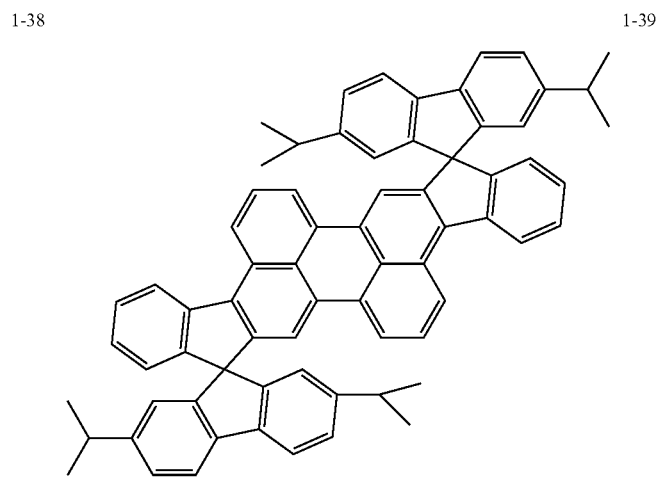
1-40
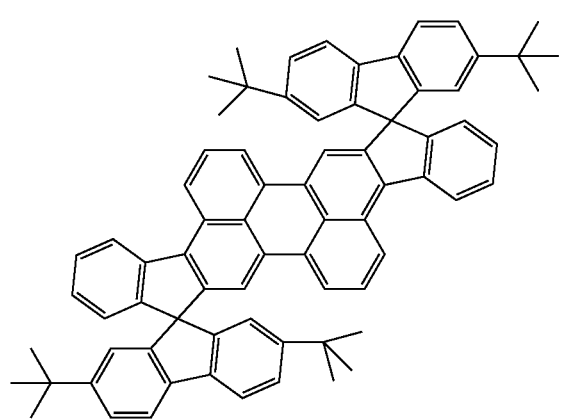
1-41
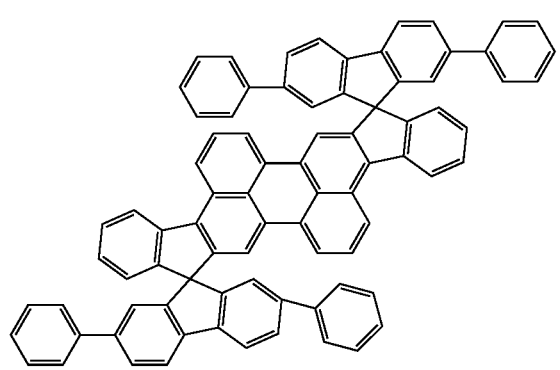

-continued
1-42
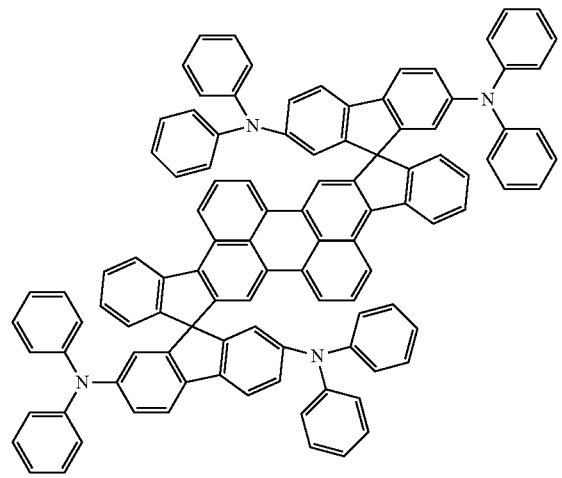
1-43
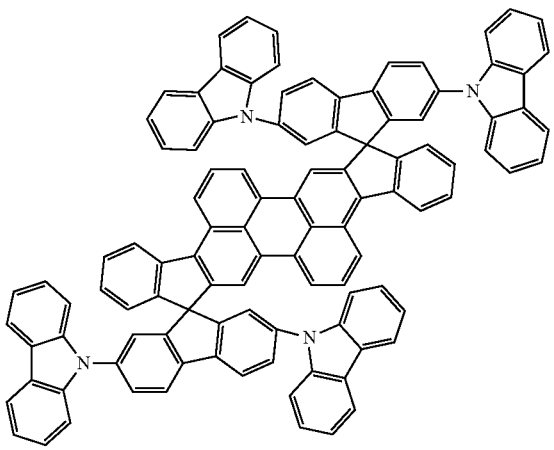
1-44
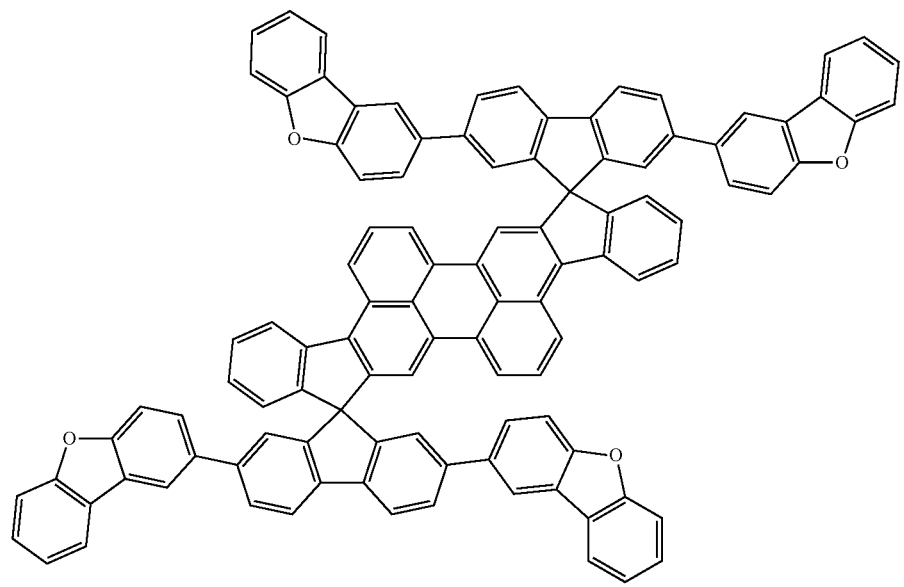

1-45
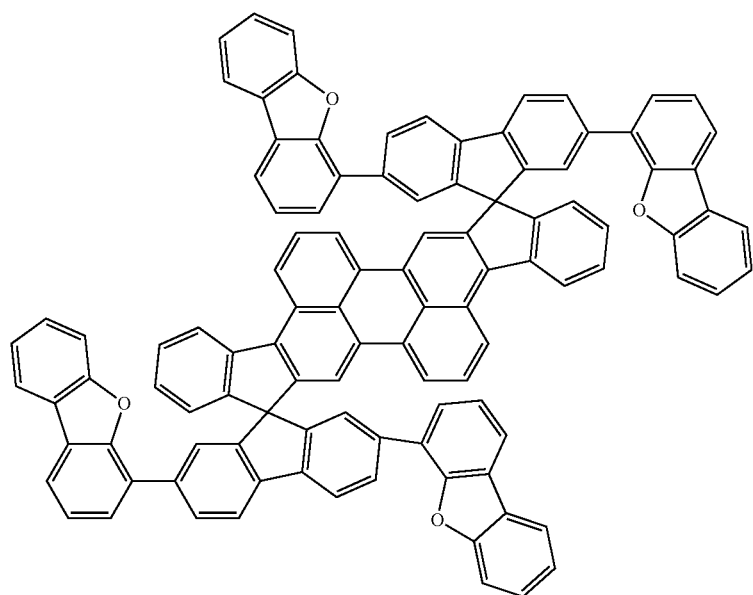
1-46
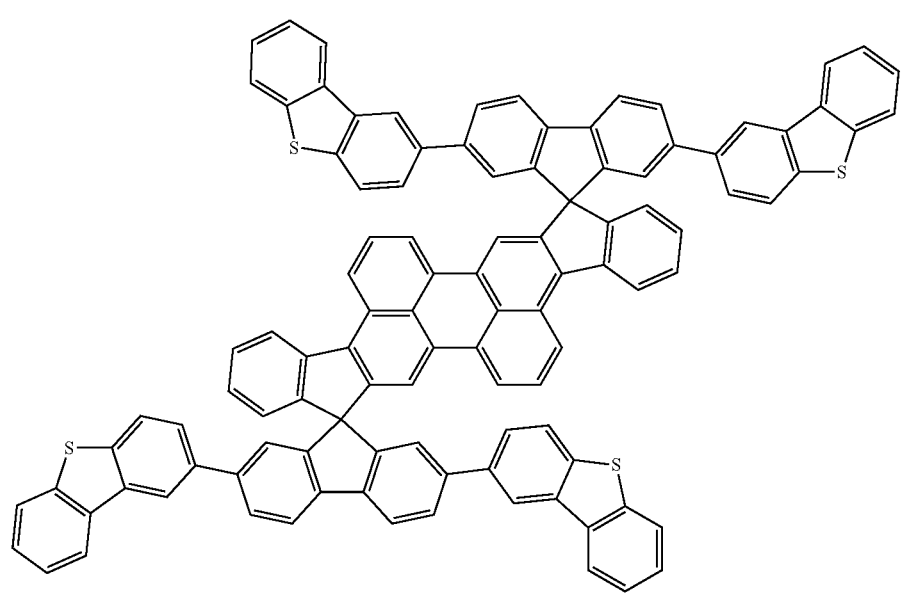

-continued 1-47

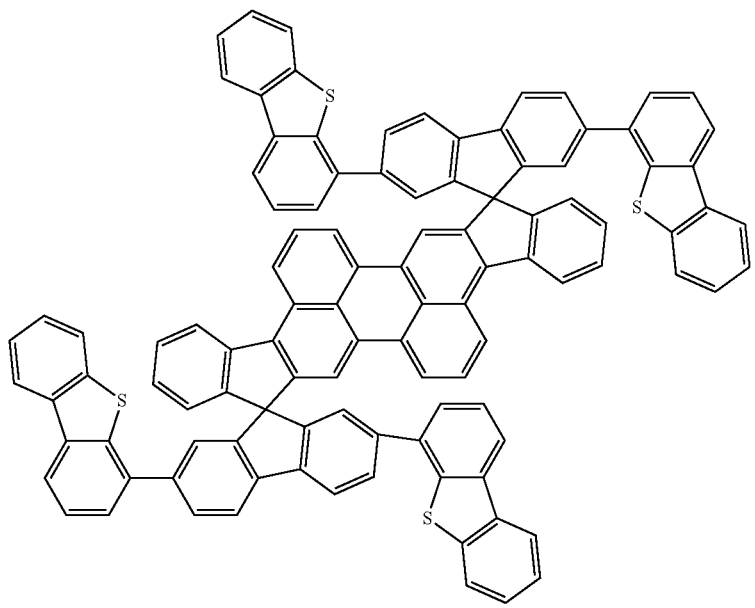

17. An organic light emitting display device, comprising:
a substrate;
an organic light emitting diode disposed on or over the substrate, the organic light emitting diode including:
a first electrode;
a second electrode facing the first electrode; and
an emitting material layer between the first and second electrodes; and
an encapsulation film covering the organic light emitting diode,
wherein the emitting material layer includes an organic compound of formula 1:

[Formula 1]

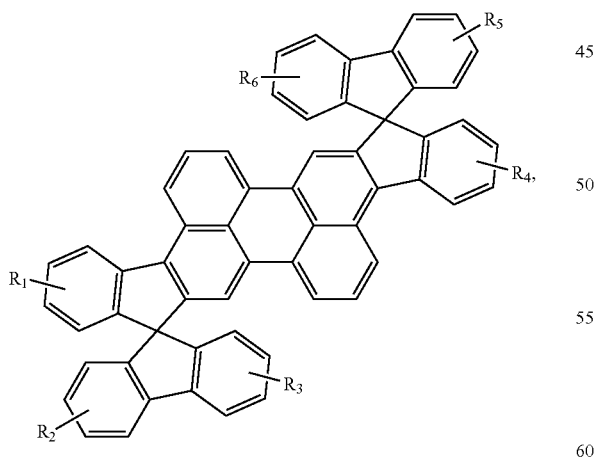

wherein each of $R_1$ to $R_6$ is independently selected from hydrogen, deuterium, tritium, halogen, a cyano group, a C1 to C20 alkyl group, a C6 to C30 aryl group, a C5 to C30 heteroaryl group and a C1 to C20 amine group.

18. The organic light emitting display device according to claim 17, wherein the organic compound is used as a fluorescent dopant, and the emitting material layer further includes a host and a delayed fluorescent dopant.

19. The organic light emitting display device according to claim 18, wherein the host is one of compounds in Formula 4:

[Formula 4]

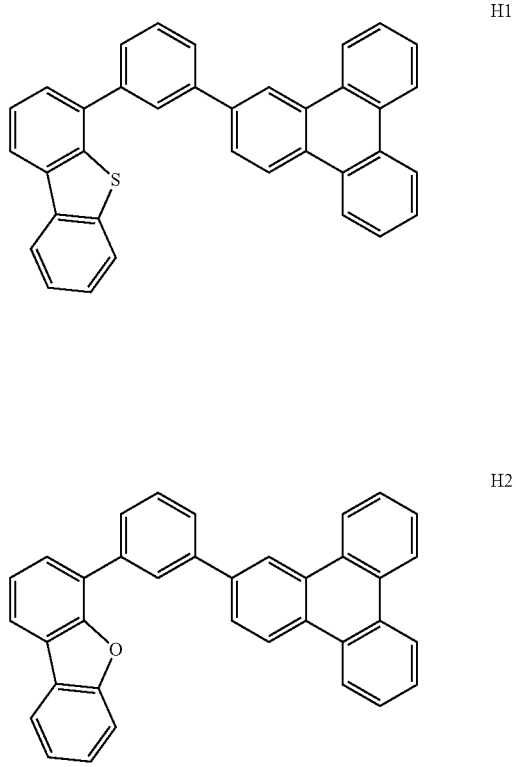

H3
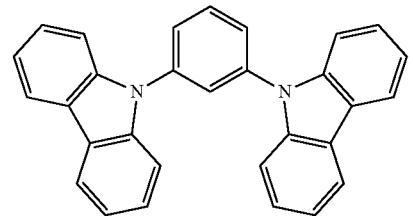
H4
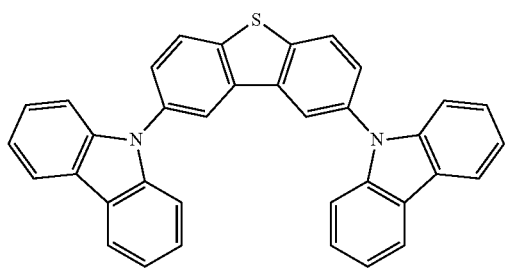
H5
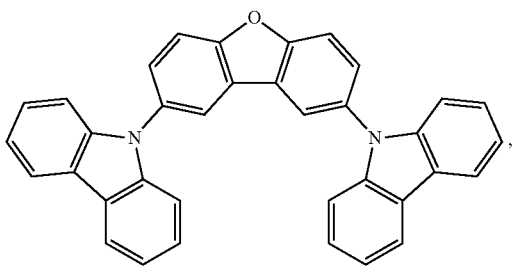
and
wherein the delayed fluorescent dopant is one of compounds in Formula 5:
[Formula 5]
T1
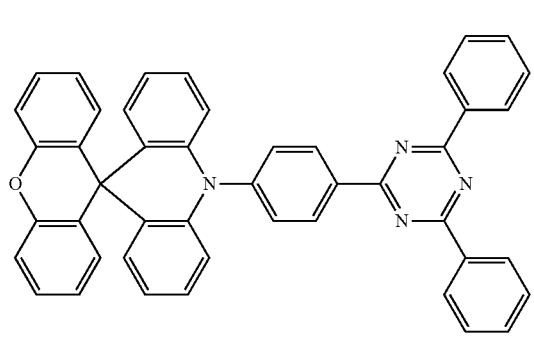
T2
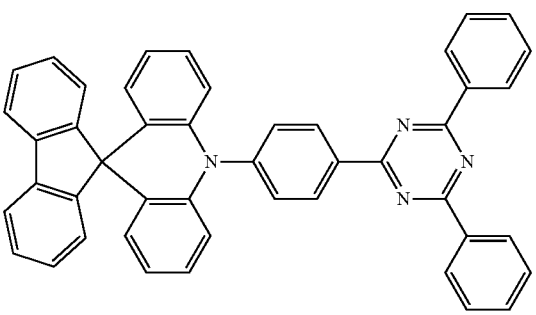
T3
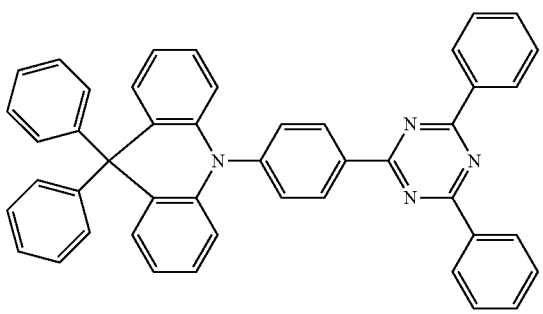
T4
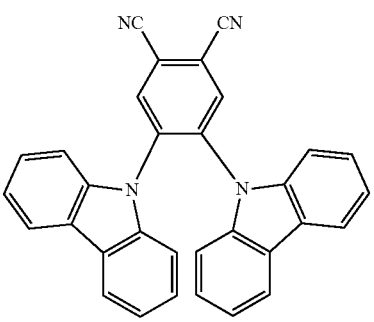
T5
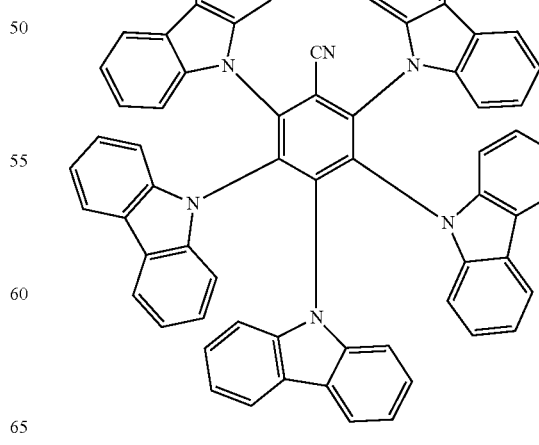

20. The organic light emitting display device according to claim 17, wherein the organic compound is selected from the group consisting of:
1-1
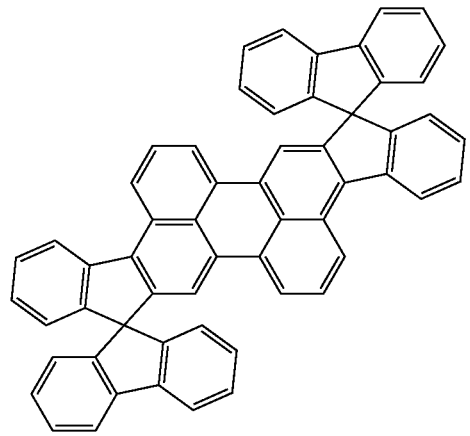
1-2
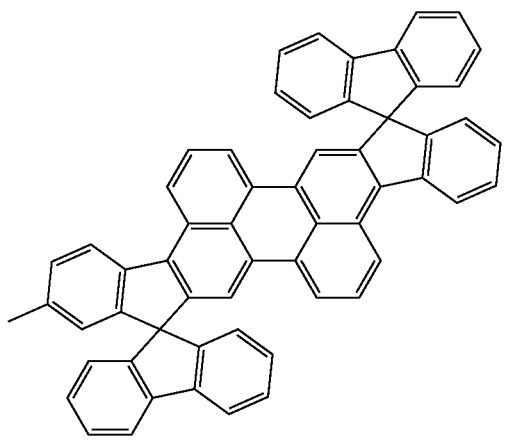
1-3
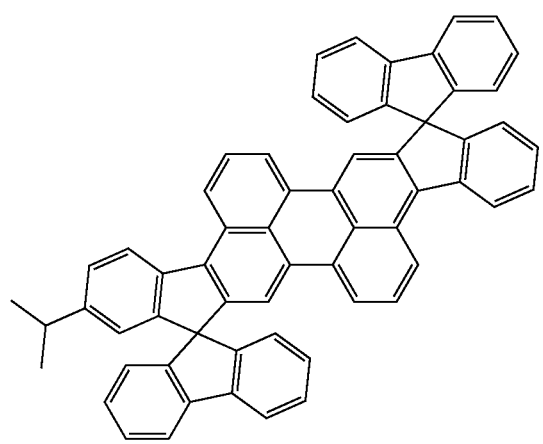
1-4
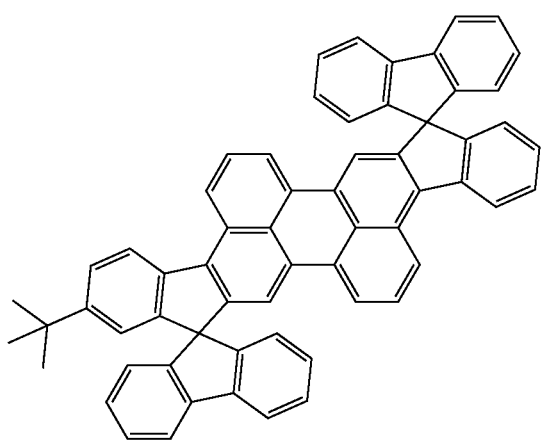
1-5
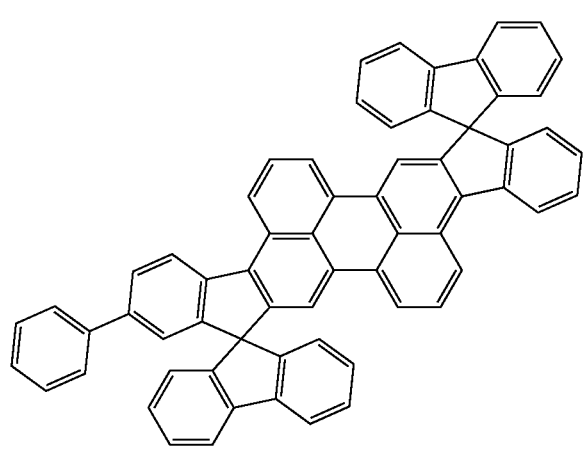
1-6
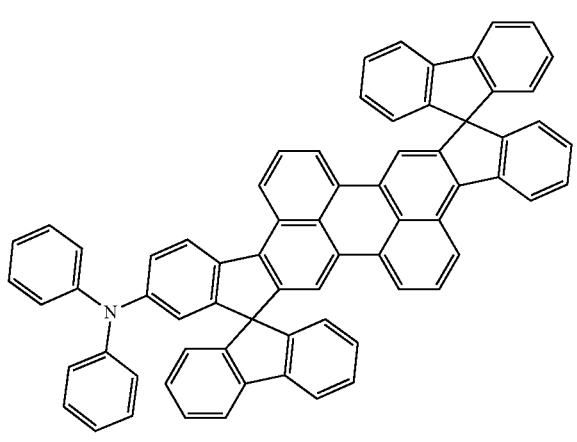

-continued
1-7
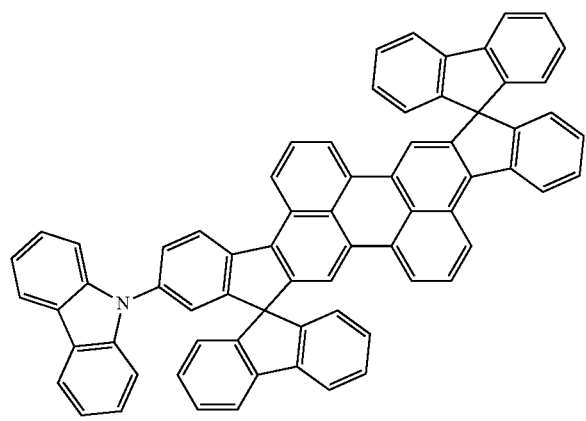
1-8
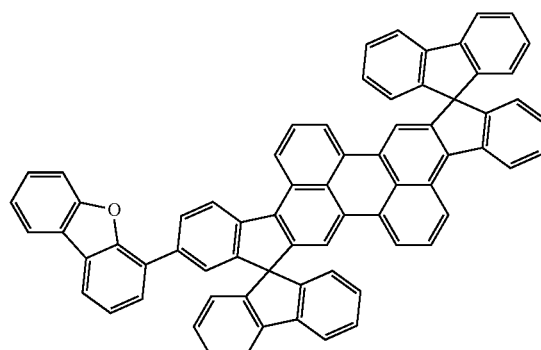
1-9
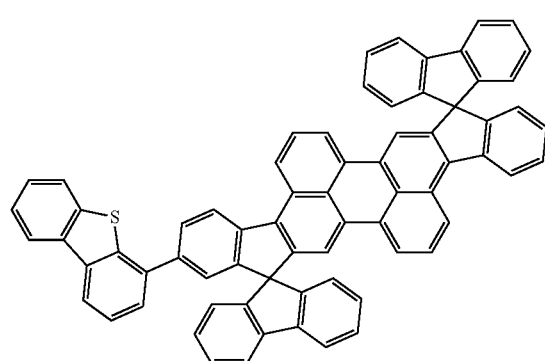
1-10
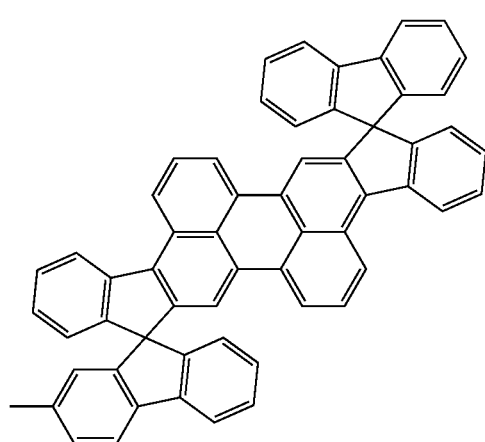
1-11
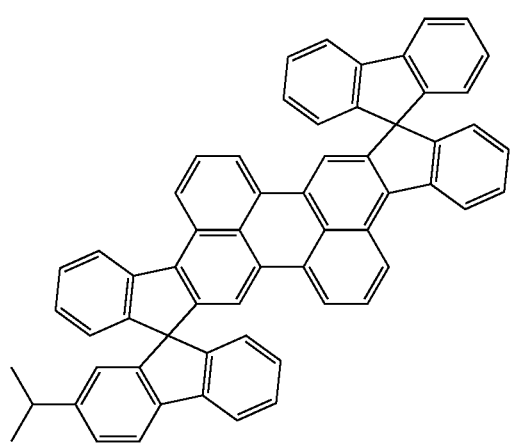
1-12
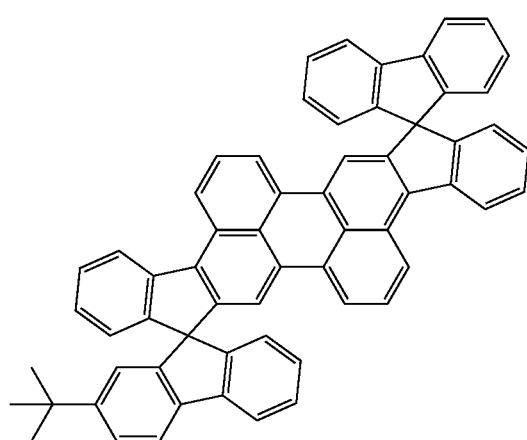

-continued
1-13
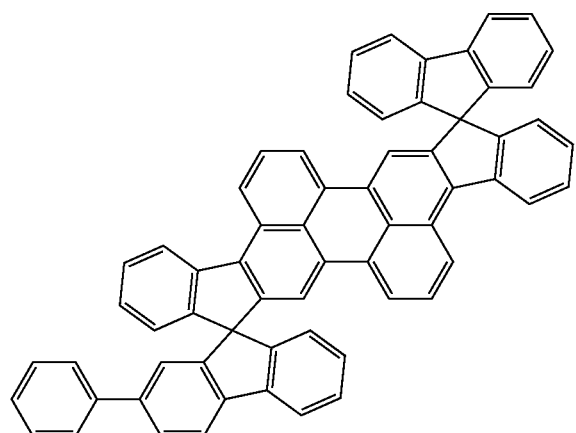
1-14
1-15
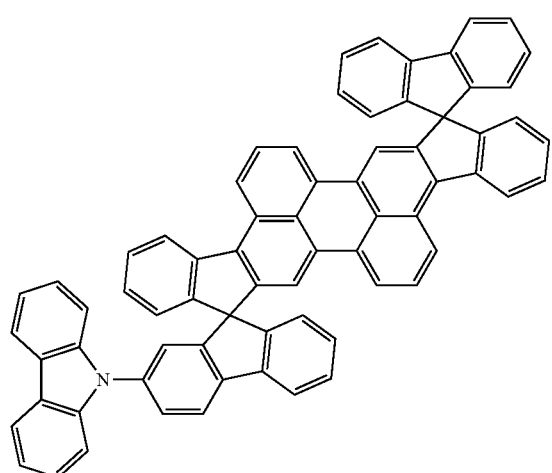
1-16
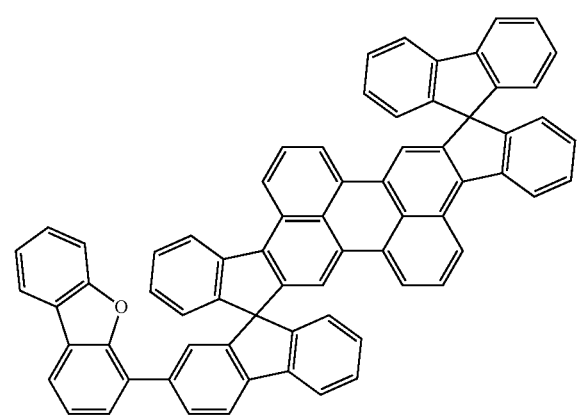
1-17
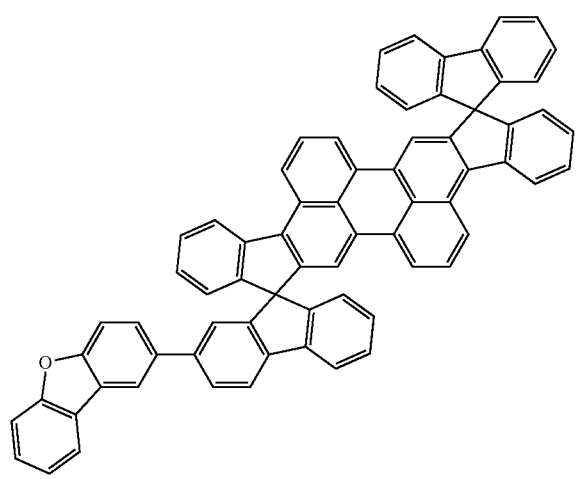
1-18
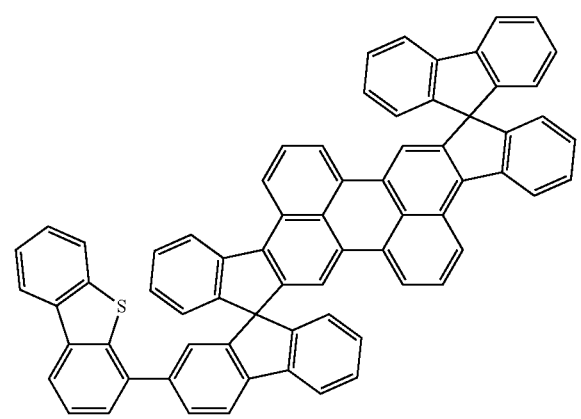

-continued
1-19
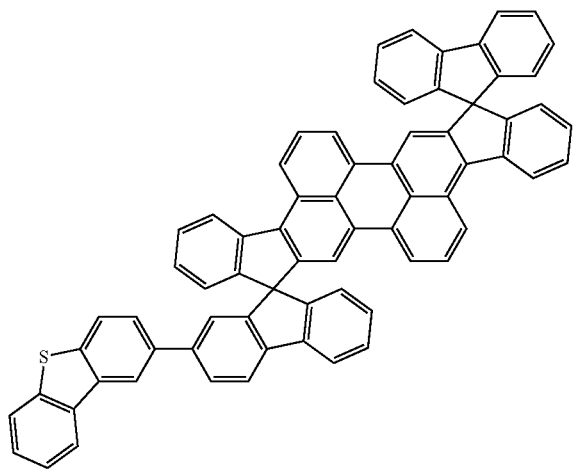
1-20
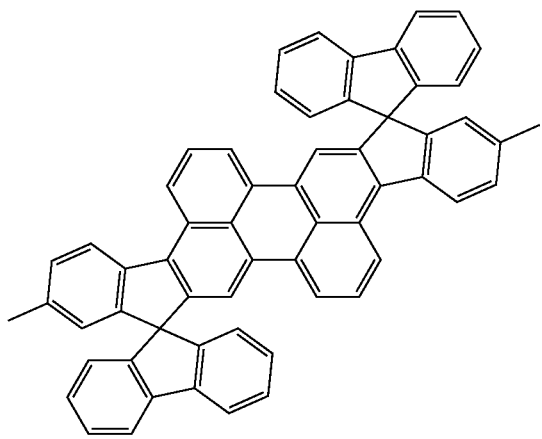
1-21
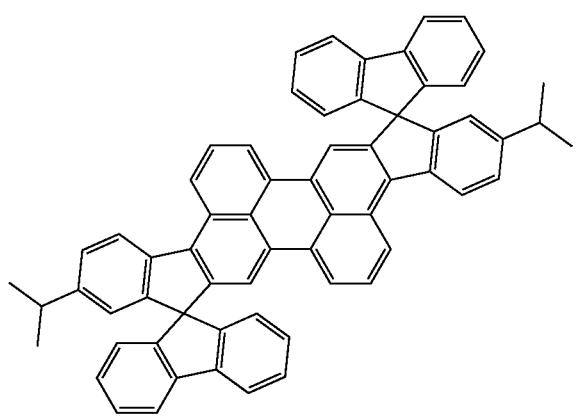
1-22
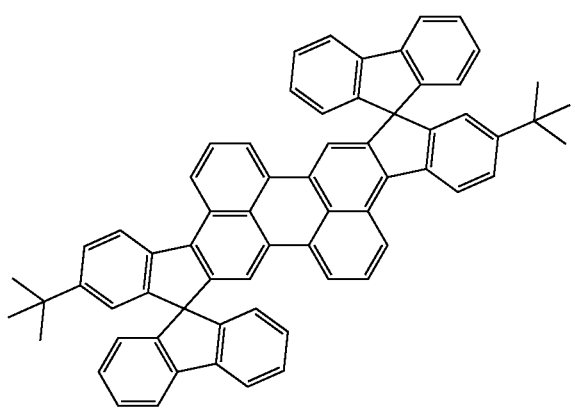
1-23
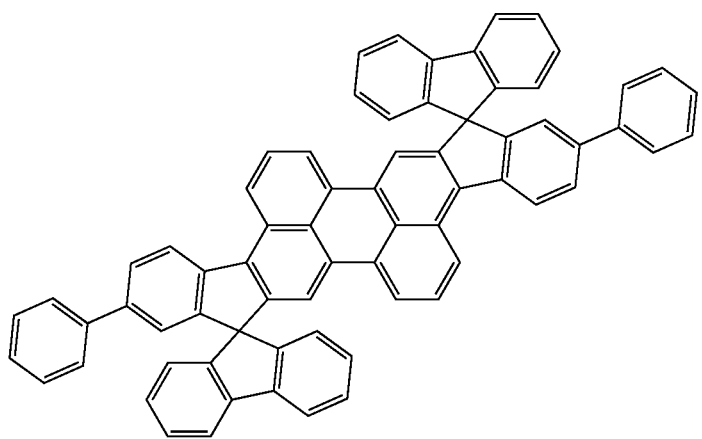

1-24
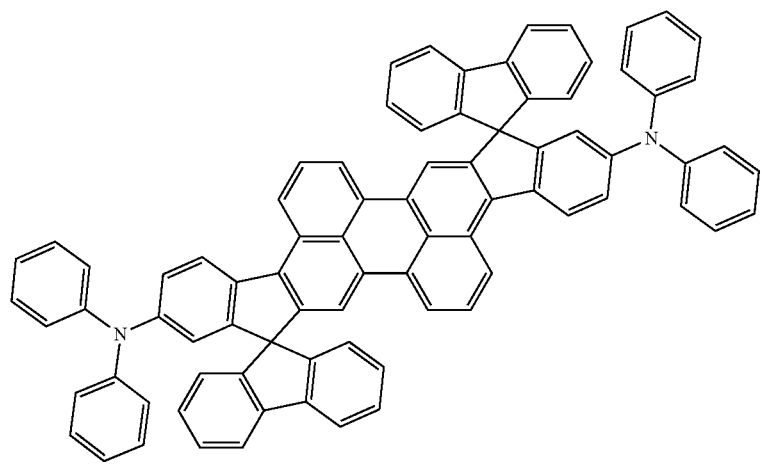
1-25
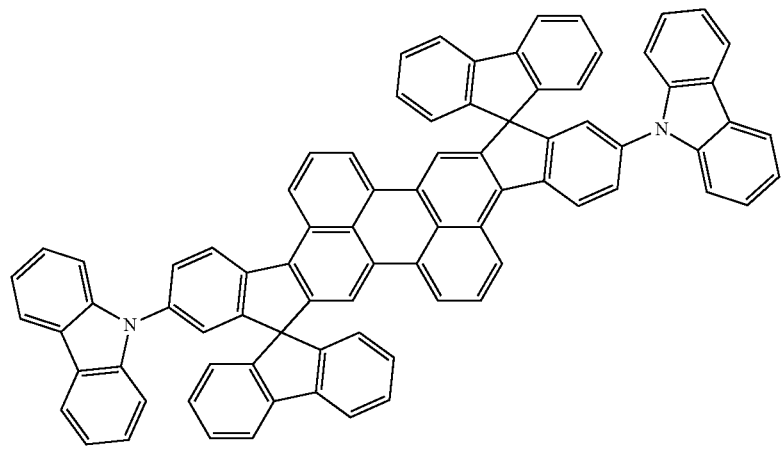
1-26
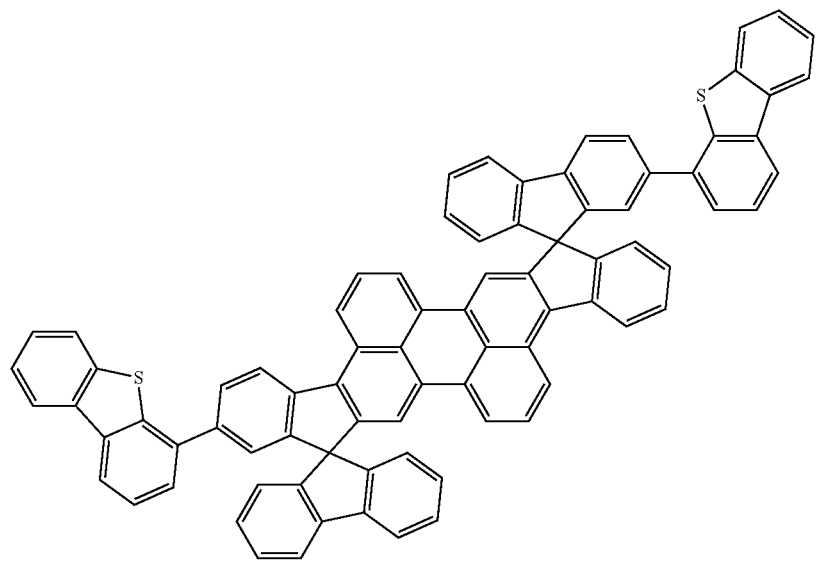

-continued
1-27
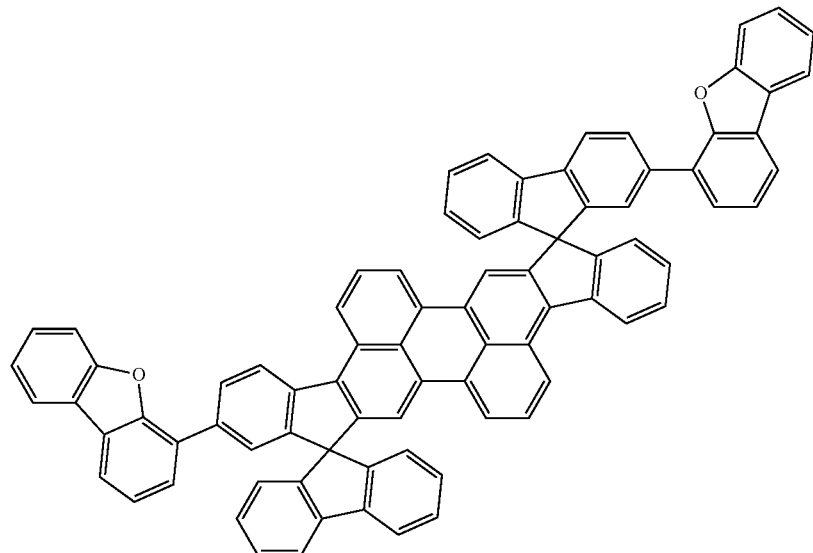
1-28
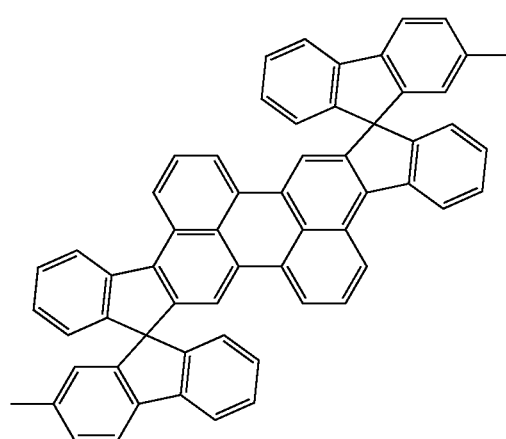
1-29
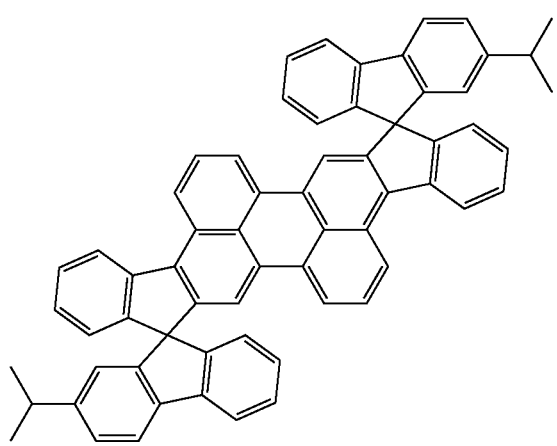
1-30
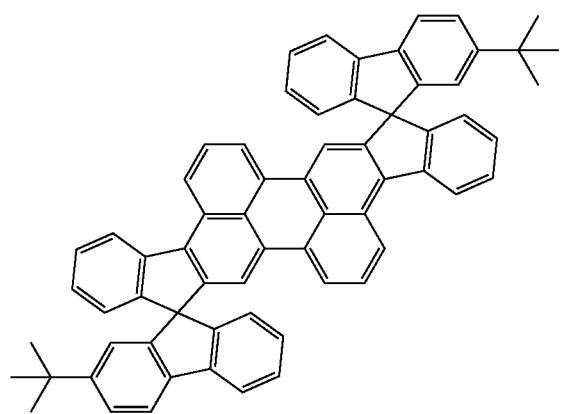
1-31
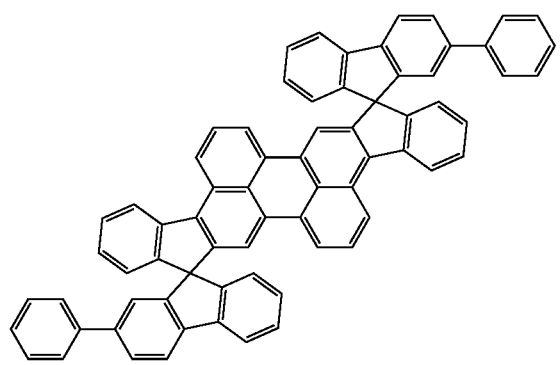

-continued
1-32
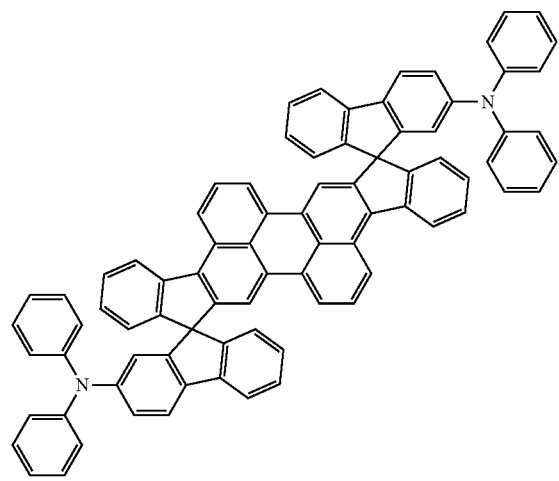
1-33
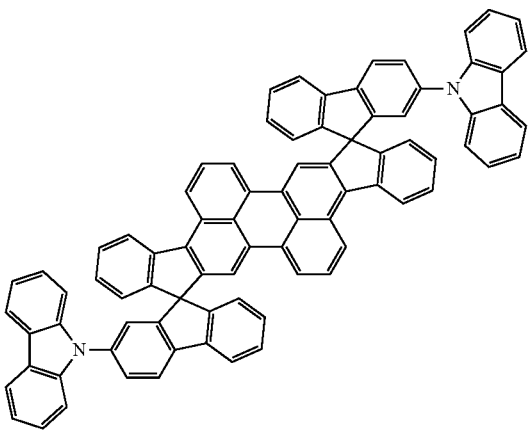
1-34
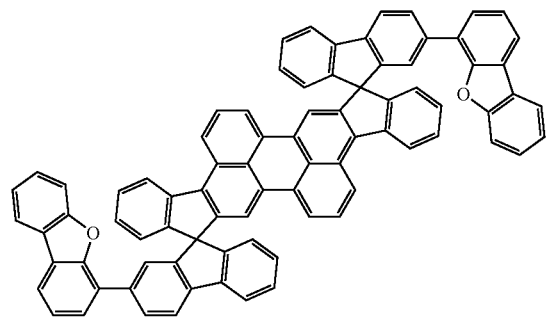
1-35
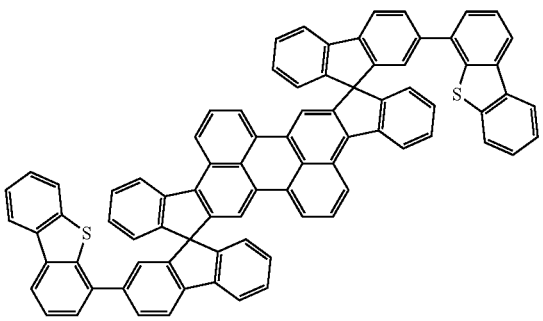
1-36
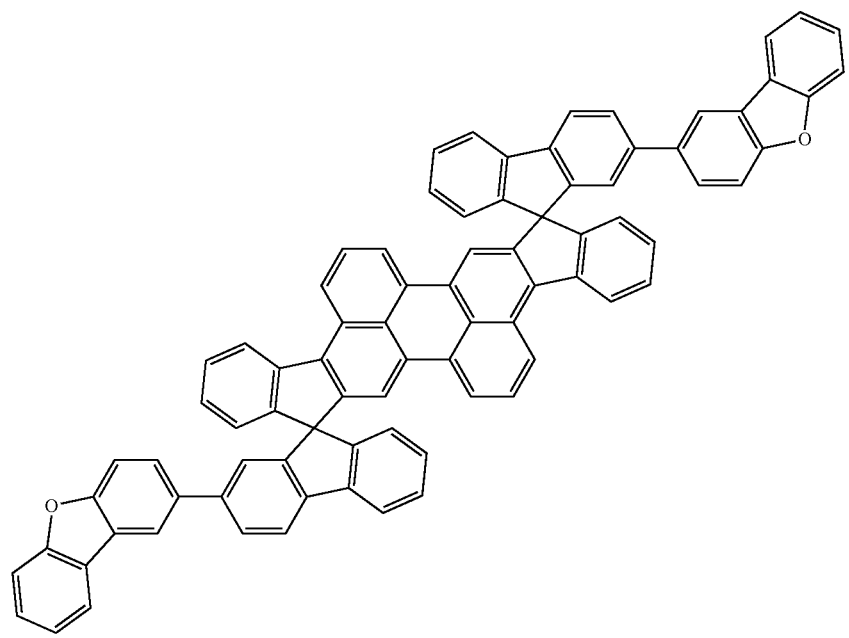

1-37
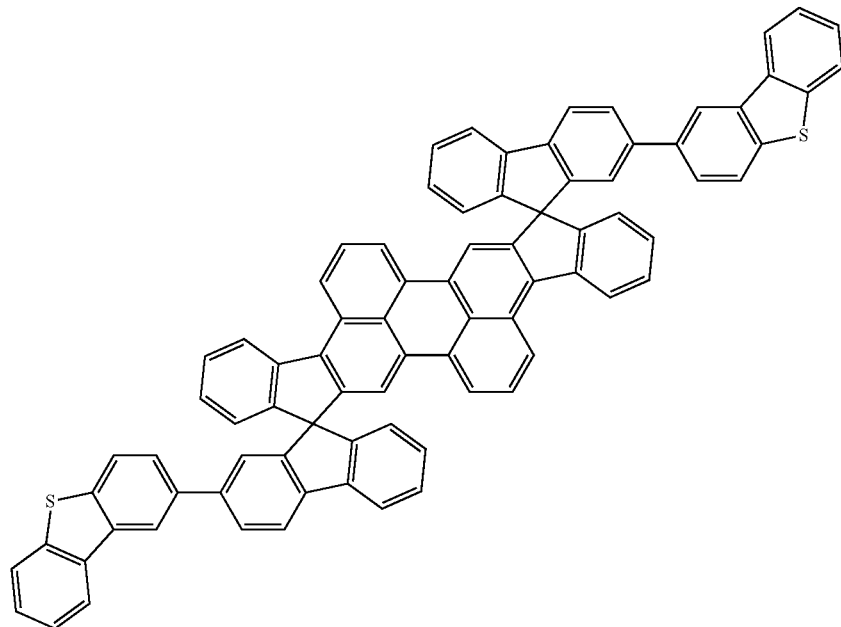
1-38
1-39
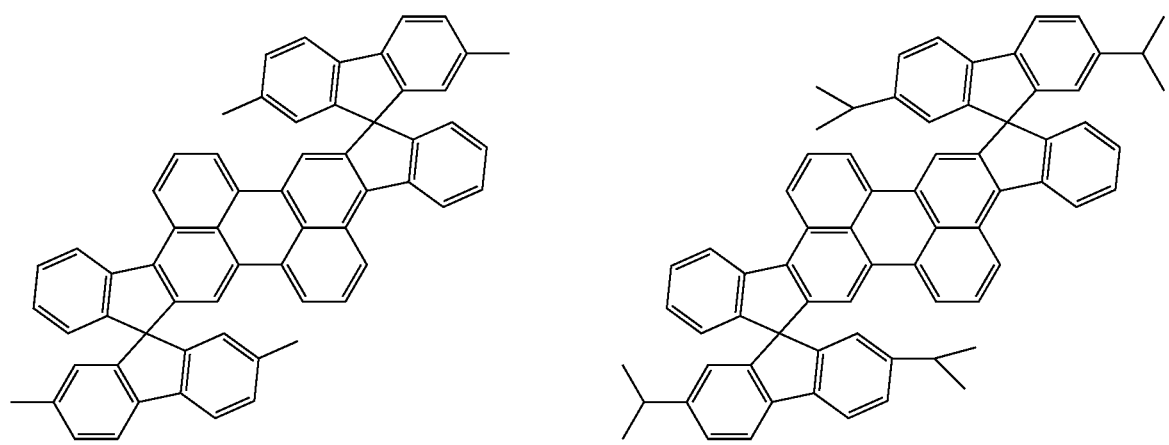
1-40
1-41
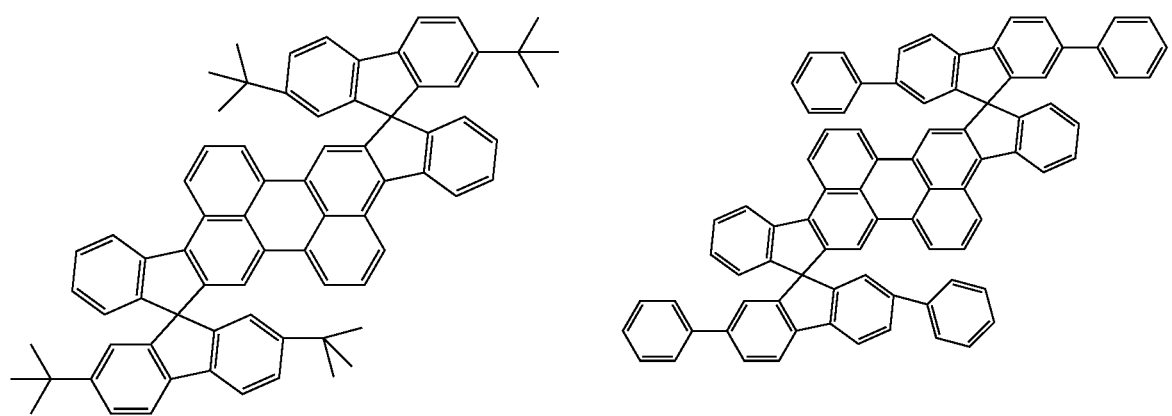

-continued
1-42
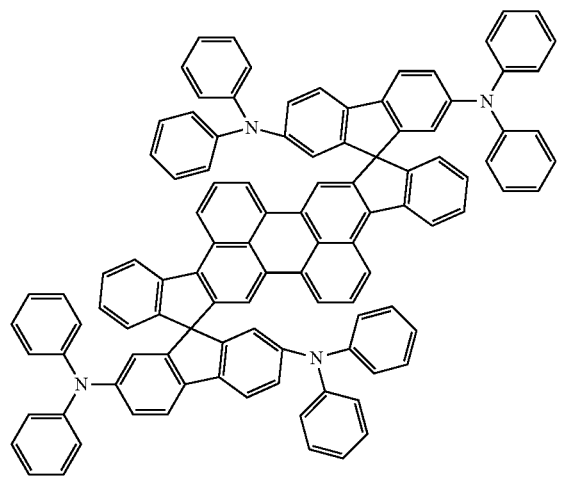
1-43
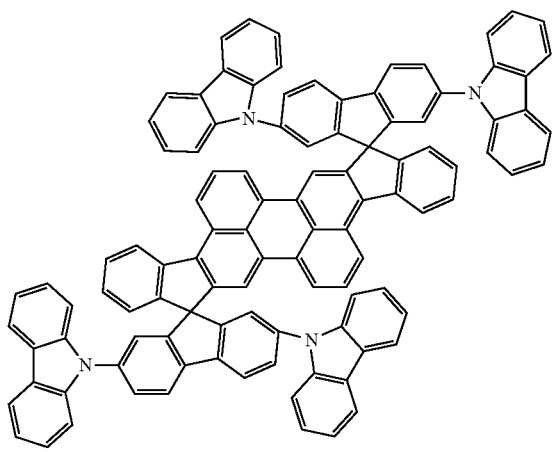
1-44
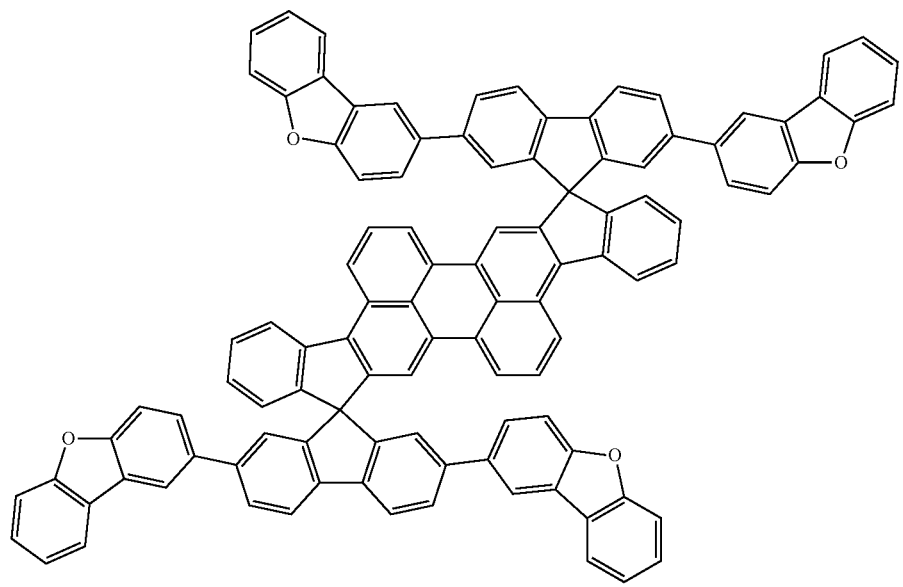

1-45
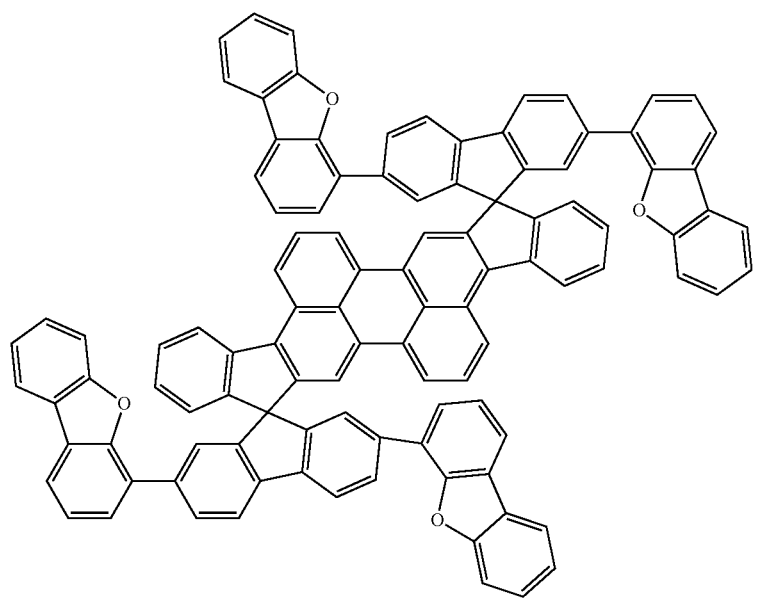
1-46
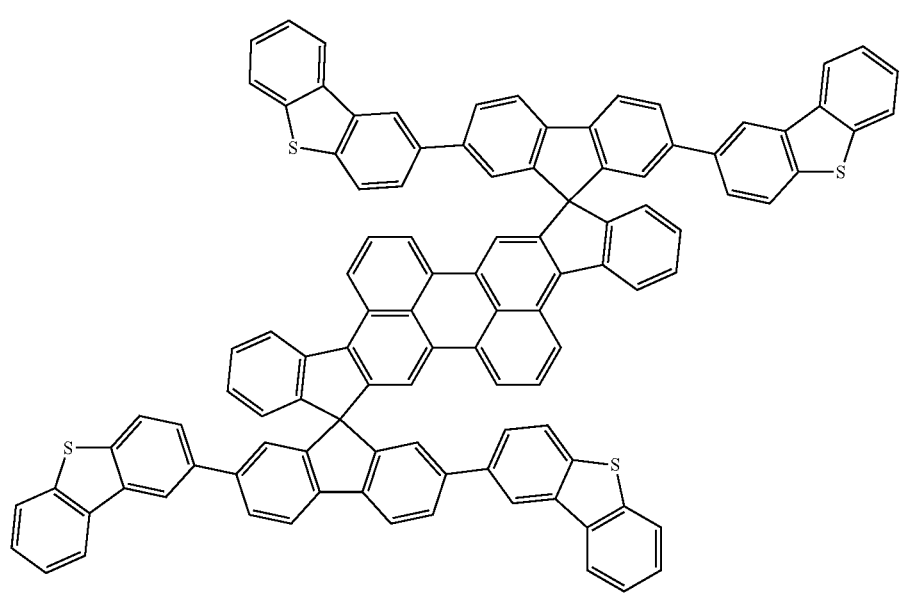

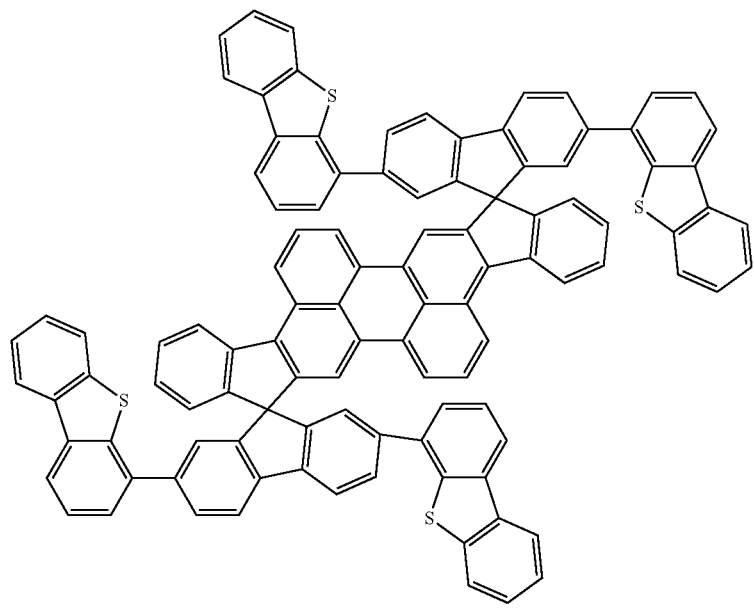
1-47
* * * * *